US012559574B2

(12) United States Patent
Kuo et al.

(10) Patent No.: US 12,559,574 B2
(45) Date of Patent: Feb. 24, 2026

(54) USE OF SUCCINATE AS BIOMARKER IN DIAGNOSIS AND TREATMENT OF CANCERS

(71) Applicant: National Health Research Institutes, Miaoli County (TW)

(72) Inventors: Cheng-Chin Kuo, Miaoli County (TW); Jing-Yiing Wu, Miaoli County (TW)

(73) Assignee: NATIONAL HEALTH RESEARCH INSTITUTES, Miaoli County (TW)

( * ) Notice: Subject to any disclaimer, the term of this patent is extended or adjusted under 35 U.S.C. 154(b) by 966 days.

(21) Appl. No.: 17/769,881

(22) PCT Filed: Oct. 16, 2020

(86) PCT No.: PCT/US2020/056052
§ 371 (c)(1),
(2) Date: Apr. 18, 2022

(87) PCT Pub. No.: WO2021/076942
PCT Pub. Date: Apr. 22, 2021

(65) Prior Publication Data
US 2022/0389117 A1     Dec. 8, 2022

Related U.S. Application Data

(60) Provisional application No. 62/916,376, filed on Oct. 17, 2019.

(51) Int. Cl.
*C07K 16/44*     (2006.01)
*A61P 35/00*     (2006.01)
*G01N 33/574*     (2006.01)

(52) U.S. Cl.
CPC .............. *C07K 16/44* (2013.01); *A61P 35/00* (2018.01); *G01N 33/57484* (2013.01)

(58) Field of Classification Search
None
See application file for complete search history.

(56) References Cited

U.S. PATENT DOCUMENTS

| | | |
|---|---|---|
| 2004/0181042 A1 | 9/2004 | Yanagisawa et al. |
| 2005/0152907 A1 | 7/2005 | Liang et al. |
| 2009/0324604 A1 | 12/2009 | Liu et al. |

FOREIGN PATENT DOCUMENTS

| | | | |
|---|---|---|---|
| WO | WO 2019/028530 A1 | 2/2019 | |
| WO | WO-2019053731 A1 * | 3/2019 | ............... A61P 1/00 |

OTHER PUBLICATIONS

Joel W. Goodman (Chapter 2, Antigenic Determinants and Antibody Combining Sites; in the Antigens; Editor Michael Sela, Academic Press; 1975).*

* cited by examiner

*Primary Examiner* — Laura B Goddard
(74) *Attorney, Agent, or Firm* — MUNCY, GEISSLER, OLDS & LOWE, P.C.

(57) ABSTRACT

The present invention discloses that cancer cells secrete succinate into extracellular milieu, which increases macrophage migration and mediates TAM polarization. Furthermore, succinate induces cancer cell EMT, enhances cancer cell migration, and promotes cancer metastasis in murine models. It is indicated in the present invention that serum succinate concentration is elevated in patients with lung cancer when compared to healthy subjects. It implies that during cancer development and progression, cancer cells release a large quantity of succinate into the circulation. As shown in the present invention, serum succinate has a high discriminatory power, it represents a new class of circulating oncometabolite with potential value for predicting NSCLC. Furthermore, as elevation of succinate level in LLC tumor model is accompanied by increased TAMs in the subcutaneous tumors and enhanced cancer metastasis, serum succinate may be a useful therapeutic biomarker for NSCLC treatment. The present invention also provides an anti-succinate antibody that can serve as a cancer therapeutic agent.

10 Claims, 51 Drawing Sheets
Specification includes a Sequence Listing.

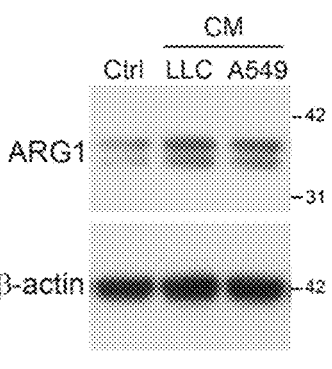
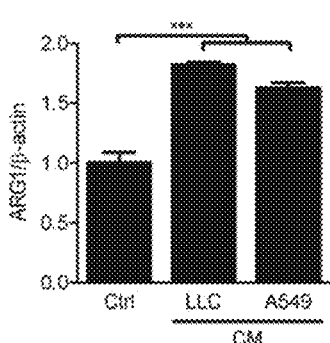
Fig. 1A
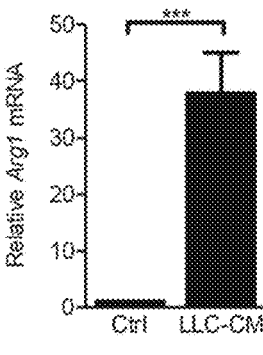
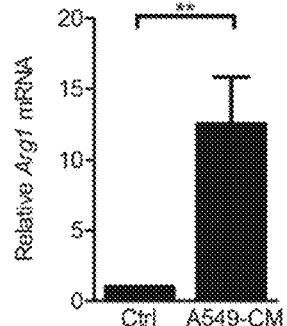
Fig. 1B
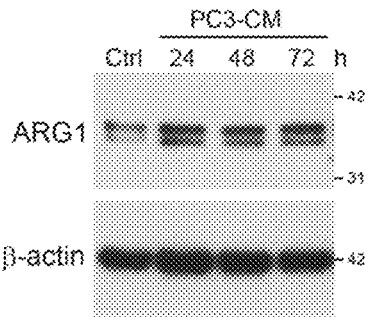
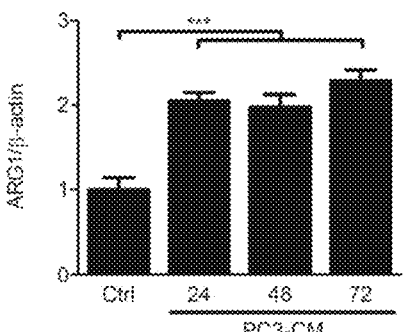
Fig. 1C
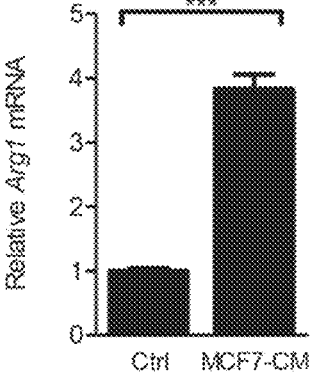
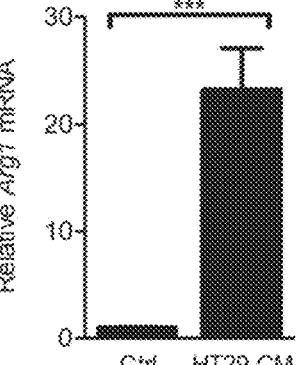
Fig. 1D

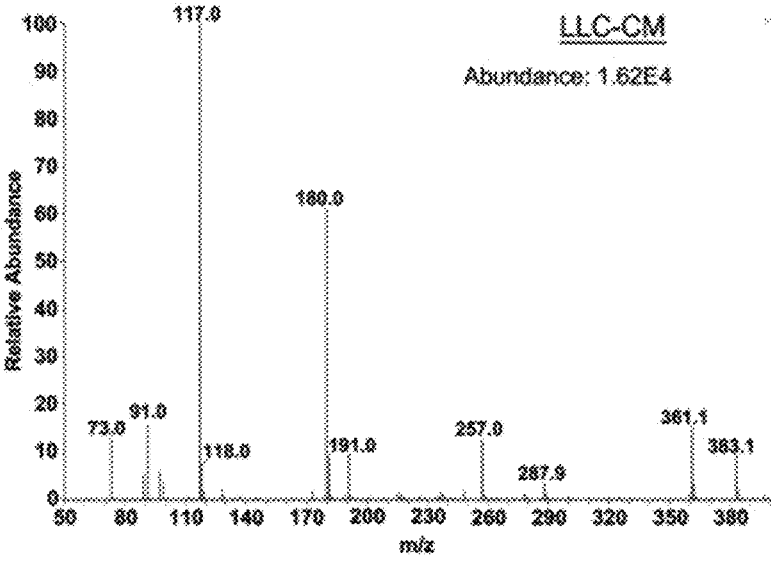
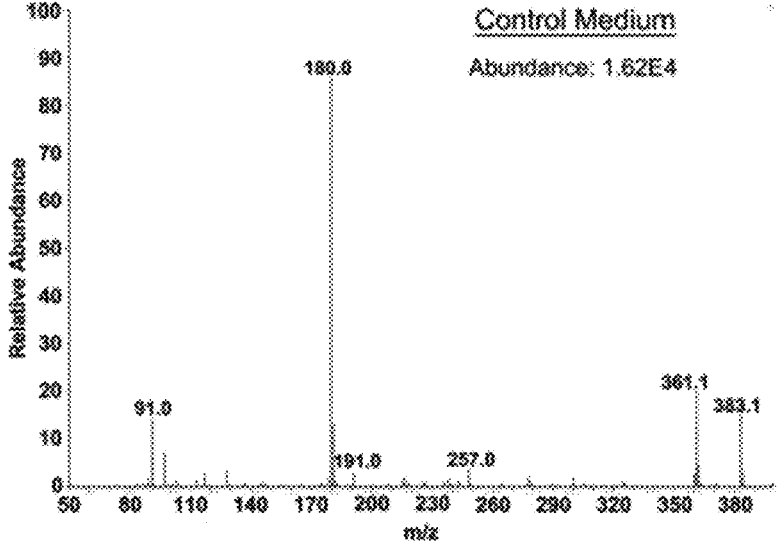
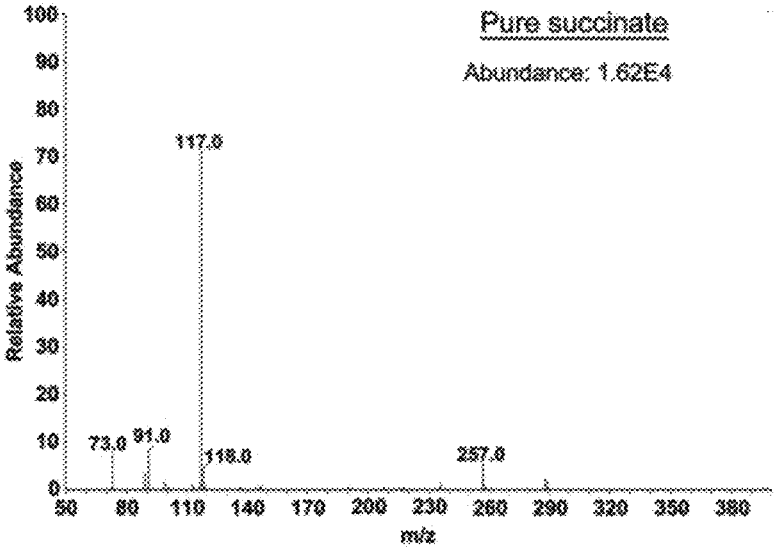
Fig. 2C

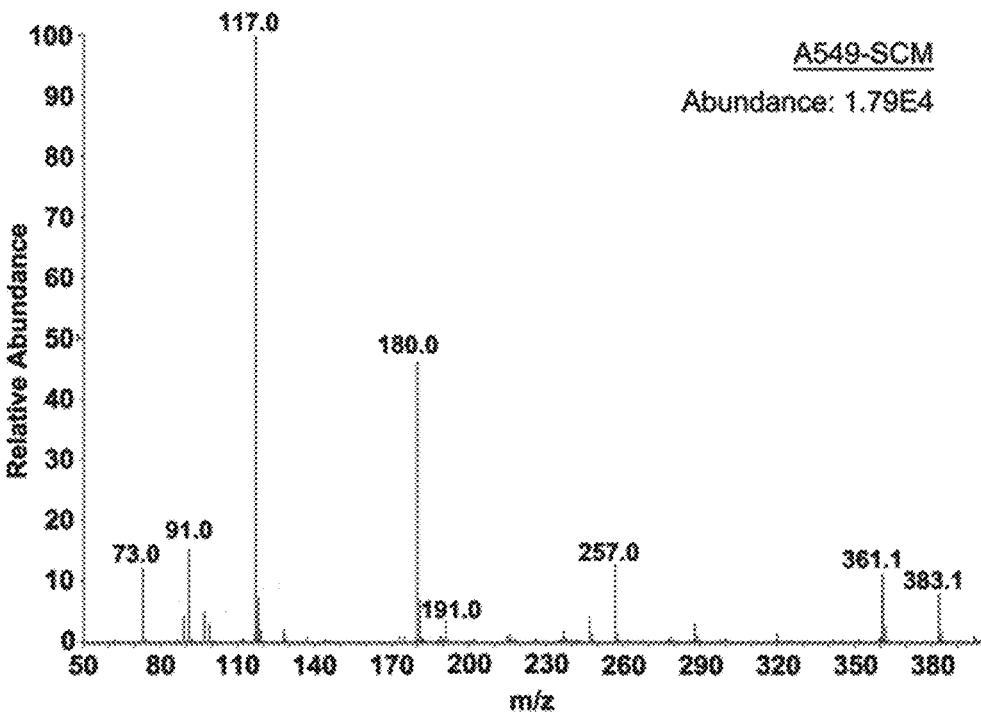
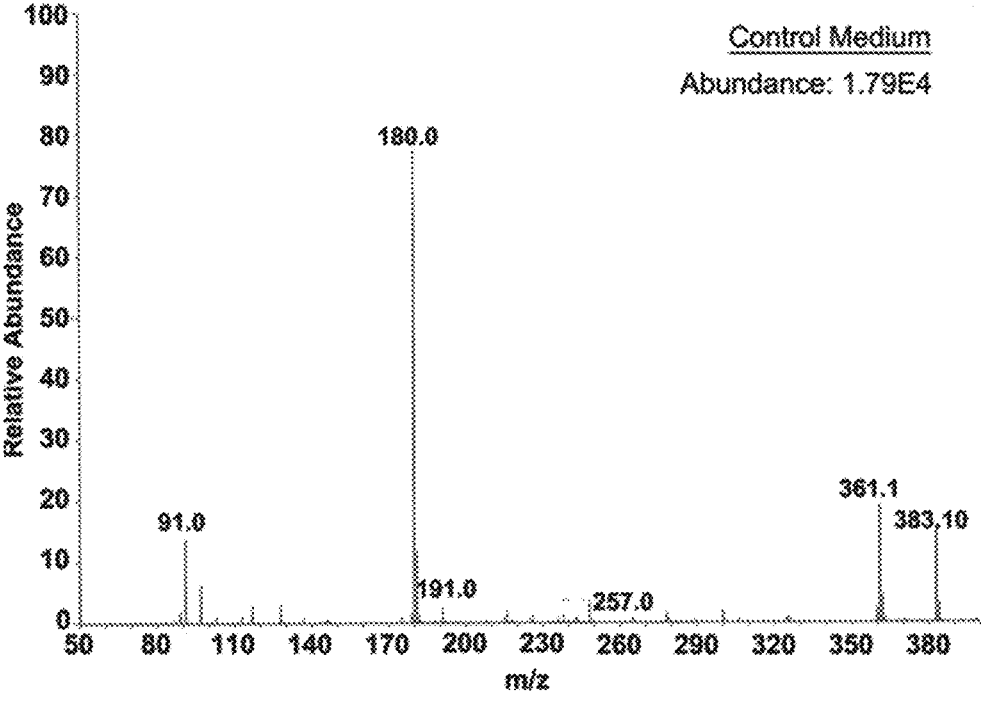
Fig. 2D

| | Saline | 20 | 100 |
|---|---|---|---|
| Mean | 28.71 | 41.07 | 52.48 |
| SEM | 3.996 | 5.639 | 4.379 |

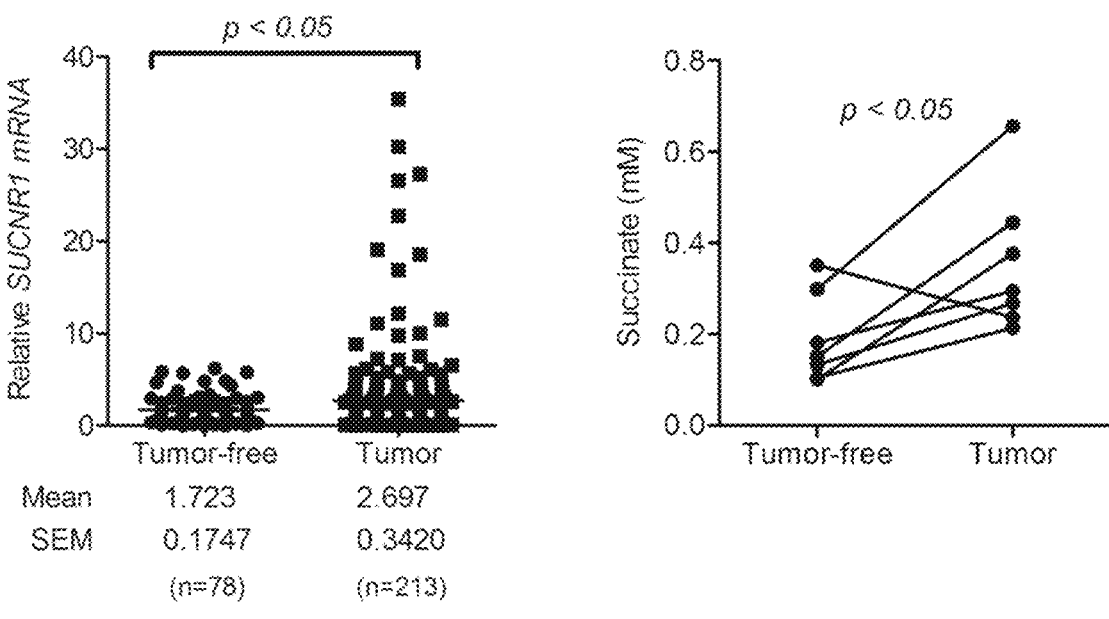
|  | Tumor-free | Tumor |
| --- | --- | --- |
| Mean | 1.723 | 2.697 |
| SEM | 0.1747 | 0.3420 |
|  | (n=78) | (n=213) |
Fig. 5A                  Fig. 5B
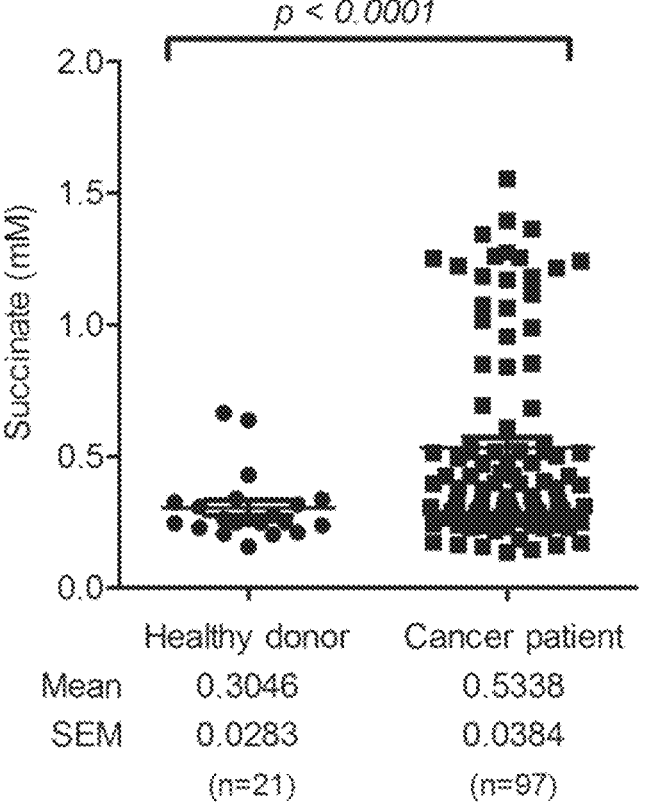
|  | Healthy donor | Cancer patient |
| --- | --- | --- |
| Mean | 0.3046 | 0.5338 |
| SEM | 0.0283 | 0.0384 |
|  | (n=21) | (n=97) |
Fig. 5C

| | Lung cancer patients ($n = 97$) |
|---|---|
| AUC (95% CI) | 0.7032 (0.5937-0.8128) |
| *P* value | 0.0036 |
| Cutoff | 0.344 |
| Sensitivity (%) | 53.61 |
| Specificity (%) | 85.71 |

CI: confidence interval

| | Dilution | Protein A Purified Anti-succinate acid Antibody |
|---|---|---|
| 1 | 1:1,000 | 1.956 |
| 2 | 1:2,000 | 1.765 |
| 3 | 1:4,000 | 1.501 |
| 4 | 1:8,000 | 1.205 |
| 5 | 1:16,000 | 0.829 |
| 6 | 1:32,000 | 0.527 |
| 7 | 1:64,000 | 0.323 |
| 8 | 1:128,000 | 0.190 |
| 9 | 1:256,000 | 0.131 |
| 10 | 1:512,000 | 0.094 |
| 11 | Blank | 0.061 |
| 12 | Blank | 0.061 |
| | Titer | 1:256,000 |

Starting dilution: 1:1,000 (Equivalent to 10 mg/ml)
The titer is the highest dilution with S/B (Signal/Blank) >=2.1

Fig. 6A

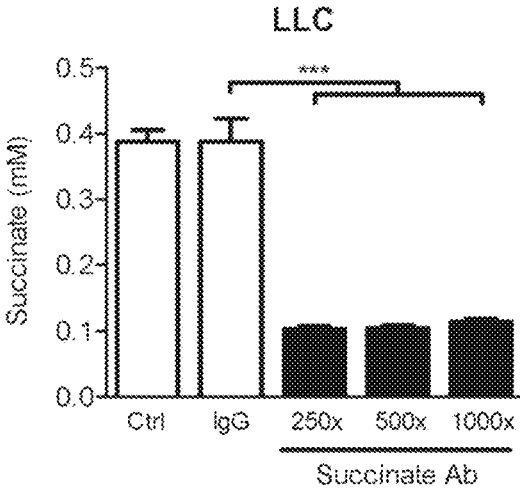
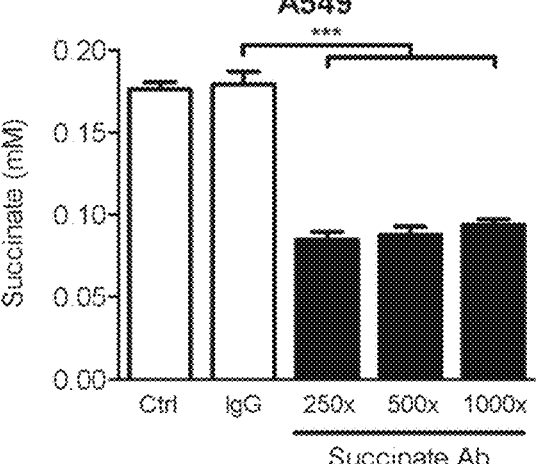
Fig. 6B
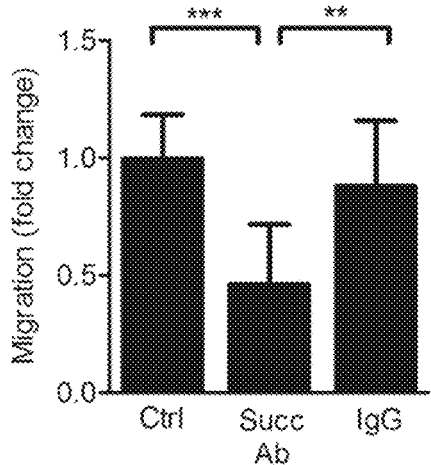
Fig. 6C

Antibody sequences of 6G10F6 were listed as below:

Heavy chain: DNA sequence (411 bp)  (SEQ ID NO: 1)

Leader sequence-FR1-CDR1-FR2-CDR2-FR3-CDR3-FR4

ATGAGAGTGCTGATTCTTTTGTGGCTGTTCACAGCCTTTCCTGGTATCCTGTCTGATGTGCAGCTTC

AGGAGTCGGGACCTGGCCTGGTGAAACCTTCTCAGTCTCTGTCCCTCACCTGCACTGTCACTGGCTA

CTCAATCACCAGTGATTATGCCTGGAACTGGTTCCGGCAGTTTCCAGGAAACAAACTGGAGTGGATG

GGCTACACAAGCTACAGTGGTAGCACTAGCTATAACCCATCTCTCAAAAGTCGAATCTCTATCACTC

GAAACACATCCAAGAACCAGATCTTCCTGCAGTTGAATTCTGTGACTCCTGAGGACACAGCCACATA

TTACTGTGCAAGAGAGGTTACTACGTTTGGATACTTTGACTACTGGGGCCAAGGCACCACTCTCACA

GTCTCCTCA

Heavy chain: Amino acids sequence (137 aa)  (SEQ ID NO: 2)

Leader sequence-FR1-CDR1-FR2-CDR2-FR3-CDR3-FR4

MRVLILLWLFTAFPGILSDVQLQESGPGLVKPSQSLSLTCTVTGYSITSDYAWNWFRQFPGNKLEWM

GYTSYSGSTSYNPSLKSRISITRNTSKNQIFLQLNSVTPEDTATYYCAREVTTFGYFDYWGQGTTLT

VSS

Light chain: DNA sequence (384 bp)  (SEQ ID NO: 3)

Leader sequence-FR1-CDR1-FR2-CDR2-FR3-CDR3-FR4

ATGGCCTGGACTTCACTTATACTCTCTCTCCTGGCTCTCTGCTCAGGAGCCAGTTCCCAGGCTGTTG

TGACTCAGGAATCTGCACTCACCACATCACCTGGTGGAACAGTCATACTCACTTGTCGCTCAAGTAC

TGGGGCTGTTACAACTAGTAACTATGCCAACTGGGTCCAAGAAAAACCAGATCATTATTCACTGGT

CTAATAGGTGGTACCAGCAACCGAGCTCCAGGTGTTCCTGTCAGATTCTCAGGCTCCCTGATTGGAG

ACAAGGCTGCCCTCACCATCACAGGGGCACAGACTGAGGATGATGCAATGTATTTCTGTGCTCTATG

GTACAGCACCCATTATGTTCTCGGCGGTGGAACCAAGGTCACTGTCCTA

Light chain: Amino acids sequence (128 aa)  (SEQ ID NO: 4)

Leader sequence-FR1-CDR1-FR2-CDR    3-FR4

MAWTSLILSLLALCSGASSQAVVTQESALTTSPGGTVILTCRSSTGAVTTSNYANWVQEKPDHLFTG

LIGGTSNRAPGVPVRFSGSLIGDKAALTITGAQTEDDAMYFCALWYSTHYVLGGGTKVTVL

Fig. 8

Antibody sequences of 6G10G5 were listed as below:

Heavy chain: DNA sequence (411 bp) (SEQ ID NO: 5)

Leader sequence-FR1-CDR1-FR2-CDR2-FR3-CDR3-FR4

ATGAGAGTGCTGATTCTTTTGTGGCTGTTCACAGCCTTTCCTGGTATCCTGTCTGATGTGCAGCTTC

AGGAGTCGGGACCTGGCCTGGTGAAACCTTCTCAGTCTCTGTCCCTCACCTGCACTGTCACTGGCTA

CTCAATCACCAGTGATTATGCCTGGAACTGGTTCCGGCAGTTTCCAGGAAACAAACTGGAGTGGATG

GGCTACACAAGCTACAGTGGTAGCACTAGCTATAACCCATCTCTCAAAAGTCGAATCTCTATCACTC

GAAACACATCCAAGAACCAGATCTTCCTGCAGTTGAATTCTGTGACTCCTGAGGACACAGCCACATA

TTACTGTGCAAGAGAGGTTACTACGTTTGGATACTTTGACTACTGGGGCCAAGGCACCACTCTCACA

GTCTCCTCA

Heavy chain: Amino acids sequence (137 aa) (SEQ ID NO: 6)

Leader sequence-FR1-CDR1-FR2-CDR2-FR3-CDR3-FR4

MRVLILLWLFTAFPGILSDVQLQESGPGLVKPSQSLSLTCTVTGYSITSDYAWNWFRQFPGNKLEWM

GYTSYSGSTSYNPSLKSRISITRNTSKNQIFLQLNSVTPEDTATYYCAREVTTFGYFDYWGQGTTLT

VSS

Light chain: DNA sequence (384 bp) (SEQ ID NO: 7)

Leader sequence-FR1-CDR1-FR2-CDR2-FR3-CDR3-FR4

ATGGCCTGGACTTCACTTATACTCTCTCTCCTGGCTCTCTGCTCAGGAGCCAGTTCCCAGGCTGTTG

TGACTCAGGAATCTGCACTCACCACATCACCTGGTGGAACAGTCATACTCACTTGTCGCTCAAGTAC

TGGGGCTGTTACAACTAGTAACTATGCCAACTGGGTCCAAGAAAAACCAGATCATTTATTCACTGGT

CTAATAGGTGGTACCAGCAACCGAGCTCCAGGTGTTCCTGTCAGATTCTCAGGCTCCCTGATTGGAG

ACAAGGCTGCCCTCACCATCACAGGGGCACAGACTGAGGATGATGCAATGTATTTCTGTGCTCTATG

GTACAGCACCCATTATGTTCTCGGCGGTGGAACCAAGGTCACTGTCCTA

Light chain: Amino acids sequence (128 aa) (SEQ ID NO: 8)

Leader sequence-FR1-CDR1-FR2-CDR2 FR3 CDR3-FR4

MAWTSLILSLLALCSGASSQAVVTQESALT        TCRSSTGAVTTSNYANWVQEKPDHLFTG

LIGGTSNRAPGVPVRFSGSLIGDKAALTITGAQTEDDAMYFCALWYSTHYVLGGGTKVTVL

Fig. 9

Cloning strategy

Heavy chain:

EcoRI--Kozak sequence--Artificial signal peptide-- Heavy chain variable region--- human IgG4 constant region---stop codon--HindIII

Heavy chain sequence: 465aa  (SEQ ID NO: 35)

MGWSCIILFLVATATGVHSDVQLQESGPGLVKPSQSLSLTCTVTGYSITSDYAWNWF
RQFPGNKLEWMGYTSYSGSTSYNPSLKSRISITRNTSKNQIFLQLNSVTPEDTATYYC
AREVTTFGYFDYWGQGTTLTVSSASTKGPSVFPLAPCSRSTSESTAALGCLVKDYFPE
PVTVSWNSGALTSGVHTFPAVLQSSGLYSLSSVVTVPSSSLGTKTYTCNVDHKPSNTK
VDKRVESKYGPPCPSCPAPEFLGGPSVFLFPPKPKDTLMISRTPEVTCVVVDVSQEDPE
VQFNWYVDGVEVHNAKTKPREEQFNSTYRVVSVLTVLHQDWLNGKEYKCKVSNK
GLPSSIEKTISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHNHYTQKS
LSLSLGK

Gene sequence: 1422bp  (SEQ ID NO: 36)

GAATTCCCGCCGCCACCATGGGCTGGTCCTGCATCATTCTGTTTCTGGTGGCCACA
GCCACCGGCGTGCACTCTGATGTTCAGCTGCAAGAGTCTGGCCCTGGCCTGGTCA
AGCCTAGCCAAAGCCTGAGCCTGACCTGTACCGTGACCGGCTACAGCATCACCAG
CGACTACGCCTGGAACTGGTTCAGACAGTTCCCCGGCAACAAGCTGGAATGGATG
GGCTACACAAGCTACAGCGGCAGCACCAGCTACAACCCCAGCCTGAAGTCCCGG
ATCAGCATCACACGGAACACCAGCAAGAACCAGATCTTCCTGCAGCTCAACAGC
GTGACCCCTGAGGATACCGCCACCTACTACTGCGCCAGAGAAGTGACCACCTTCG
GCTACTTCGACTACTGGGGCCAGGGCACCACACTGACAGTGTCTAGCGCCTCTAC
AAAGGGCCCCAGCGTTTTCCCACTGGCTCCCTGTAGCAGAAGCACCAGCGAATCT
ACAGCTGCTCTGGGCTGCCTCGTGAAGGACTACTTTCCTGAGCCAGTGACCGTGT
CCTGGAACTCTGGCGCTCTGACATCTGGCGTGCACACCTTTCCAGCCGTGCTGCA
ATCTAGCGGCCTGTACTCTCTGAGCAGCGTGGTCACAGTGCCTAGCTCTAGCCTG
GGCACCAAGACCTACACCTGTAATGTGGATCACAAGCCCAGCAACACCAAGGTG
GACAAGAGAGTGGAATCTAAGTACGGCCCTCCTTGTCCTAGCTGCCCCGCTCCTG
AATTTCTGGGCGGACCTTCCGTGTTCCTGTTCCTCCAAAGCCTAAGGACACCCTG
ATGATCAGCAGAACCCCTGAAGTGACCTGCGTGGTGGTGGACGTGTCCCAAGAG
GATCCTGAGGTGCAGTTCAATTGGTACGTGGACGGCGTGGAAGTGCACAACGCC
AAGACCAAGCCTAGAGAGGAACAGTTCAACAGCACCTACAGAGTGGTGTCCGTG
CTGACAGTGCTGCACCAGGATTGGCTGAACGGCAAAGAGTACAAGTGCAAGGTG
TCCAACAAGGGCCTGCCTAGCAGCATCGAGAAAACCATCAGCAAGGCCAAGGGA
CAGCCCAGGGAACCCCAGGTTTACACACTGCCTCCAAGCCAAGAGGAAATGACC
AAGAATCAGGTGTCCCTGACCTGCCTGGTTAAGGGCTTCTACCCCTCCGATATCG
CCGTGGAATGGGAGAGCAATGGCCAGCCTGAGAACAACTACAAGACAACCCCTC
CTGTGCTGGACAGCGACGGCTCATTCTTCCTGTACAGCAGACTGACCGTGGACAA
GTCCAGATGGCAAGAGGGCAACGTGTTCTCCTGCAGCGTGATGCACGAGGCCCTG
CACAACCACTACACCCAGAAGTCCCTGTCTCTGTCCCTGGGCAAATGATAAGCTT

Fig. 10

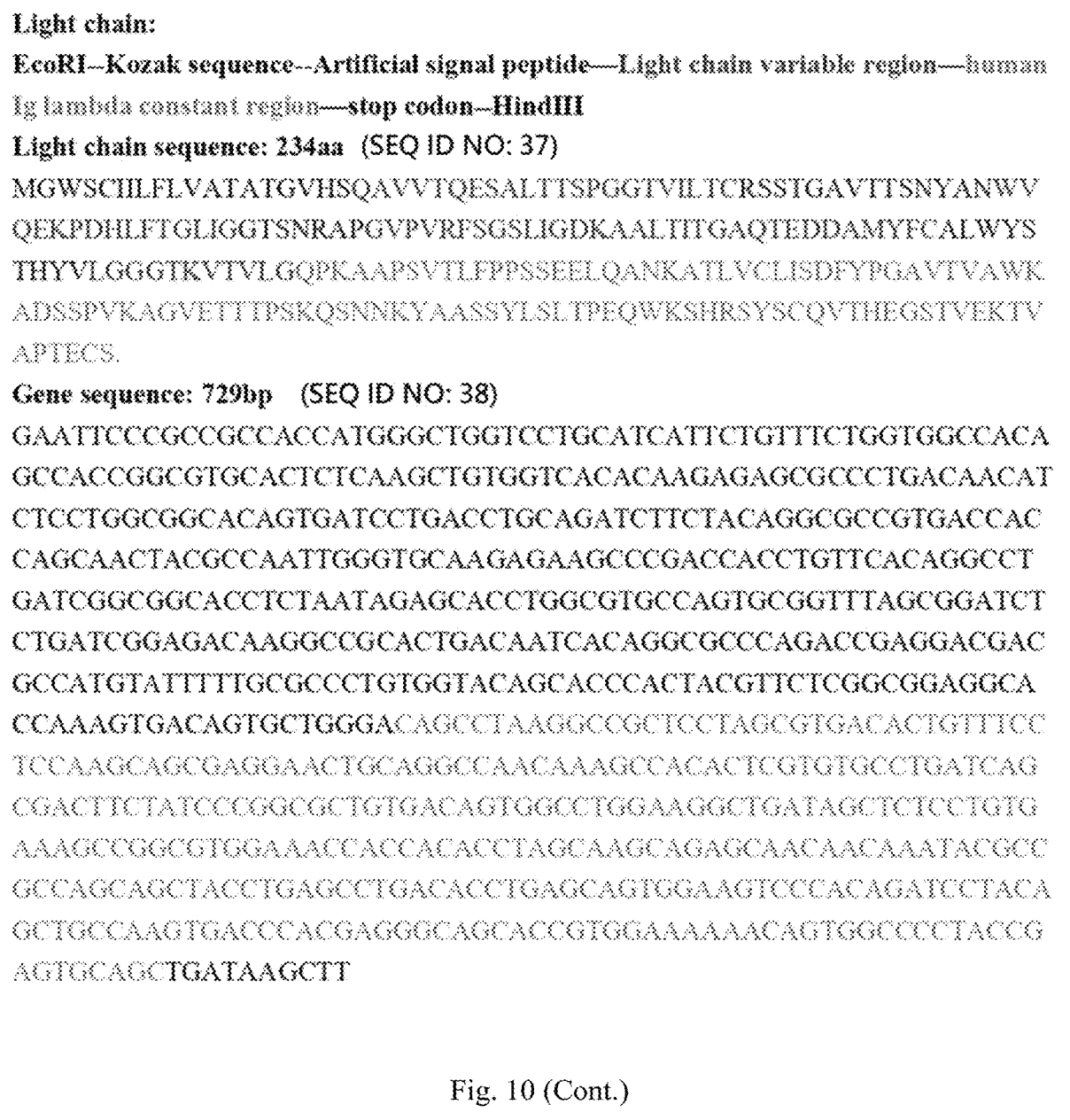

Light chain:

EcoRI--Kozak sequence--Artificial signal peptide—Light chain variable region—human Ig lambda constant region—stop codon--HindIII

Light chain sequence: 234aa (SEQ ID NO: 37)

MGWSCIILFLVATATGVHSQAVVTQESALTTSPGGTVILTCRSSTGAVTTSNYANWV
QEKPDHLFTGLIGGTSNRAPGVPVRFSGSLIGDKAALTITGAQTEDDAMYFCALWYS
THYVLGGGTKVTVLGQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTV
APTECS.

Gene sequence: 729bp (SEQ ID NO: 38)

GAATTCCCGCCGCCACCATGGGCTGGTCCTGCATCATTCTGTTTCTGGTGGCCACA
GCCACCGGCGTGCACTCTCAAGCTGTGGTCACACAAGAGAGCGCCCTGACAACAT
CTCCTGGCGGCACAGTGATCCTGACCTGCAGATCTTCTACAGGCGCCGTGACCAC
CAGCAACTACGCCAATTGGGTGCAAGAGAAGCCCGACCACCTGTTCACAGGCCT
GATCGGCGGCACCTCTAATAGAGCACCTGGCGTGCCAGTGCGGTTTAGCGGATCT
CTGATCGGAGACAAGGCCGCACTGACAATCACAGGCGCCCAGACCGAGGACGAC
GCCATGTATTTTTGCGCCCTGTGGTACAGCACCCACTACGTTCTCGGCGGAGGCA
CCAAAGTGACAGTGCTGGGACAGCCTAAGGCCGCTCCTAGCGTGACACTGTTTCC
TCCAAGCAGCGAGGAACTGCAGGCCAACAAAGCCACACTCGTGTGCCTGATCAG
CGACTTCTATCCCGGCGCTGTGACAGTGGCCTGGAAGGCTGATAGCTCTCCTGTG
AAAGCCGGCGTGGAAACCACCACACCTAGCAAGCAGAGCAACAACAAATACGCC
GCCAGCAGCTACCTGAGCCTGACACCTGAGCAGTGGAAGTCCCACAGATCCTACA
GCTGCCAAGTGACCCACGAGGGCAGCACCGTGGAAAAAACAGTGGCCCCTACCG
AGTGCAGCTGATAAGCTT

Fig. 10 (Cont.)

Amino acid sequence alignment between mouse mono and 2BJM template is shown below, where ' | ' is the chain break and * indicates identical amino acid residues in both sequences.

```
2BJM    EVQLQQSGAELVKPGASVKLSCKASGYTFTS-YWMHWVKQRPGRGLEWIGRI    59  (SEQ ID NO: 39)
Mouse   DVQLQESGPGLVKPSQSLSLTCTVTGYSITSDYAWNWFRQFPGNKLEWMGYT    52  (SEQ ID NO: 40)
        :****:**   ****. *:.*:*.. :**::** *   :*. :* **. ***:*
                                                                    (SEQ ID NO: 41)
2BJM    DPNGGGTKYNEKPKSKATLTVDKPSSI         )SAVYYCARMWYYGTYYFDYWG    119
Mouse   SY-SGSTSYNPSLKSRISITRNTSKNQ        )TATYYCAREVT-TFGYFDYWG     110
        . .*.*.** .:**: ::* :. ..   ::**.*:* **:*.*****    ******  (SEQ ID NO: 42)
                                                                    (SEQ ID NO: 43)
2BJM    QGTTLTVSSQAVVTQESALTTSPGETVTLTCRSSTGAVTTSNYANWVQEKPDHLFTGLIG    179
Mouse   QGTTLTVSSQAVVTQESALTTSPGGTVILTCRSSTGAVTTSNYANWVQEKPDHLFTGLIG    170
        *********************** ** ******************************** (SEQ ID NO: 44)
                                                                    (SEQ ID NO: 45)
2BJM    GTNNRAPGVPARFSGSLIGNKAALTITGAQTEDEAIYFCALWYSNHLVFGGGTKLTVLE    238
Mouse   GTSNRAPGVPVRFSGSLIGDKAALTITGAQTEDDAMYFCALWYSTHYVLGGGTKVTVL     229
        **. *******. *******:**************:*:*******. * *:*****:*** (SEQ ID NO: 46)
```

Fig. 11

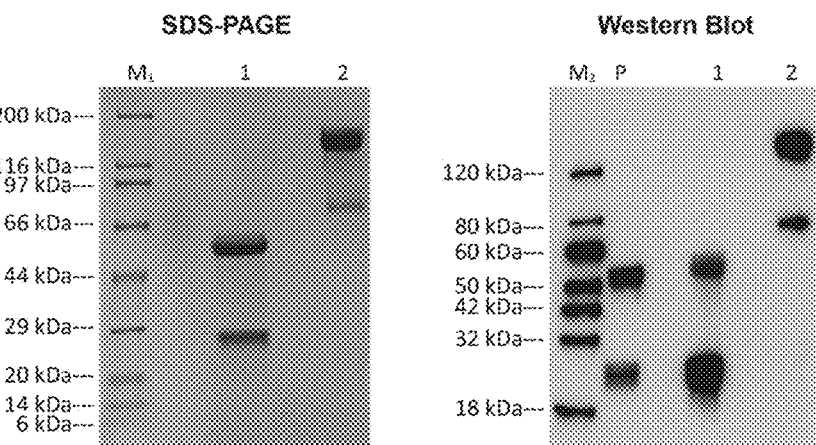

Lane M₁: Protein Marker, TaKaRa, Cat. No. 3452
Lane M₂: Protein Marker, GenScript, Cat. No. M00521
Lane 1: Reducing condition
Lane 2: Non-reducing condition
Lane P: Human IgG1, Kappa (Sigma, Cat.No.I5154) as a positive control
Primary antibody: Goat Anti-Human IgG-HRP (GenScript, Cat. No. A00166)
Primary antibody: Goat Anti-Human Lambda-HRP (SouthernBiotech, Cat. No. 2070-05)

Fig. 12A

Affinity measurement of chimeric antibody

| Ligand | Analyte | $k_a$ (1/Ms) | $k_d$ (1/s) | $KD$ (M) | Rmax | Chi² (RU²) |
|---|---|---|---|---|---|---|
| Chimeric IgG | BSA-Succinic acid | 3.79E+05 | 4.25E-04 | 1.12E-09 | 41.93 | 0.228 |

Fig. 12B

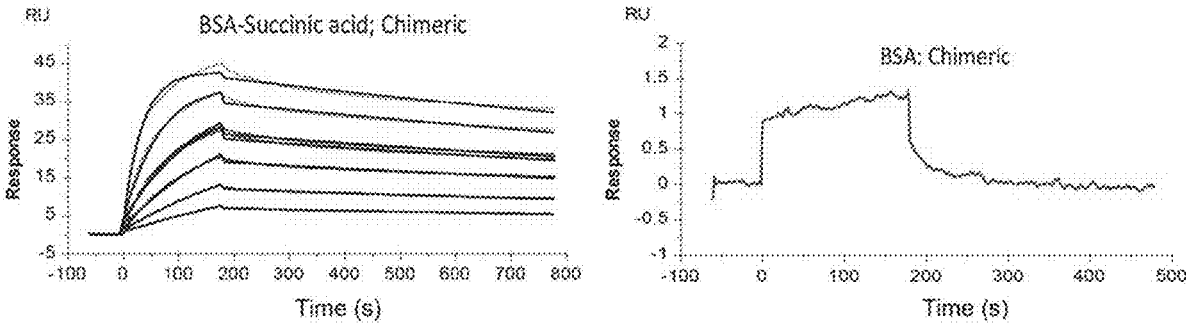

Fig. 12C

Kinetic data of selected humanized antibodies to Ag using Biacore 8K.

| Pair | Capture | Analyte | Chi² (RU²) | ka (1/Ms) | kd (1/s) | KD (M) |
|---|---|---|---|---|---|---|
| VH3+VL2 | 18 | BSA-Succinic Acid | 6.61E-02 | 1.63E+05 | 5.46E-04 | 3.36E-09 |
| VH3+VL3 | 19 | BSA-Succinic Acid | 3.68E-01 | 2.35E+05 | 6.27E-04 | 2.67E-09 |
| VH3+VL5 | 21 | BSA-Succinic Acid | 1.39E+00 | 3.64E+05 | 1.78E-03 | 4.89E-09 |
| VH3+VL6 | 22 | BSA-Succinic Acid | 2.19E-01 | 2.08E+05 | 5.68E-04 | 2.73E-09 |
| VH3+VL7 | 23 | BSA-Succinic Acid | 1.83E+00 | 1.42E+05 | 2.48E-04 | 1.75E-09 |
| VH3+VL8 | 24 | BSA-Succinic Acid | 1.81E+00 | 3.14E+05 | 9.11E-04 | 2.90E-09 |
| VH4+VL2 | 26 | BSA-Succinic Acid | 1.65E+00 | 1.25E+05 | 5.94E-04 | 4.75E-09 |
| VH4+VL3 | 27 | BSA-Succinic Acid | 5.48E-02 | 1.30E+05 | 5.68E-04 | 4.37E-09 |
| VH4+VL6 | 30 | BSA-Succinic Acid | 8.74E-02 | 1.40E+05 | 5.66E-04 | 4.04E-09 |
| VH4+VL7 | 31 | BSA-Succinic Acid | 7.47E-01 | 3.12E+04 | 7.90E-04 | 2.53E-08 |
| VH5+VL2 | 34 | BSA-Succinic Acid | 2.92E+00 | 1.35E+05 | 1.65E-04 | 1.23E-09 |
| VH5+VL3 | 35 | BSA-Succinic Acid | 4.11E-02 | 5.73E+04 | 3.59E-04 | 6.27E-09 |
| VH5+VL4 | 36 | BSA-Succinic Acid | 2.20E+00 | 1.59E+05 | 3.53E-04 | 2.22E-09 |
| VH5+VL5 | 37 | BSA-Succinic Acid | 2.52E+00 | 1.90E+05 | 8.10E-04 | 4.27E-09 |
| VH5+VL6 | 38 | BSA-Succinic Acid | 1.95E-01 | 4.86E+04 | 4.32E-04 | 8.89E-09 |
| VH5+VL8 | 40 | BSA-Succinic Acid | 2.67E+00 | 2.55E+05 | 1.01E-03 | 3.99E-09 |
| chimeric | Ab | BSA-Succinic Acid | 2.39E+00 | 3.59E+05 | 6.84E-04 | 1.91E-09 |
| VH1+VL1 | 1 | BSA-Succinic Acid | 4.22E+05 | 6.75E-02 | 1.60E-07 | 4.22E+05 |
| VH1+VL2 | 2 | BSA-Succinic Acid | 1.18E+06 | 2.62E-03 | 2.22E-09 | 1.18E+06 |
| VH1+VL3 | 3 | BSA-Succinic Acid | 1.13E+06 | 1.51E-03 | 1.33E-09 | 1.13E+06 |
| VH1+VL4 | 4 | BSA-Succinic Acid | 1.91E+05 | 7.73E-04 | 4.06E-09 | 1.91E+05 |
| VH1+VL5 | 5 | BSA-Succinic Acid | 5.89E+04 | 1.08E-03 | 1.84E-08 | 5.89E+04 |
| VH1+VL6 | 6 | BSA-Succinic Acid | 1.42E+05 | 8.02E-04 | 5.63E-09 | 1.42E+05 |
| VH1+VL7 | 7 | BSA-Succinic Acid | 5.61E+05 | 3.11E-04 | 5.55E-10 | 5.61E+05 |
| VH1+VL8 | 8 | BSA-Succinic Acid | 7.25E+05 | 2.19E-03 | 3.02E-09 | 7.25E+05 |
| VH2+VL1 | 9 | BSA-Succinic Acid | 9.66E+03 | 7.31E-06 | 7.57E-10 | 9.66E+03 |
| VH2+VL2 | 10 | BSA-Succinic Acid | 5.36E+02 | 5.43E-04 | 1.01E-06 | 5.36E+02 |
| VH2+VL3 | 11 | BSA-Succinic Acid | 9.37E+01 | 1.19E-03 | 1.27E-05 | 9.37E+01 |
| VH2+VL4 | 12 | BSA-Succinic Acid | 9.22E+04 | 7.04E-05 | 7.64E-10 | 9.22E+04 |
| VH2+VL5 | 13 | BSA-Succinic Acid | 7.52E+03 | 1.17E-05 | 1.55E-09 | 7.52E+03 |
| VH2+VL6 | 14 | BSA-Succinic Acid | 7.45E+03 | 1.65E-05 | 2.22E-09 | 7.45E+03 |
| VH2+VL7 | 15 | BSA-Succinic Acid | 3.15E+03 | 1.16E-05 | 3.69E-09 | 3.15E+03 |
| VH2+VL8 | 16 | BSA-Succinic Acid | 6.63E+03 | 4.50E-04 | 6.79E-08 | 6.63E+03 |
| VH3+VL1 | 17 | BSA-Succinic Acid | 2.79E+04 | 1.03E-03 | 3.67E-08 | 2.79E+04 |
| VH3+VL4 | 20 | BSA-Succinic Acid | 4.14E+04 | 3.10E-04 | 7.48E-09 | 4.14E+04 |
| VH4+VL1 | 25 | BSA-Succinic Acid | 7.07E+02 | 1.50E-03 | 2.12E-06 | 7.07E+02 |
| VH4+VL4 | 28 | BSA-Succinic Acid | 8.30E-01 | 3.10E+03 | 1.22E-03 | 3.94E-07 |
| VH4+VL5 | 29 | BSA-Succinic Acid | 1.08E+00 | 4.33E+03 | 2.40E-04 | 5.54E-08 |
| VH4+VL8 | 32 | BSA-Succinic Acid | 6.02E-01 | 6.96E+03 | 3.05E-05 | 4.38E-09 |
| VH5+VL1 | 33 | BSA-Succinic Acid | 4.48E+00 | 2.50E+03 | 1.18E-03 | 4.74E-07 |
| VH5+VL7 | 39 | BSA-Succinic Acid | 1.32E+01 | 3.07E+03 | 8.62E-07 | 2.81E-10 |

Fig. 13

| Sample | Con.(mg/mL) | Amount(mg) | Purity |
|---|---|---|---|
| VH3+VL3 | 4.846 | 15.02 | 85% |
| VH4+VL2 | 3.698 | 14.05 | 85% |
| VH4+VL3 | 3.902 | 12.10 | 85% |

Affinity measurement of chimeric and humanized antibodies

| Ligand | Analyte | $k_a$ (1/Ms) | $k_d$ (1/s) | KD(M) | Rmax (RU) | Chi² (RU²) |
|---|---|---|---|---|---|---|
| 6G10F6-chim | BSA-Succinic acid | 2.56E+05 | 2.72E-04 | 1.06E-09 | 30 | 1.31E-01 |
| VH3+VL3 | BSA-Succinic acid | 1.51E+05 | 1.78E-04 | 1.18E-09 | 26.5 | 4.94E-02 |
| VH4+VL2 | BSA-Succinic acid | 9.20E+04 | 1.40E-04 | 1.52E-09 | 29.5 | 3.38E-02 |
| VH4+VL3 | BSA-Succinic acid | 8.70E+04 | 1.44E-04 | 1.66E-09 | 24.8 | 1.15E-02 |

| ng/ml | chimeric IgG | | | | | | |
| --- | --- | --- | --- | --- | --- | --- | --- |
| | -80°C | 1 month | | | 2 month | | |
| | | 4°C | 25°C | 40°C | 4°C | 25°C | 40°C |
| 3000 | 3.164 | 3.164 | 3.077 | 3.104 | 3.051 | 3.077 | 2.98 |
| 1000 | 3.11 | 3.11 | 2.99 | 3.044 | 3.026 | 3.061 | 2.905 |
| 333.33 | 2.841 | 2.87 | 2.573 | 2.757 | 2.81 | 2.588 | 2.61 |
| 111.11 | 2.478 | 2.458 | 2.13 | 2.415 | 2.31 | 2.071 | 1.934 |
| 37.04 | 1.445 | 1.531 | 1.298 | 1.445 | 1.429 | 1.296 | 1.037 |
| 12.35 | 0.528 | 0.744 | 0.636 | 0.714 | 0.644 | 0.574 | 0.447 |
| 4.12 | 0.213 | 0.302 | 0.264 | 0.28 | 0.294 | 0.256 | 0.204 |
| 1.37 | 0.093 | 0.131 | 0.118 | 0.137 | 0.129 | 0.129 | 0.1 |
| 0.46 | 0.072 | 0.087 | 0.078 | 0.085 | 0.083 | 0.081 | 0.064 |
| 0.15 | 0.062 | 0.063 | 0.062 | 0.067 | 0.064 | 0.061 | 0.058 |
| 0.05 | 0.051 | 0.055 | 0.053 | 0.058 | 0.054 | 0.055 | 0.051 |
| 0.0167 | 0.052 | 0.054 | 0.052 | 0.055 | 0.051 | 0.053 | 0.051 |

| ng/ml | VH3+VL3 IgG | | | | | | |
|---|---|---|---|---|---|---|---|
| | | 1 month | | | 2 month | | |
| | -80°C | 4°C | 25°C | 40°C | 4°C | 25°C | 40°C |
| 3000 | .047 | .959 | .939 | .245 | .93 | .871 | .996 |
| 1000 | .729 | .041 | .844 | .864 | .895 | .053 | .643 |
| 333.33 | 2.784 | 2.877 | 2.693 | 2.743 | 2.681 | 2.706 | 1.414 |
| 111.11 | 2.277 | 2.337 | 2.266 | 1.859 | 2.285 | 2.142 | 1.499 |
| 37.04 | 1.322 | 1.479 | 1.359 | 0.913 | 1.493 | 1.163 | 0.632 |
| 12.35 | 0.499 | 0.624 | 0.599 | 0.374 | 0.639 | 0.526 | 0.25 |
| 4.12 | 0.205 | 0.235 | 0.212 | 0.153 | 0.244 | 0.206 | 0.113 |
| 1.37 | 0.104 | 0.117 | 0.112 | 0.086 | 0.121 | 0.104 | 0.074 |
| 0.46 | 0.07 | 0.07 | 0.071 | 0.064 | 0.073 | 0.072 | 0.061 |
| 0.15 | 0.062 | 0.058 | 0.059 | 0.057 | 0.066 | 0.058 | 0.052 |
| 0.05 | 0.06 | 0.053 | 0.052 | 0.052 | 0.054 | 0.055 | 0.053 |
| 0.0167 | 0.07 | 0.058 | 0.055 | 0.055 | 0.052 | 0.053 | 0.055 |

| | VH4+VL2 IgG | | | | | | |
| --- | --- | --- | --- | --- | --- | --- | --- |
| | | 1 month | | | 2 month | | |
| ng/ml | -80°C | 4°C | 25°C | 40°C | 4°C | 25°C | 40°C |
| 15857.00 | 2.819 | 2.727 | 2.741 | 2.905 | 2.705 | 2.684 | 2.804 |
| 5285.67 | 2.725 | 2.677 | 2.783 | 2.777 | 2.732 | 2.765 | 2.78 |
| 1761.89 | 2.685 | 2.557 | 2.593 | 2.605 | 2.625 | 2.629 | 2.566 |
| 587.30 | 2.566 | 2.568 | 2.564 | 2.411 | 2.691 | 2.488 | 2.415 |
| 195.77 | 2.33 | 2.282 | 2.203 | 1.827 | 2.25 | 2.124 | 1.899 |
| 65.26 | 1.747 | 1.748 | 1.602 | 1.126 | 1.74 | 1.522 | 0.93 |
| 21.75 | 1.028 | 0.923 | 0.834 | 0.473 | 0.911 | 0.776 | 0.382 |
| 7.25 | 0.429 | 0.402 | 0.338 | 0.196 | 0.381 | 0.348 | 0.169 |
| 2.42 | 0.188 | 0.172 | 0.154 | 0.101 | 0.164 | 0.154 | 0.088 |
| 0.81 | 0.105 | 0.094 | 0.083 | 0.069 | 0.091 | 0.087 | 0.065 |
| 0.27 | 0.07 | 0.088 | 0.058 | 0.054 | 0.062 | 0.064 | 0.053 |
| 0.09 | 0.064 | 0.059 | 0.055 | 0.056 | 0.058 | 0.056 | 0.054 |

| ng/ml | VH4+VL3 IgG | | | | | | |
|---|---|---|---|---|---|---|---|
| | | 1 month | | | 2 month | | |
| | -80°C | 4°C 1 Mon | 25°C 1 Mon | 40°C 1 Mon | 4°C 2 Mon | 25°C 2 Mon | 40°C 2 Mon |
| 3000 | 2.604 | 2.588 | 2.572 | 2.666 | 2.539 | 2.637 | 2.668 |
| 1000 | 2.556 | 2.557 | 2.537 | 2.569 | 2.604 | 2.454 | 2.574 |
| 333.33 | 2.641 | 2.31 | 2.36 | 2.37 | 2.05 | 2.59 | 2.082 |
| 111.11 | 1.728 | 1.861 | 1.681 | 1.435 | 1.934 | 1.722 | 1.259 |
| 37.04 | 1.279 | 1.185 | 0.878 | 0.654 | 1.15 | 0.905 | 0.542 |
| 12.35 | 0.586 | 0.526 | 0.392 | 0.269 | 0.528 | 0.425 | 0.236 |
| 4.12 | 0.234 | 0.227 | 0.166 | 0.124 | 0.222 | 0.173 | 0.107 |
| 1.37 | 0.112 | 0.106 | 0.092 | 0.076 | 0.107 | 0.093 | 0.071 |
| 0.46 | 0.075 | 0.069 | 0.06 | 0.057 | 0.073 | 0.068 | 0.059 |
| 0.15 | 0.06 | 0.056 | 0.051 | 0.053 | 0.059 | 0.055 | 0.051 |
| 0.05 | 0.05 | 0.053 | 0.048 | 0.056 | 0.052 | 0.06 | 0.049 |
| 0.0167 | 0.051 | 0.05 | 0.047 | 0.049 | 0.048 | 0.048 | 0.048 |

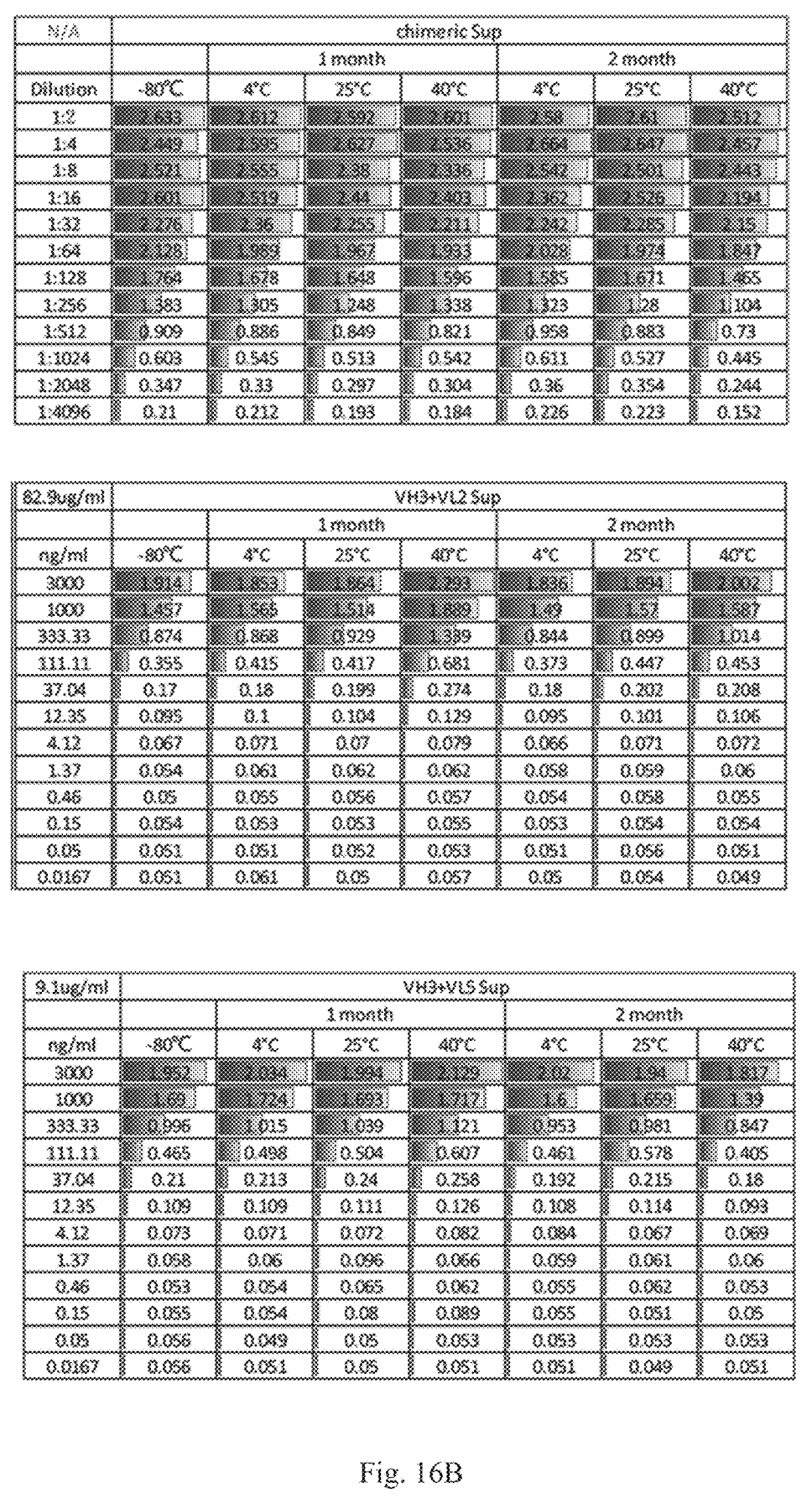

| N/A | chimeric Sup | | | | | | |
| --- | --- | --- | --- | --- | --- | --- | --- |
| | | 1 month | | | 2 month | | |
| Dilution | -80°C | 4°C | 25°C | 40°C | 4°C | 25°C | 40°C |
| 1:2 | | | | | | | |
| 1:4 | | | | | | | |
| 1:8 | | | | | | | |
| 1:16 | | | | | | | |
| 1:32 | | | | | | | |
| 1:64 | | | | | | | |
| 1:128 | .768 | .678 | .648 | .596 | .585 | .671 | .465 |
| 1:256 | 1.383 | 1.305 | 1.248 | 1.338 | 1.323 | 1.28 | 1.104 |
| 1:512 | 0.909 | 0.886 | 0.849 | 0.821 | .958 | 0.883 | 0.73 |
| 1:1024 | 0.603 | 0.545 | 0.513 | 0.542 | 0.611 | 0.527 | 0.445 |
| 1:2048 | 0.347 | 0.33 | 0.297 | 0.304 | 0.36 | 0.354 | 0.244 |
| 1:4096 | 0.21 | 0.212 | 0.193 | 0.184 | 0.226 | 0.223 | 0.152 |

| 82.9ug/ml | VH3+VL2 Sup | | | | | | |
| --- | --- | --- | --- | --- | --- | --- | --- |
| | | 1 month | | | 2 month | | |
| ng/ml | -80°C | 4°C | 25°C | 40°C | 4°C | 25°C | 40°C |
| 3000 | | | | | | | |
| 1000 | | | | | | | |
| 333.33 | .874 | 0.868 | 0.929 | 1.399 | 0.844 | .899 | 1.014 |
| 111.11 | 0.355 | 0.415 | 0.417 | 0.681 | 0.373 | 0.447 | 0.453 |
| 37.04 | 0.17 | 0.18 | 0.199 | 0.274 | 0.18 | 0.202 | 0.208 |
| 12.35 | 0.095 | 0.1 | 0.104 | 0.129 | 0.095 | 0.101 | 0.106 |
| 4.12 | 0.067 | 0.071 | 0.07 | 0.079 | 0.066 | 0.071 | 0.072 |
| 1.37 | 0.054 | 0.061 | 0.062 | 0.062 | 0.058 | 0.059 | 0.06 |
| 0.46 | 0.05 | 0.055 | 0.056 | 0.057 | 0.054 | 0.058 | 0.055 |
| 0.15 | 0.054 | 0.053 | 0.053 | 0.055 | 0.053 | 0.054 | 0.054 |
| 0.05 | 0.051 | 0.051 | 0.052 | 0.053 | 0.051 | 0.056 | 0.051 |
| 0.0167 | 0.051 | 0.061 | 0.05 | 0.057 | 0.05 | 0.054 | 0.049 |

| 9.1ug/ml | VH3+VL5 Sup | | | | | | |
| --- | --- | --- | --- | --- | --- | --- | --- |
| | | 1 month | | | 2 month | | |
| ng/ml | -80°C | 4°C | 25°C | 40°C | 4°C | 25°C | 40°C |
| 3000 | | | | | | | |
| 1000 | | | | | | | |
| 333.33 | .996 | 1.015 | 1.039 | 1.121 | 0.953 | .881 | .847 |
| 111.11 | 0.465 | 0.498 | 0.504 | 0.607 | 0.461 | 0.578 | 0.405 |
| 37.04 | 0.21 | 0.213 | 0.24 | 0.258 | 0.192 | 0.215 | 0.18 |
| 12.35 | 0.109 | 0.109 | 0.111 | 0.126 | 0.108 | 0.114 | 0.093 |
| 4.12 | 0.073 | 0.071 | 0.072 | 0.082 | 0.084 | 0.067 | 0.069 |
| 1.37 | 0.058 | 0.06 | 0.096 | 0.066 | 0.059 | 0.061 | 0.06 |
| 0.46 | 0.053 | 0.054 | 0.065 | 0.062 | 0.055 | 0.062 | 0.053 |
| 0.15 | 0.055 | 0.054 | 0.08 | 0.089 | 0.055 | 0.051 | 0.05 |
| 0.05 | 0.056 | 0.049 | 0.05 | 0.053 | 0.053 | 0.053 | 0.053 |
| 0.0167 | 0.056 | 0.051 | 0.05 | 0.051 | 0.051 | 0.049 | 0.051 |

Fig. 16B

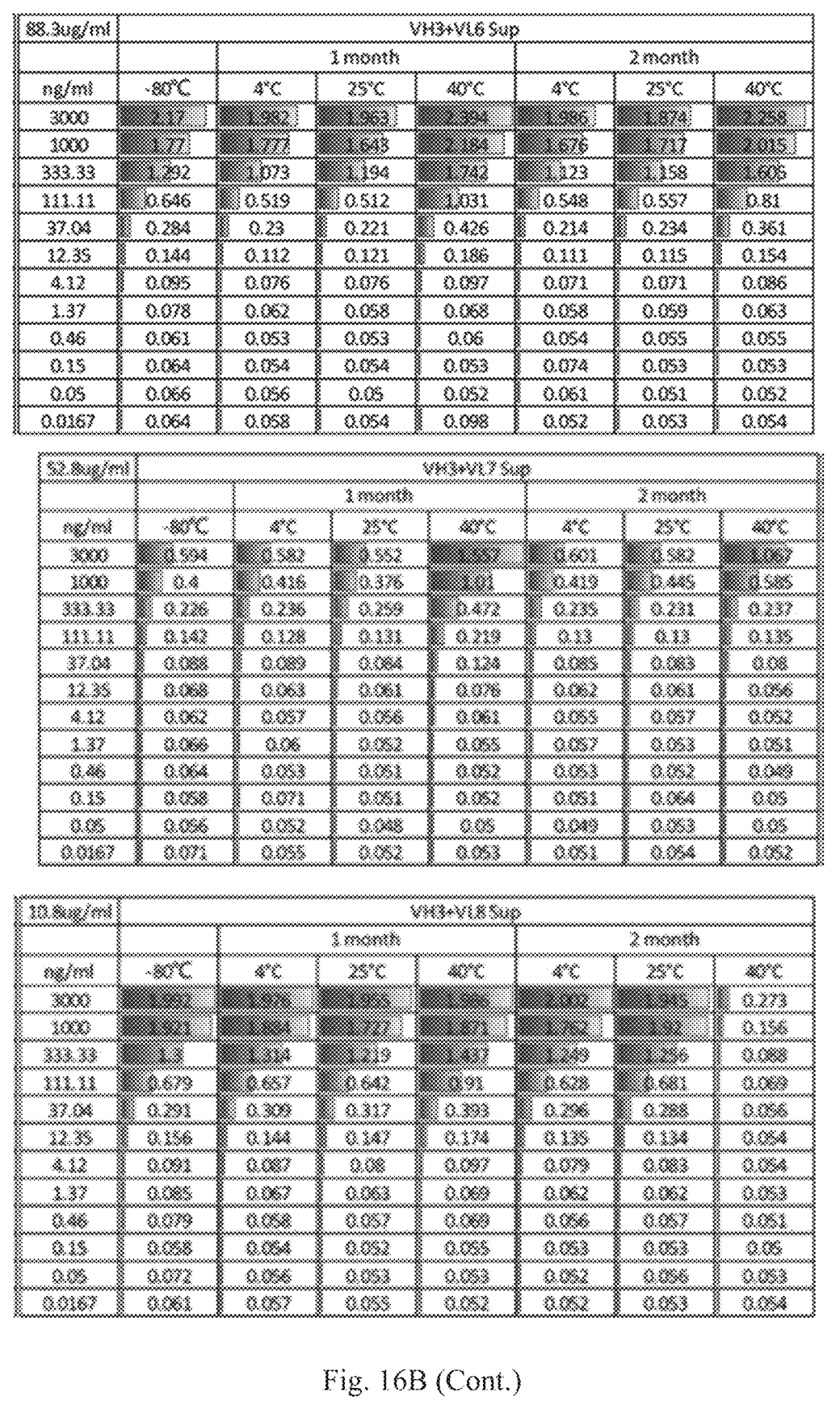

| 88.3ug/ml | VH3+VL6 Sup | | | | | | |
|---|---|---|---|---|---|---|---|
| | | 1 month | | | 2 month | | |
| ng/ml | -80°C | 4°C | 25°C | 40°C | 4°C | 25°C | 40°C |
| 3000 | 1.17 | 1.862 | 1.963 | 1.994 | 1.86 | 1.874 | 0.258 |
| 1000 | 1.77 | 1.777 | 1.643 | 1.94 | 1.676 | 1.717 | 1.015 |
| 333.33 | 1.292 | 1.073 | 1.194 | 1.742 | 1.123 | 1.158 | 1.605 |
| 111.11 | 0.646 | 0.519 | 0.512 | 1.031 | 0.548 | 0.557 | 0.81 |
| 37.04 | 0.284 | 0.23 | 0.221 | 0.426 | 0.214 | 0.234 | 0.361 |
| 12.35 | 0.144 | 0.112 | 0.121 | 0.186 | 0.111 | 0.115 | 0.154 |
| 4.12 | 0.095 | 0.076 | 0.076 | 0.097 | 0.071 | 0.071 | 0.086 |
| 1.37 | 0.078 | 0.062 | 0.058 | 0.068 | 0.058 | 0.059 | 0.063 |
| 0.46 | 0.061 | 0.053 | 0.053 | 0.06 | 0.054 | 0.055 | 0.055 |
| 0.15 | 0.064 | 0.054 | 0.054 | 0.053 | 0.074 | 0.053 | 0.053 |
| 0.05 | 0.066 | 0.056 | 0.05 | 0.052 | 0.061 | 0.051 | 0.052 |
| 0.0167 | 0.064 | 0.058 | 0.054 | 0.098 | 0.052 | 0.053 | 0.054 |

| 52.8ug/ml | VH3+VL7 Sup | | | | | | |
|---|---|---|---|---|---|---|---|
| | | 1 month | | | 2 month | | |
| ng/ml | -80°C | 4°C | 25°C | 40°C | 4°C | 25°C | 40°C |
| 3000 | 0.594 | 0.582 | 0.552 | 0.7 | 0.601 | 0.582 | 0.667 |
| 1000 | 0.4 | 0.416 | 0.376 | 0.601 | 0.419 | 0.445 | 0.585 |
| 333.33 | 0.226 | 0.236 | 0.259 | 0.472 | 0.235 | 0.231 | 0.237 |
| 111.11 | 0.142 | 0.128 | 0.131 | 0.219 | 0.13 | 0.13 | 0.135 |
| 37.04 | 0.088 | 0.089 | 0.084 | 0.134 | 0.085 | 0.083 | 0.08 |
| 12.35 | 0.068 | 0.063 | 0.061 | 0.076 | 0.062 | 0.061 | 0.056 |
| 4.12 | 0.062 | 0.057 | 0.056 | 0.061 | 0.055 | 0.057 | 0.052 |
| 1.37 | 0.066 | 0.06 | 0.052 | 0.055 | 0.057 | 0.053 | 0.051 |
| 0.46 | 0.064 | 0.053 | 0.051 | 0.052 | 0.053 | 0.052 | 0.049 |
| 0.15 | 0.058 | 0.071 | 0.051 | 0.052 | 0.051 | 0.064 | 0.05 |
| 0.05 | 0.056 | 0.052 | 0.048 | 0.05 | 0.049 | 0.053 | 0.05 |
| 0.0167 | 0.071 | 0.055 | 0.052 | 0.053 | 0.051 | 0.054 | 0.052 |

| 10.8ug/ml | VH3+VL8 Sup | | | | | | |
|---|---|---|---|---|---|---|---|
| | | 1 month | | | 2 month | | |
| ng/ml | -80°C | 4°C | 25°C | 40°C | 4°C | 25°C | 40°C |
| 3000 | | | | | | | 0.273 |
| 1000 | | | | | | | 0.156 |
| 333.33 | | | | | | | 0.088 |
| 111.11 | 0.679 | 0.657 | 0.642 | 0.91 | 0.628 | 0.641 | 0.069 |
| 37.04 | 0.291 | 0.309 | 0.317 | 0.393 | 0.296 | 0.288 | 0.056 |
| 12.35 | 0.156 | 0.144 | 0.147 | 0.174 | 0.135 | 0.134 | 0.054 |
| 4.12 | 0.091 | 0.087 | 0.08 | 0.097 | 0.079 | 0.083 | 0.054 |
| 1.37 | 0.085 | 0.067 | 0.063 | 0.069 | 0.062 | 0.062 | 0.053 |
| 0.46 | 0.079 | 0.058 | 0.057 | 0.069 | 0.056 | 0.057 | 0.051 |
| 0.15 | 0.058 | 0.064 | 0.052 | 0.055 | 0.053 | 0.053 | 0.06 |
| 0.05 | 0.072 | 0.056 | 0.053 | 0.053 | 0.052 | 0.056 | 0.053 |
| 0.0167 | 0.061 | 0.057 | 0.055 | 0.052 | 0.052 | 0.053 | 0.054 |

Fig. 16B (Cont.)

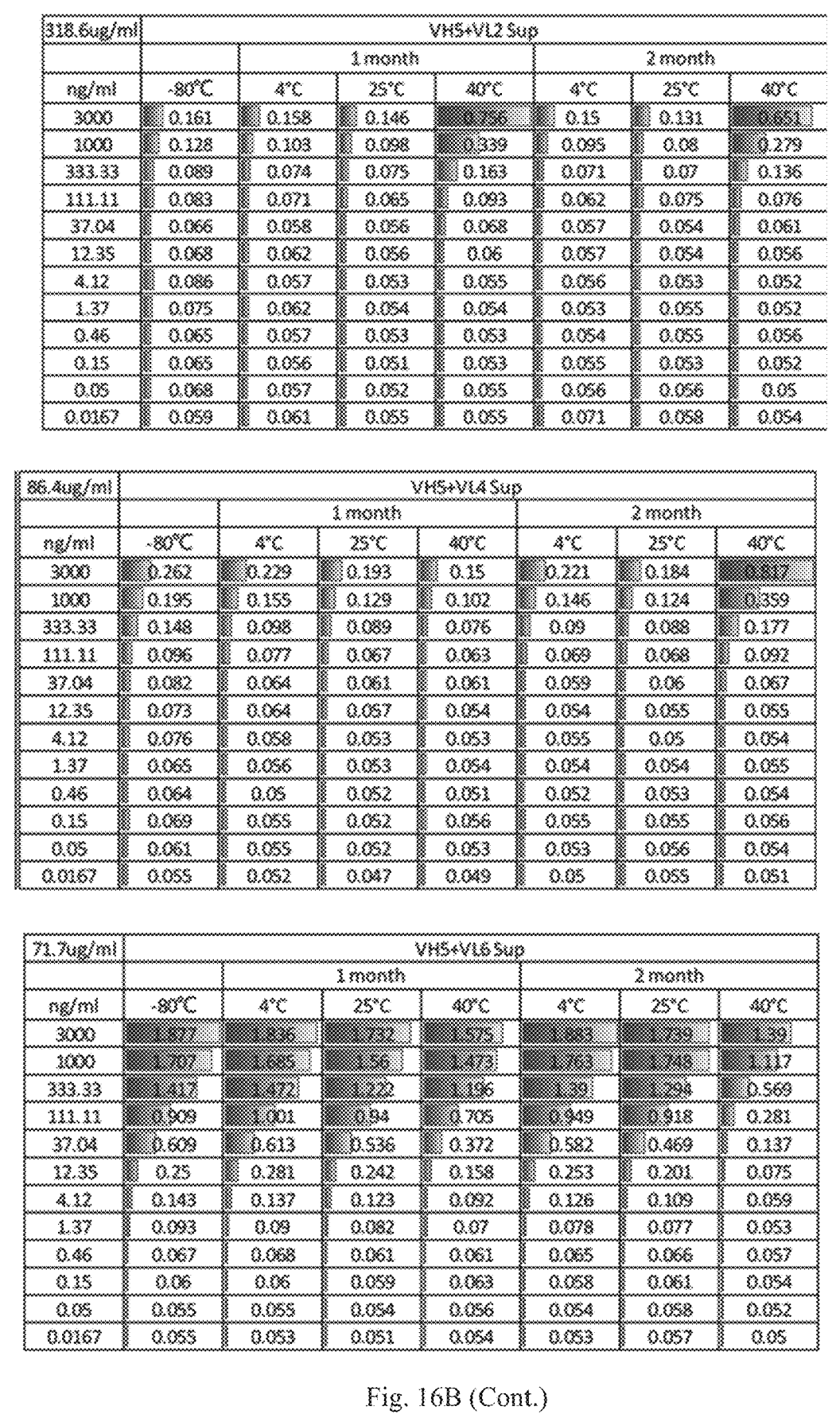

| 318.6ug/ml | VH5+VL2 Sup | | | | | | |
|---|---|---|---|---|---|---|---|
| | | 1 month | | | 2 month | | |
| ng/ml | -80°C | 4°C | 25°C | 40°C | 4°C | 25°C | 40°C |
| 3000 | 0.161 | 0.158 | 0.146 | 0.156 | 0.15 | 0.131 | 0.651 |
| 1000 | 0.128 | 0.103 | 0.098 | 0.339 | 0.095 | 0.08 | 0.279 |
| 333.33 | 0.089 | 0.074 | 0.075 | 0.163 | 0.071 | 0.07 | 0.136 |
| 111.11 | 0.083 | 0.071 | 0.065 | 0.093 | 0.062 | 0.075 | 0.076 |
| 37.04 | 0.066 | 0.058 | 0.056 | 0.068 | 0.057 | 0.054 | 0.061 |
| 12.35 | 0.068 | 0.062 | 0.056 | 0.06 | 0.057 | 0.054 | 0.056 |
| 4.12 | 0.086 | 0.057 | 0.053 | 0.055 | 0.056 | 0.053 | 0.052 |
| 1.37 | 0.075 | 0.062 | 0.054 | 0.054 | 0.053 | 0.055 | 0.052 |
| 0.46 | 0.065 | 0.057 | 0.053 | 0.053 | 0.054 | 0.055 | 0.056 |
| 0.15 | 0.065 | 0.056 | 0.051 | 0.053 | 0.055 | 0.053 | 0.052 |
| 0.05 | 0.068 | 0.057 | 0.052 | 0.055 | 0.056 | 0.056 | 0.05 |
| 0.0167 | 0.059 | 0.061 | 0.055 | 0.055 | 0.071 | 0.058 | 0.054 |

| 86.4ug/ml | VH5+VL4 Sup | | | | | | |
|---|---|---|---|---|---|---|---|
| | | 1 month | | | 2 month | | |
| ng/ml | -80°C | 4°C | 25°C | 40°C | 4°C | 25°C | 40°C |
| 3000 | 0.262 | 0.229 | 0.193 | 0.15 | 0.221 | 0.184 | 0.817 |
| 1000 | 0.195 | 0.155 | 0.129 | 0.102 | 0.146 | 0.124 | 0.359 |
| 333.33 | 0.148 | 0.098 | 0.089 | 0.076 | 0.09 | 0.088 | 0.177 |
| 111.11 | 0.096 | 0.077 | 0.067 | 0.063 | 0.069 | 0.068 | 0.092 |
| 37.04 | 0.082 | 0.064 | 0.061 | 0.061 | 0.059 | 0.06 | 0.067 |
| 12.35 | 0.073 | 0.064 | 0.057 | 0.054 | 0.054 | 0.055 | 0.055 |
| 4.12 | 0.076 | 0.058 | 0.053 | 0.053 | 0.055 | 0.05 | 0.054 |
| 1.37 | 0.065 | 0.056 | 0.053 | 0.054 | 0.054 | 0.054 | 0.055 |
| 0.46 | 0.064 | 0.05 | 0.052 | 0.051 | 0.052 | 0.053 | 0.054 |
| 0.15 | 0.069 | 0.055 | 0.052 | 0.056 | 0.055 | 0.055 | 0.056 |
| 0.05 | 0.061 | 0.055 | 0.052 | 0.053 | 0.053 | 0.056 | 0.054 |
| 0.0167 | 0.055 | 0.052 | 0.047 | 0.049 | 0.05 | 0.055 | 0.051 |

| 71.7ug/ml | VH5+VL6 Sup | | | | | | |
|---|---|---|---|---|---|---|---|
| | | 1 month | | | 2 month | | |
| ng/ml | -80°C | 4°C | 25°C | 40°C | 4°C | 25°C | 40°C |
| 3000 | | | | | | | |
| 1000 | | | | | | | 1.117 |
| 333.33 | | | | | | | 0.569 |
| 111.11 | 0.909 | 1.001 | 0.94 | 0.705 | 0.949 | 0.918 | 0.281 |
| 37.04 | 0.609 | 0.613 | 0.536 | 0.372 | 0.582 | 0.469 | 0.137 |
| 12.35 | 0.25 | 0.281 | 0.242 | 0.158 | 0.253 | 0.201 | 0.075 |
| 4.12 | 0.143 | 0.137 | 0.123 | 0.092 | 0.126 | 0.109 | 0.059 |
| 1.37 | 0.093 | 0.09 | 0.082 | 0.07 | 0.078 | 0.077 | 0.053 |
| 0.46 | 0.067 | 0.068 | 0.061 | 0.061 | 0.065 | 0.066 | 0.057 |
| 0.15 | 0.06 | 0.06 | 0.059 | 0.063 | 0.058 | 0.061 | 0.054 |
| 0.05 | 0.055 | 0.055 | 0.054 | 0.056 | 0.054 | 0.058 | 0.052 |
| 0.0167 | 0.055 | 0.053 | 0.051 | 0.054 | 0.053 | 0.057 | 0.05 |

Fig. 16B (Cont.)

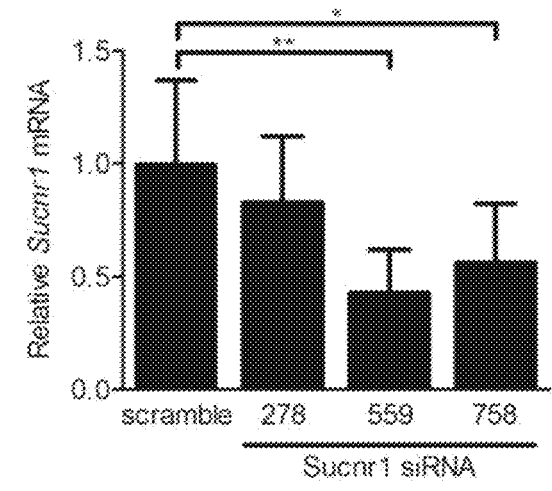
Fig. 17A
Fig. 17B
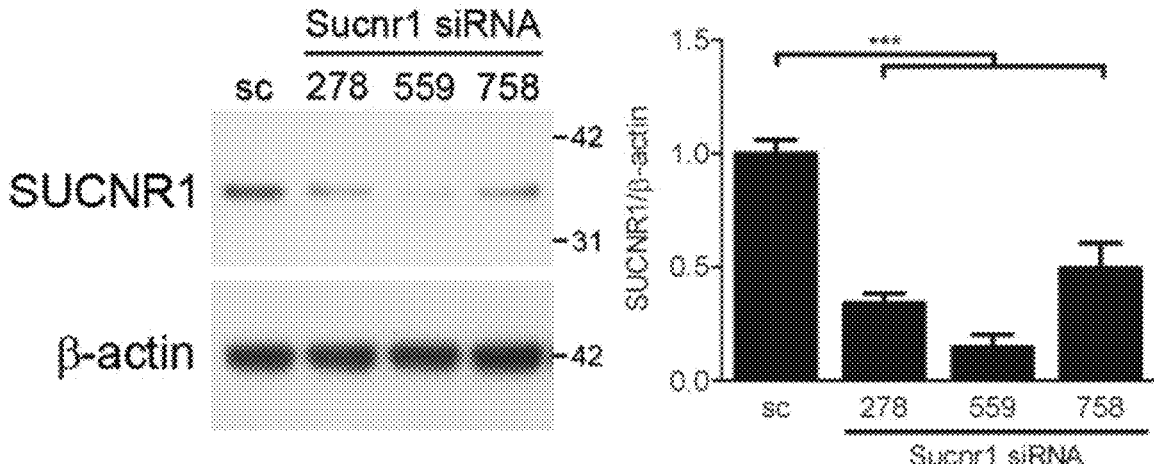
Fig. 17C

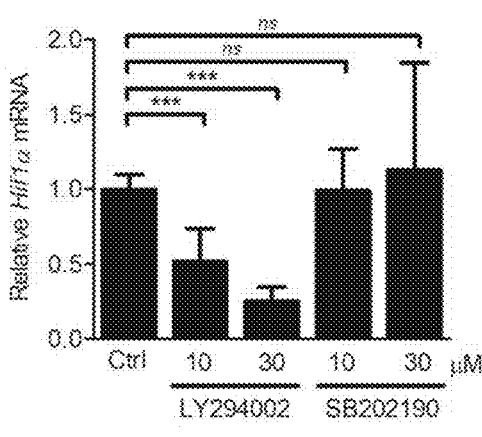
Fig. 25C
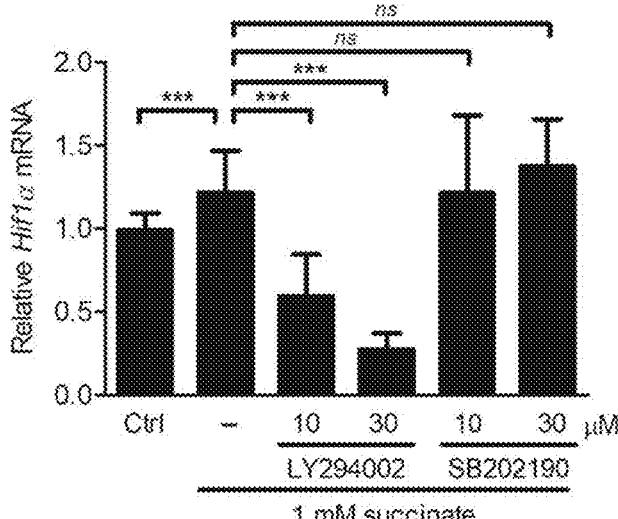
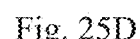
Fig. 25D
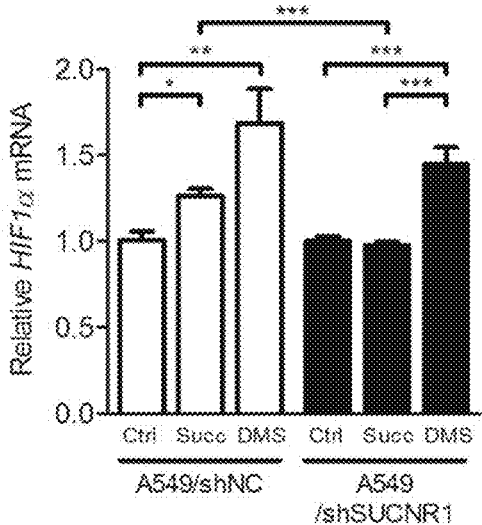
Fig. 25E

Lung metastatic nodules

SEQUENCE LISTING

```
<160> NUMBER OF SEQ ID NOS: 34

<210> SEQ ID NO 1
<211> LENGTH: 411
<212> TYPE: DNA
<213> ORGANISM: Artificial Sequence
<220> FEATURE:
<223> OTHER INFORMATION: Heavy chain of 6G10F6 Antibody

<400> SEQUENCE: 1
atgagagtgc tgattctttt gtggctgttc acagcctttc ctggtatcct gtctgatgtg        60
cagcttcagg agtcgggacc tggcctggtg aaaccttctc agtctctgtc cctcacctgc       120
actgtcactg gctactcaat caccagtgat tatgcctgga actggttccg gcagtttcca       180
ggaaacaaac tggagtggat gggctacaca agctacagtg gtagcactag ctataaccca       240
tctctcaaaa gtcgaatctc tatcactcga aacacatcca agaaccagat cttcctgcag       300
ttgaattctg tgactcctga ggacacagcc acatattact gtgcaagaga ggttactacg       360
tttggatact tgactactg gggccaaggc accactctca cagtctcctc a               411

<210> SEQ ID NO 2
<211> LENGTH: 137
<212> TYPE: PRT
<213> ORGANISM: Artificial Sequence
<220> FEATURE:
<223> OTHER INFORMATION: Heavy chain of 6G10F6 Antibody

<400> SEQUENCE: 2

Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
                20                  25                  30

Ser Gln Ser Leu Ser Leu Thr Cys Thr Val Thr Gly Tyr Ser Ile Thr
            35                  40                  45

Ser Asp Tyr Ala Trp Asn Trp Phe Arg Gln Phe Pro Gly Asn Lys Leu
        50                  55                  60

Glu Trp Met Gly Tyr Thr Ser Tyr Ser Gly Ser Thr Ser Tyr Asn Pro
65                  70                  75                  80

Ser Leu Lys Ser Arg Ile Ser Ile Thr Arg Asn Thr Ser Lys Asn Gln
                85                  90                  95

Ile Phe Leu Gln Leu Asn Ser Val Thr Pro Glu Asp Thr Ala Thr Tyr
            100                 105                 110

Tyr Cys Ala Arg Glu Val Thr Thr Phe Gly Tyr Phe Asp Tyr Trp Gly
        115                 120                 125

Gln Gly Thr Thr Leu Thr Val Ser Ser
    130                 135
```

```
<210> SEQ ID NO 3
<211> LENGTH: 384
<212> TYPE: DNA
<213> ORGANISM: Artificial Sequence
<220> FEATURE:
<223> OTHER INFORMATION: Light chain of 6G10F6 antibody

<400> SEQUENCE: 3
atggcctgga cttcacttat actctctctc ctggctctct gctcaggagc cagttcccag        60
gctgttgtga ctcaggaatc tgcactcacc acatcacctg gtggaacagt catactcact       120
tgtcgctcaa gtactggggc tgttacaact agtaactatg ccaactgggt ccaagaaaaa       180
ccagatcatt tattcactgg tctaataggt ggtaccagca accgagctcc aggtgttcct       240
gtcagattct caggctccct gattggagac aaggctgccc tcaccatcac aggggcacag       300
actgaggatg atgcaatgta tttctgtgct ctatggtaca gcacccatta tgttctcggc       360
ggtggaacca aggtcactgt ccta                                              384

<210> SEQ ID NO 4
<211> LENGTH: 128
<212> TYPE: PRT
<213> ORGANISM: Artificial Sequence
<220> FEATURE:
<223> OTHER INFORMATION: Light chain of 6G10F6 antibody

<400> SEQUENCE: 4

Met Ala Trp Thr Ser Leu Ile Leu Ser Leu Leu Ala Leu Cys Ser Gly
1               5                   10                  15

Ala Ser Ser Gln Ala Val Val Thr Gln Glu Ser Ala Leu Thr Thr Ser
            20                  25                  30

Pro Gly Gly Thr Val Ile Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Ser Asn Arg Ala Pro Gly Val Pro
65                  70                  75                  80

Val Arg Phe Ser Gly Ser Leu Ile Gly Asp Lys Ala Ala Leu Thr Ile
                85                  90                  95

Thr Gly Ala Gln Thr Glu Asp Asp Ala Met Tyr Phe Cys Ala Leu Trp
            100                 105                 110

Tyr Ser Thr His Tyr Val Leu Gly Gly Gly Thr Lys Val Thr Val Leu
        115                 120                 125

<210> SEQ ID NO 5
<211> LENGTH: 411
<212> TYPE: DNA
<213> ORGANISM: Artificial Sequence
<220> FEATURE:
<223> OTHER INFORMATION: Heavy chain of 6G10G5 antibody

<400> SEQUENCE: 5
atgagagtgc tgattctttt gtggctgttc acagcctttc ctggtatcct gtctgatgtg        60
cagcttcagg agtcgggacc tggcctggtg aaaccttctc agtctctgtc cctcacctgc       120
actgtcactg ctactcaat accagtgat tatgcctgga actggttccg gcagtttcca         180
ggaaacaaac tggagtggat gggctacaca agctacagtg gtagcactag ctataaccca       240
tctctcaaaa gtcgaatctc tatcactcga aacacatcca agaaccagat cttcctgcag       300
```

-continued

--- ttgaattctg tgactcctga ggacacagcc acatattact gtgcaagaga ggttactacg          360
tttggatact ttgactactg gggccaaggc accactctca cagtctcctc a                   411

<210> SEQ ID NO 6
<211> LENGTH: 137
<212> TYPE: PRT
<213> ORGANISM: Artificial Sequence
<220> FEATURE:
<223> OTHER INFORMATION: Heavy chain of 6G10G5 antibody

<400> SEQUENCE: 6

Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Thr Val Thr Gly Tyr Ser Ile Thr
        35                  40                  45

Ser Asp Tyr Ala Trp Asn Trp Phe Arg Gln Phe Pro Gly Asn Lys Leu
    50                  55                  60

Glu Trp Met Gly Tyr Thr Ser Tyr Ser Gly Ser Thr Ser Tyr Asn Pro
65                  70                  75                  80

Ser Leu Lys Ser Arg Ile Ser Ile Thr Arg Asn Thr Ser Lys Asn Gln
                85                  90                  95

Ile Phe Leu Gln Leu Asn Ser Val Thr Pro Glu Asp Thr Ala Thr Tyr
            100                 105                 110

Tyr Cys Ala Arg Glu Val Thr Thr Phe Gly Tyr Phe Asp Tyr Trp Gly
        115                 120                 125

Gln Gly Thr Thr Leu Thr Val Ser Ser
    130                 135

<210> SEQ ID NO 7
<211> LENGTH: 384
<212> TYPE: DNA
<213> ORGANISM: Artificial Sequence
<220> FEATURE:
<223> OTHER INFORMATION: Light chain of 6G10G5 antibody

<400> SEQUENCE: 7
atggcctgga cttcacttat actctctctc ctggctctct gctcaggagc cagttcccag          60
gctgttgtga ctcaggaatc tgcactcacc acatcacctg gtggaacagt catactcact          120
tgtcgctcaa gtactggggc tgttacaact agtaactatg ccaactgggt ccaagaaaaa          180
ccagatcatt tattcactgg tctaataggt ggtaccagca accgagctcc aggtgttcct          240
gtcagattct caggctccct gattggagac aaggctgccc tcaccatcac aggggcacag          300
actgaggatg atgcaatgta tttctgtgct ctatggtaca gcaccccatta tgttctcggc          360 ggtggaacca aggtcactgt ccta                                                  384

<210> SEQ ID NO 8
<211> LENGTH: 128
<212> TYPE: PRT
<213> ORGANISM: Artificial Sequence
<220> FEATURE:
<223> OTHER INFORMATION: Light chain of 6G10G5 antibody

<400> SEQUENCE: 8

Met Ala Trp Thr Ser Leu Ile Leu Ser Leu Leu Ala Leu Cys Ser Gly
1               5                   10                  15

Ala Ser Ser Gln Ala Val Val Thr Gln Glu Ser Ala Leu Thr Thr Ser

-continued

```
                20                  25                  30
Pro Gly Gly Thr Val Ile Leu Thr Cys Arg Ser Ser Thr Gly Ala Val
            35                  40                  45

Thr Thr Ser Asn Tyr Ala Asn Trp Val Gln Glu Lys Pro Asp His Leu
        50                  55                  60

Phe Thr Gly Leu Ile Gly Gly Thr Ser Asn Arg Ala Pro Gly Val Pro
65                  70                  75                  80

Val Arg Phe Ser Gly Ser Leu Ile Gly Asp Lys Ala Ala Leu Thr Ile
                85                  90                  95

Thr Gly Ala Gln Thr Glu Asp Asp Ala Met Tyr Phe Cys Ala Leu Trp
            100                 105                 110

Tyr Ser Thr His Tyr Val Leu Gly Gly Gly Thr Lys Val Thr Val Leu
            115                 120                 125

<210> SEQ ID NO 9
<211> LENGTH: 465
<212> TYPE: PRT
<213> ORGANISM: Artificial Sequence
<220> FEATURE:
<223> OTHER INFORMATION: VH1 of the humanized 6G10F6 antibody

<400> SEQUENCE: 9

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
                20                  25                  30

Pro Ser Gln Thr Leu Ser Leu Thr Cys Thr Val Ser Gly Tyr Ser Ile
            35                  40                  45

Thr Ser Asp Tyr Ala Trp Asn Trp Ile Arg Gln Pro Pro Gly Lys Gly
        50                  55                  60

Leu Glu Trp Ile Gly Tyr Thr Ser Tyr Ser Gly Ser Thr Ser Tyr Asn
65                  70                  75                  80

Pro Ser Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Glu Val Thr Thr Phe Gly Tyr Phe Asp Tyr Trp
            115                 120                 125

Gly Gln Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
            195                 200                 205

Val Pro Ser Ser Ser Leu Gly Thr Lys Thr Tyr Thr Cys Asn Val Asp
        210                 215                 220

His Lys Pro Ser Asn Thr Lys Val Asp Lys Arg Val Glu Ser Lys Tyr
225                 230                 235                 240

Gly Pro Pro Cys Pro Ser Cys Pro Ala Pro Glu Phe Leu Gly Gly Pro
                245                 250                 255

Ser Val Phe Leu Phe Pro Pro Lys Pro Lys Asp Thr Leu Met Ile Ser
```

-continued

```
                 260              265                270
Arg Thr Pro Glu Val Thr Cys Val Val Val Asp Val Ser Gln Glu Asp
        275              280                285

Pro Glu Val Gln Phe Asn Trp Tyr Val Asp Gly Val Glu Val His Asn
    290              295                300

Ala Lys Thr Lys Pro Arg Glu Glu Gln Phe Asn Ser Thr Tyr Arg Val
305              310                315                320

Val Ser Val Leu Thr Val Leu His Gln Asp Trp Leu Asn Gly Lys Glu
                325              330                335

Tyr Lys Cys Lys Val Ser Asn Lys Gly Leu Pro Ser Ser Ile Glu Lys
            340              345                350

Thr Ile Ser Lys Ala Lys Gly Gln Pro Arg Glu Pro Gln Val Tyr Thr
            355              360                365

Leu Pro Pro Ser Gln Glu Glu Met Thr Lys Asn Gln Val Ser Leu Thr
    370              375                380

Cys Leu Val Lys Gly Phe Tyr Pro Ser Asp Ile Ala Val Glu Trp Glu
385              390                395                400

Ser Asn Gly Gln Pro Glu Asn Asn Tyr Lys Thr Thr Pro Pro Val Leu
                405              410                415

Asp Ser Asp Gly Ser Phe Phe Leu Tyr Ser Arg Leu Thr Val Asp Lys
                420              425                430

Ser Arg Trp Gln Glu Gly Asn Val Phe Ser Cys Ser Val Met His Glu
            435              440                445

Ala Leu His Asn His Tyr Thr Gln Lys Ser Leu Ser Leu Ser Leu Gly
    450              455                460

Lys
465
```

```
<210> SEQ ID NO 10
<211> LENGTH: 465
<212> TYPE: PRT
<213> ORGANISM: Artificial Sequence
<220> FEATURE:
<223> OTHER INFORMATION: VH2 of the humanized 6G10F6 antibody

<400> SEQUENCE: 10

Met Gly Trp Ser Cys Ile Ile Leu Phe Leu Val Ala Thr Ala Thr Gly
1               5                10                15

Val His Ser Gln Val Gln Leu Gln Glu Ser Gly Pro Gly Leu Val Lys
                20              25                30

Pro Ser Gln Thr Leu Ser Leu Thr Cys Thr Val Ser Gly Tyr Ser Ile
        35              40                45

Thr Ser Asp Tyr Ala Trp Asn Trp Ile Arg Gln Pro Pro Gly Lys Gly
    50              55                60

Leu Glu Trp Ile Gly Tyr Thr Ser Tyr Ser Gly Ser Thr Ser Tyr Asn
65              70                75                80

Pro Ser Leu Lys Ser Arg Val Thr Ile Ser Arg Asp Thr Ser Lys Asn
                85              90                95

Gln Phe Phe Leu Lys Leu Ser Ser Val Thr Ala Ala Asp Thr Ala Val
            100              105                110

Tyr Tyr Cys Ala Arg Glu Val Thr Thr Phe Gly Tyr Phe Asp Tyr Trp
        115              120                125

Gly Gln Gly Thr Leu Val Thr Val Ser Ser Ala Ser Thr Lys Gly Pro
    130              135                140

Ser Val Phe Pro Leu Ala Pro Cys Ser Arg Ser Thr Ser Glu Ser Thr
```

-continued

```
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
                195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Ser Cys Pro Ala Pro Glu Phe Leu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Val Asp Val Ser Gln Glu Asp
                275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
                340                 345                 350

Thr Ile Ser Lys Ala Lys Gly Gln Pro Arg Glu Pro Gln Val Tyr Thr
                355                 360                 365

Leu Pro Pro Ser Gln Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
                420                 425                 430

Ser Arg Trp Gln Glu Gly Asn Val Phe Ser Cys Ser Val Met His Glu
                435                 440                 445

Ala Leu His Asn His Tyr Thr Gln Lys Ser Leu Ser Leu Ser Leu Gly
    450                 455                 460

Lys
465

<210> SEQ ID NO 11
<211> LENGTH: 465
<212> TYPE: PRT
<213> ORGANISM: Artificial Sequence
<220> FEATURE:
<223> OTHER INFORMATION: VH3 of the humanized 6G10F6 antibody

<400> SEQUENCE: 11

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
                20                  25                  30

Pro Ser Gln Thr Leu Ser Leu Thr Cys Thr Val Ser Gly Tyr Ser Ile
```

```
                35                  40                  45
Thr Ser Asp Tyr Ala Trp Asn Trp Phe Arg Gln Pro Pro Gly Lys Lys
    50                  55                  60
Leu Glu Trp Met Gly Tyr Thr Ser Tyr Ser Gly Ser Thr Ser Tyr Asn
65                  70                  75                  80
Pro Ser Leu Lys Ser Arg Val Thr Ile Ser Arg Asp Thr Ser Lys Asn
                85                  90                  95
Gln Ile Ser Leu Lys Leu Ser Ser Val Thr Ala Ala Asp Thr Ala Thr
                100                 105                 110
Tyr Tyr Cys Ala Arg Glu Val Thr Thr Phe Gly Tyr Phe Asp Tyr Trp
            115                 120                 125
Gly Gln Gly Thr Leu Val Thr Val Ser Ser Ala Ser Thr Lys Gly Pro
    130                 135                 140
Ser Val Phe Pro Leu Ala Pro Cys Ser Arg Ser Thr Ser Glu Ser Thr
145                 150                 155                 160
Ala Ala Leu Gly Cys Leu Val Lys Asp Tyr Phe Pro Glu Pro Val Thr
            165                 170                 175
Val Ser Trp Asn Ser Gly Ala Leu Thr Ser Gly Val His Thr Phe Pro
            180                 185                 190
Ala Val Leu Gln Ser Ser Gly Leu Tyr Ser Leu Ser Ser Val Val Thr
        195                 200                 205
Val Pro Ser Ser Ser Leu Gly Thr Lys Thr Tyr Thr Cys Asn Val Asp
    210                 215                 220
His Lys Pro Ser Asn Thr Lys Val Asp Lys Arg Val Glu Ser Lys Tyr
225                 230                 235                 240
Gly Pro Pro Cys Pro Ser Cys Pro Ala Pro Glu Phe Leu Gly Gly Pro
            245                 250                 255
Ser Val Phe Leu Phe Pro Pro Lys Pro Lys Asp Thr Leu Met Ile Ser
            260                 265                 270
Arg Thr Pro Glu Val Thr Cys Val Val Val Asp Val Ser Gln Glu Asp
        275                 280                 285
Pro Glu Val Gln Phe Asn Trp Tyr Val Asp Gly Val Glu Val His Asn
    290                 295                 300
Ala Lys Thr Lys Pro Arg Glu Glu Gln Phe Asn Ser Thr Tyr Arg Val
305                 310                 315                 320
Val Ser Val Leu Thr Val Leu His Gln Asp Trp Leu Asn Gly Lys Glu
            325                 330                 335
Tyr Lys Cys Lys Val Ser Asn Lys Gly Leu Pro Ser Ser Ile Glu Lys
            340                 345                 350
Thr Ile Ser Lys Ala Lys Gly Gln Pro Arg Glu Pro Gln Val Tyr Thr
        355                 360                 365
Leu Pro Pro Ser Gln Glu Glu Met Thr Lys Asn Gln Val Ser Leu Thr
    370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Arg Leu Thr Val Asp Lys
            420                 425                 430
Ser Arg Trp Gln Glu Gly Asn Val Phe Ser Cys Ser Val Met His Glu
        435                 440                 445
Ala Leu His Asn His Tyr Thr Gln Lys Ser Leu Ser Leu Ser Leu Gly
    450                 455                 460
```

-continued

```
Lys
465

<210> SEQ ID NO 12
<211> LENGTH: 465
<212> TYPE: PRT
<213> ORGANISM: Artificial Sequence
<220> FEATURE:
<223> OTHER INFORMATION: VH4 of the humanized 6G10F6 antibody

<400> SEQUENCE: 12

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Gln Thr Leu Ser Leu Thr Cys Thr Val Ser Gly Tyr Ser Ile
            35                  40                  45

Thr Ser Asp Tyr Ala Trp Asn Trp Phe Arg Gln Pro Pro Gly Lys Lys
        50                  55                  60

Leu Glu Trp Met Gly Tyr Thr Ser Tyr Ser Gly Ser Thr Ser Tyr Asn
65                  70                  75                  80

Pro Ser Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Glu Val Thr Thr Phe Gly Tyr Phe Asp Tyr Trp
            115                 120                 125

Gly Gln Gly Thr Leu Val Thr Val Ser Ser Ala Ser Thr Lys Gly Pro
        130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
            195                 200                 205

Val Pro Ser Ser Ser Leu Gly Thr Lys Thr Tyr Thr Cys Asn Val Asp
        210                 215                 220

His Lys Pro Ser Asn Thr Lys Val Asp Lys Arg Val Glu Ser Lys Tyr
225                 230                 235                 240

Gly Pro Pro Cys Pro Ser Cys Pro Ala Pro Glu Phe Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
            275                 280                 285

Pro Glu Val Gln Phe Asn Trp Tyr Val Asp Gly Val Glu Val His Asn
        290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
                340                 345                 350
```

```
Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
        435                 440                 445

Ala Leu His Asn His Tyr Thr Gln Lys Ser Leu Ser Leu Ser Leu Gly
    450                 455                 460

Lys
465

<210> SEQ ID NO 13
<211> LENGTH: 465
<212> TYPE: PRT
<213> ORGANISM: Artificial Sequence
<220> FEATURE:
<223> OTHER INFORMATION: VH5 of the humanized 6G10F6 antibody

<400> SEQUENCE: 13

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Gln Thr Leu Ser Leu Thr Cys Thr Val Ser Gly Tyr Ser Ile
        35                  40                  45

Thr Ser Asp Tyr Ala Trp Asn Trp Ile Arg Gln Pro Pro Gly Lys Gly
    50                  55                  60

Leu Glu Trp Ile Gly Tyr Thr Ser Tyr Ser Gly Ser Thr Ser Tyr Asn
65                  70                  75                  80

Pro Ser Leu Lys Ser Arg Val Thr Ile Ser Arg Asp Thr Ser Lys Asn
                85                  90                  95

Gln Ile Ser Leu Lys Leu Ser Ser Val Thr Ala Ala Asp Thr Ala Thr
            100                 105                 110

Tyr Tyr Cys Ala Arg Glu Val Thr Thr Phe Gly Tyr Phe Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240
```

-continued

```
Gly Pro Pro Cys Pro Ser Cys Pro Ala Pro Glu Phe Leu Gly Gly Pro
            245             250             255

Ser Val Phe Leu Phe Pro Pro Lys Pro Lys Asp Thr Leu Met Ile Ser
            260             265             270

Arg Thr Pro Glu Val Thr Cys Val Val Val Asp Val Ser Gln Glu Asp
            275             280             285

Pro Glu Val Gln Phe Asn Trp Tyr Val Asp Gly Val Glu Val His Asn
            290             295             300

Ala Lys Thr Lys Pro Arg Glu Glu Gln Phe Asn Ser Thr Tyr Arg Val
305             310             315             320

Val Ser Val Leu Thr Val Leu His Gln Asp Trp Leu Asn Gly Lys Glu
            325             330             335

Tyr Lys Cys Lys Val Ser Asn Lys Gly Leu Pro Ser Ser Ile Glu Lys
            340             345             350

Thr Ile Ser Lys Ala Lys Gly Gln Pro Arg Glu Pro Gln Val Tyr Thr
            355             360             365

Leu Pro Pro Ser Gln Glu Glu Met Thr Lys Asn Gln Val Ser Leu Thr
            370             375             380

Cys Leu Val Lys Gly Phe Tyr Pro Ser Asp Ile Ala Val Glu Trp Glu
385             390             395             400

Ser Asn Gly Gln Pro Glu Asn Asn Tyr Lys Thr Thr Pro Pro Val Leu
            405             410             415

Asp Ser Asp Gly Ser Phe Phe Leu Tyr Ser Arg Leu Thr Val Asp Lys
            420             425             430

Ser Arg Trp Gln Glu Gly Asn Val Phe Ser Cys Ser Val Met His Glu
            435             440             445

Ala Leu His Asn His Tyr Thr Gln Lys Ser Leu Ser Leu Ser Leu Gly
            450             455             460

Lys
465
```

```
<210> SEQ ID NO 14
<211> LENGTH: 234
<212> TYPE: PRT
<213> ORGANISM: Artificial Sequence
<220> FEATURE:
<223> OTHER INFORMATION: VL1 of the humanized 6G10F6 antibody

<400> SEQUENCE: 14

Met Gly Trp Ser Cys Ile Ile Leu Phe Leu Val Ala Thr Ala Thr Gly
1               5               10              15

Val His Ser Gln Thr Val Val Thr Gln Glu Pro Ser Leu Thr Val Ser
            20              25              30

Pro Gly Gly Thr Val Thr Leu Thr Cys Arg Ser Ser Thr Gly Ala Val
            35              40              45

Thr Thr Ser Asn Tyr Ala Asn Trp Phe Gln Gln Lys Pro Gly Gln Ala
            50              55              60

Pro Arg Ala Leu Ile Tyr Gly Thr Ser Asn Arg Ala Pro Trp Thr Pro
65              70              75              80

Ala Arg Phe Ser Gly Ser Leu Leu Gly Gly Lys Ala Ala Leu Thr Leu
            85              90              95

Ser Gly Val Gln Pro Glu Asp Glu Ala Glu Tyr Tyr Cys Ala Leu Trp
            100             105             110

Tyr Ser Thr His Tyr Val Phe Gly Thr Gly Thr Lys Val Thr Val Leu
            115             120             125
```

-continued

```
Gly Gln Pro Lys Ala Ala Pro Ser Val Thr Leu Phe Pro Pro Ser Ser
    130             135             140

Glu Glu Leu Gln Ala Asn Lys Ala Thr Leu Val Cys Leu Ile Ser Asp
145             150             155             160

Phe Tyr Pro Gly Ala Val Thr Val Ala Trp Lys Ala Asp Ser Ser Pro
            165             170             175

Val Lys Ala Gly Val Glu Thr Thr Thr Pro Ser Lys Gln Ser Asn Asn
            180             185             190

Lys Tyr Ala Ala Ser Ser Tyr Leu Ser Leu Thr Pro Glu Gln Trp Lys
            195             200             205

Ser His Arg Ser Tyr Ser Cys Gln Val Thr His Glu Gly Ser Thr Val
    210             215             220

Glu Lys Thr Val Ala Pro Thr Glu Cys Ser
225             230
```

```
<210> SEQ ID NO 15
<211> LENGTH: 234
<212> TYPE: PRT
<213> ORGANISM: Artificial Sequence
<220> FEATURE:
<223> OTHER INFORMATION: VL2 of the humanized 6G10F6 antibody

<400> SEQUENCE: 15
```

```
Met Gly Trp Ser Cys Ile Ile Leu Phe Leu Val Ala Thr Ala Thr Gly
1               5               10              15

Val His Ser Gln Thr Val Val Thr Gln Glu Pro Ser Leu Thr Val Ser
            20              25              30

Pro Gly Gly Thr Val Thr Leu Thr Cys Arg Ser Ser Thr Gly Ala Val
            35              40              45

Thr Thr Ser Asn Tyr Ala Asn Trp Phe Gln Gln Lys Pro Gly Gln Ala
    50              55              60

Pro Arg Gly Leu Ile Gly Gly Thr Ser Asn Arg Ala Pro Trp Thr Pro
65              70              75              80

Ala Arg Phe Ser Gly Ser Leu Leu Gly Gly Lys Ala Ala Leu Thr Leu
            85              90              95

Ser Gly Val Gln Pro Glu Asp Glu Ala Glu Tyr Phe Cys Ala Leu Trp
            100             105             110

Tyr Ser Thr His Tyr Val Phe Gly Thr Gly Thr Lys Val Thr Val Leu
            115             120             125

Gly Gln Pro Lys Ala Ala Pro Ser Val Thr Leu Phe Pro Pro Ser Ser
    130             135             140

Glu Glu Leu Gln Ala Asn Lys Ala Thr Leu Val Cys Leu Ile Ser Asp
145             150             155             160

Phe Tyr Pro Gly Ala Val Thr Val Ala Trp Lys Ala Asp Ser Ser Pro
            165             170             175

Val Lys Ala Gly Val Glu Thr Thr Thr Pro Ser Lys Gln Ser Asn Asn
            180             185             190

Lys Tyr Ala Ala Ser Ser Tyr Leu Ser Leu Thr Pro Glu Gln Trp Lys
            195             200             205

Ser His Arg Ser Tyr Ser Cys Gln Val Thr His Glu Gly Ser Thr Val
    210             215             220

Glu Lys Thr Val Ala Pro Thr Glu Cys Ser
225             230
```

```
<210> SEQ ID NO 16
```

```
<211> LENGTH: 234
<212> TYPE: PRT
<213> ORGANISM: Artificial Sequence
<220> FEATURE:
<223> OTHER INFORMATION: VL3 of the humanized 6G10F6 antibody

<400> SEQUENCE: 16

Met Gly Trp Ser Cys Ile Ile Leu Phe Leu Val Ala Thr Ala Thr Gly
1               5                   10                  15

Val His Ser Gln Thr Val Val Thr Gln Glu Pro Ser Leu Thr Val Ser
            20                  25                  30

Pro Gly Gly Thr Val Thr Leu Thr Cys Arg Ser Ser Thr Gly Ala Val
        35                  40                  45

Thr Thr Ser Asn Tyr Ala Asn Trp Phe Gln Gln Lys Pro Gly Gln Ala
    50                  55                  60

Pro Arg Gly Leu Ile Gly Gly Thr Ser Asn Arg Ala Pro Gly Val Pro
65                  70                  75                  80

Ala Arg Phe Ser Gly Ser Leu Leu Gly Asp Lys Ala Ala Leu Thr Leu
                85                  90                  95

Ser Gly Val Gln Pro Glu Asp Glu Ala Glu Tyr Phe Cys Ala Leu Trp
            100                 105                 110

Tyr Ser Thr His Tyr Val Phe Gly Thr Gly Thr Lys Val Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230

<210> SEQ ID NO 17
<211> LENGTH: 234
<212> TYPE: PRT
<213> ORGANISM: Artificial Sequence
<220> FEATURE:
<223> OTHER INFORMATION: VL4 of the humanized 6G10F6 antibody

<400> SEQUENCE: 17

Met Gly Trp Ser Cys Ile Ile Leu Phe Leu Val Ala Thr Ala Thr Gly
1               5                   10                  15

Val His Ser Gln Thr Val Val Thr Gln Glu Pro Ser Leu Thr Val Ser
            20                  25                  30

Pro Gly Gly Thr Val Thr Leu Thr Cys Arg Ser Ser Thr Gly Ala Val
        35                  40                  45

Thr Thr Ser Asn Tyr Ala Asn Trp Phe Gln Gln Lys Pro Gly His Ala
    50                  55                  60

Phe Thr Gly Leu Ile Gly Gly Thr Ser Asn Arg Ala Pro Trp Thr Pro
65                  70                  75                  80

Ala Arg Phe Ser Gly Ser Leu Leu Gly Gly Lys Ala Ala Leu Thr Leu
```

-continued

```
                    85                  90                  95
Ser Gly Val Gln Pro Glu Asp Glu Ala Glu Tyr Phe Cys Ala Leu Trp
                100                 105                 110

Tyr Ser Thr His Tyr Val Phe Gly Thr Gly Thr Lys Val Thr Val Leu
            115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
                180                 185                 190

Lys Tyr Ala Ala Ser Ser Tyr Leu Ser Leu Thr Pro Glu Gln Trp Lys
            195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230
```

```
<210> SEQ ID NO 18
<211> LENGTH: 234
<212> TYPE: PRT
<213> ORGANISM: Artificial Sequence
<220> FEATURE:
<223> OTHER INFORMATION: VL5 of the humanized 6G10F6 antibody

<400> SEQUENCE: 18

Met Gly Trp Ser Cys Ile Ile Leu Phe Leu Val Ala Thr Ala Thr Gly
1               5                   10                  15

Val His Ser Gln Thr Val Val Thr Gln Glu Pro Ser Leu Thr Val Ser
                20                  25                  30

Pro Gly Gly Thr Val Thr Leu Thr Cys Arg Ser Ser Thr Gly Ala Val
            35                  40                  45

Thr Thr Ser Asn Tyr Ala Asn Trp Val Gln Glu Lys Pro Gly His Ala
    50                  55                  60

Phe Thr Gly Leu Ile Gly Gly Thr Ser Asn Arg Ala Pro Trp Thr Pro
65                  70                  75                  80

Ala Arg Phe Ser Gly Ser Leu Leu Gly Gly Lys Ala Ala Leu Thr Leu
                85                  90                  95

Ser Gly Val Gln Pro Glu Asp Glu Ala Glu Tyr Phe Cys Ala Leu Trp
                100                 105                 110

Tyr Ser Thr His Tyr Val Phe Gly Thr Gly Thr Lys Val Thr Val Leu
            115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
                180                 185                 190

Lys Tyr Ala Ala Ser Ser Tyr Leu Ser Leu Thr Pro Glu Gln Trp Lys
            195                 200                 205

Ser His Arg Ser Tyr Ser Cys Gln Val Thr His Glu Gly Ser Thr Val
```

```
          210                  215                  220

Glu Lys Thr Val Ala Pro Thr Glu Cys Ser
225                  230

<210> SEQ ID NO 19
<211> LENGTH: 234
<212> TYPE: PRT
<213> ORGANISM: Artificial Sequence
<220> FEATURE:
<223> OTHER INFORMATION: VL6 of the humanized 6G10F6 antibody

<400> SEQUENCE: 19

Met Gly Trp Ser Cys Ile Ile Leu Phe Leu Val Ala Thr Ala Thr Gly
1               5                   10                  15

Val His Ser Gln Thr Val Val Thr Gln Glu Pro Ser Leu Thr Val Ser
            20                  25                  30

Pro Gly Gly Thr Val Thr Leu Thr Cys Arg Ser Ser Thr Gly Ala Val
        35                  40                  45

Thr Thr Ser Asn Tyr Ala Asn Trp Val Gln Glu Lys Pro Gly Gln Ala
    50                  55                  60

Pro Arg Gly Leu Ile Gly Gly Thr Ser Asn Arg Ala Pro Gly Val Pro
65                  70                  75                  80

Ala Arg Phe Ser Gly Ser Leu Leu Gly Asp Lys Ala Ala Leu Thr Leu
            85                  90                  95

Ser Gly Val Gln Pro Glu Asp Glu Ala Glu Tyr Phe Cys Ala Leu Trp
            100                 105                 110

Tyr Ser Thr His Tyr Val Phe Gly Thr Gly Thr Lys Val Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
            165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230

<210> SEQ ID NO 20
<211> LENGTH: 234
<212> TYPE: PRT
<213> ORGANISM: Artificial Sequence
<220> FEATURE:
<223> OTHER INFORMATION: VL7 of the humanized 6G10F6 antibody

<400> SEQUENCE: 20

Met Gly Trp Ser Cys Ile Ile Leu Phe Leu Val Ala Thr Ala Thr Gly
1               5                   10                  15

Val His Ser Gln Thr Val Val Thr Gln Glu Pro Ser Leu Thr Val Ser
            20                  25                  30

Pro Gly Gly Thr Val Thr Leu Thr Cys Arg Ser Ser Thr Gly Ala Val
        35                  40                  45
```

-continued

```
Thr Thr Ser Asn Tyr Ala Asn Trp Phe Gln Gln Lys Pro Gly His Ala
    50              55                  60

Phe Thr Gly Leu Ile Gly Gly Thr Ser Asn Arg Ala Pro Gly Val Pro
65              70                  75                  80

Ala Arg Phe Ser Gly Ser Leu Leu Gly Asp Lys Ala Ala Leu Thr Leu
                85                  90                  95

Ser Gly Val Gln Pro Glu Asp Glu Ala Glu Tyr Phe Cys Ala Leu Trp
                100                 105                 110

Tyr Ser Thr His Tyr Val Phe Gly Thr Gly Thr Lys Val Thr Val Leu
                115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
                180                 185                 190

Lys Tyr Ala Ala Ser Ser Tyr Leu Ser Leu Thr Pro Glu Gln Trp Lys
                195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230
```

```
<210> SEQ ID NO 21
<211> LENGTH: 234
<212> TYPE: PRT
<213> ORGANISM: Artificial Sequence
<220> FEATURE:
<223> OTHER INFORMATION: VL8 of the humanized 6G10F6 antibody

<400> SEQUENCE: 21
```

```
Met Gly Trp Ser Cys Ile Ile Leu Phe Leu Val Ala Thr Ala Thr Gly
1               5                   10                  15

Val His Ser Gln Thr Val Val Thr Gln Glu Pro Ser Leu Thr Val Ser
                20                  25                  30

Pro Gly Gly Thr Val Thr Leu Thr Cys Arg Ser Ser Thr Gly Ala Val
                35                  40                  45

Thr Thr Ser Asn Tyr Ala Asn Trp Val Gln Glu Lys Pro Gly His Ala
    50              55                  60

Phe Thr Gly Leu Ile Gly Gly Thr Ser Asn Arg Ala Pro Gly Val Pro
65              70                  75                  80

Ala Arg Phe Ser Gly Ser Leu Leu Gly Asp Lys Ala Ala Leu Thr Leu
                85                  90                  95

Ser Gly Val Gln Pro Glu Asp Glu Ala Glu Tyr Phe Cys Ala Leu Trp
                100                 105                 110

Tyr Ser Thr His Tyr Val Phe Gly Thr Gly Thr Lys Val Thr Val Leu
                115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175
```

```
Val Lys Ala Gly Val Glu Thr Thr Thr Pro Ser Lys Gln Ser Asn Asn
            180              185             190

Lys Tyr Ala Ala Ser Ser Tyr Leu Ser Leu Thr Pro Glu Gln Trp Lys
        195              200             205

Ser His Arg Ser Tyr Ser Cys Gln Val Thr His Glu Gly Ser Thr Val
    210              215             220

Glu Lys Thr Val Ala Pro Thr Glu Cys Ser
225              230
```

```
<210> SEQ ID NO 22
<211> LENGTH: 1398
<212> TYPE: DNA
<213> ORGANISM: Artificial Sequence
<220> FEATURE:
<223> OTHER INFORMATION: VH1 of the humanized 6G10F6 antibody

<400> SEQUENCE: 22
atgggctggt cctgcatcat tctgtttctg gtggccacag ccaccggcgt gcactctcag    60
gtgcagctgc aggagtctgg accaggactg gtgaagccat cccagaccct gtctctgacc   120
tgcacagtgt ctggctacag catcacatcc gattatgcat ggaactggat caggcagcca   180
cctggcaagg gactggagtg gatcggctac acctcctatt ctggcagcac atcctacaac   240
ccctctctga gagcagagt gaccatcagc gtggacacat ccaagaatca gttcagcctg   300
aagctgagct ccgtgaccgc agcagataca gccgtgtact attgtgcccg ggaggtgacc   360
acattcggct actttgacta ttggggccag ggcaccctgg tgacagtgtc tagcgcctct   420
acaaagggcc ccagcgtttt cccactggct ccctgtagca gaagcaccag cgaatctaca   480
gccgctctgg gctgcctcgt gaaggactac tttcctgagc cagtgaccgt gtcctggaac   540
tctggcgctc tgacatctgg cgtgcacacc tttccagccg tgctgcaatc tagcggcctg   600
tactctctga gcagcgtggt cacagtgcct agctctagcc tgggcaccaa gacctacacc   660
tgtaatgtgg atcacaagcc cagcaacacc aaggtggaca agagagtgga atctaagtac   720
ggccctcctt gtcctagctg ccccgctcct gaatttctcg gcggaccttc cgtgttcctg   780
tttcctccaa agcctaagga caccctgatg atcagcagaa cccctgaagt gacctgcgtg   840
gtggtggacg tgtcccaaga ggatcctgag gtgcagttca attggtacgt ggacggcgtg   900
gaagtgcaca cgccaagac caagcctaga gaggaacagt tcaacagcac ctacagagtg   960
gtgtccgtgc tgacagtgct gcaccaggat tggctgaacg gcaaagagta caagtgcaag  1020
gtgtccaaca agggcctgcc tagcagcatc gagaaaacca tcagcaaggc caagggacag  1080
cccagggaac cccaggttta cacactgcct ccaagccaag aggaaatgac caagaatcag  1140
gtgtccctga cctgcctggt taagggcttc taccctccg atatcgccgt ggaatgggag  1200
agcaatggcc agcctgagaa caactacaag acaacccctc ctgtgctgga cagcgacggc  1260
tcattcttcc tgtacagcag actgaccgtg gacaagtcca gatggcaaga gggcaacgtg  1320
ttctcctgca cgtgatgca cgaggccctg cacaaccact acacccagaa gtccctgtct  1380
ctgtccctgg gcaaatga                                                 1398
```

```
<210> SEQ ID NO 23
<211> LENGTH: 1398
<212> TYPE: DNA
<213> ORGANISM: Artificial Sequence
<220> FEATURE:
<223> OTHER INFORMATION: VH2 of the humanized 6G10F6 antibody

<400> SEQUENCE: 23
```

-continued

```
atgggctggt cctgcatcat tctgtttctg gtggccacag ccaccggcgt gcactctcag      60
gtgcagctgc aggagtctgg accaggactg gtgaagccat cccagaccct gtctctgacc     120
tgcacagtgt ctggctacag catcacatcc gattatgcct ggaactggat caggcagcca     180
cctggcaagg gactggagtg gatcggctac acctcctatt ctggcagcac atcctacaac     240
ccctctctga gagccgggt gaccatcagc agagacacat ccaagaatca gttctttctg     300
aagctgagct ccgtgaccgc cgccgataca gccgtgtact attgtgcccg ggaggtgacc     360
acattcggct actttgacta ttggggccag ggcaccctgg tgacagtgtc tagcgcctct     420
acaaagggcc ccagcgtttt cccactggct ccctgtagca gaagcaccag cgaatctaca     480
gccgctctgg gctgcctcgt gaaggactac tttcctgagc cagtgaccgt gtcctggaac     540
tctggcgctc tgacatctgg cgtgcacacc tttccagccg tgctgcaatc tagcggcctg     600
tactctctga gcagcgtggt cacagtgcct agctctagcc tgggcaccaa gacctacacc     660
tgtaatgtgg atcacaagcc cagcaacacc aaggtggaca agagagtgga atctaagtac     720
ggccctcctt gtcctagctg ccccgctcct gaatttctcg gcggaccttc cgtgttcctg     780
tttcctccaa agcctaagga caccctgatg atcagcagaa cccctgaagt gacctgcgtg     840
gtggtggacg tgtcccaaga ggatcctgag gtgcagttca attggtacgt ggacggcgtg     900
gaagtgcaca cgccaagac caagcctaga gaggaacagt tcaacagcac ctacagagtg     960
gtgtccgtgc tgacagtgct gcaccaggat tggctgaacg gcaaagagta caagtgcaag    1020
gtgtccaaca agggcctgcc tagcagcatc gagaaaacca tcagcaaggc caagggacag    1080
cccagggaac cccaggttta cacactgcct ccaagccaag aggaaatgac caagaatcag    1140
gtgtccctga cctgcctggt taagggcttc taccctccg atatcgccgt ggaatgggag    1200
agcaatggcc agcctgagaa caactacaag acaacccctc ctgtgctgga cagcgacggc    1260
tcattcttcc tgtacagcag actgaccgtg gacaagtcca gatggcaaga gggcaacgtg    1320
ttctcctgca gcgtgatgca cgaggccctg cacaaccact acacccagaa gtccctgtct    1380
ctgtccctgg gcaaatga                                                  1398
```

<210> SEQ ID NO 24
<211> LENGTH: 1398
<212> TYPE: DNA
<213> ORGANISM: Artificial Sequence
<220> FEATURE:
<223> OTHER INFORMATION: VH3 of the humanized 6G10F6

<400> SEQUENCE: 24

```
atgggctggt cctgcatcat tctgtttctg gtggccacag ccaccggcgt gcactctcag      60
gtgcagctgc aggagtctgg accaggactg gtgaagccat cccagaccct gtctctgacc     120
tgcacagtgt ctggctacag catcacatcc gattatgcct ggaactggtt caggcagccc     180
cctggcaaga agctggagtg gatgggctac acctcctatt ctggcagcac atcctacaac     240
ccctctctga gagccgggt gaccatcagc agagacacat ccaagaatca gatcagcctg     300
aagctgagct ccgtgaccgc agcagatacc gcaacatact attgtgcccg ggaggtgacc     360
acattcggct actttgacta ttggggccag ggcaccctgg tgacagtgtc tagcgcctct     420
acaaagggcc ccagcgtttt cccactggct ccctgtagca gaagcaccag cgaatctaca     480
gccgctctgg gctgcctcgt gaaggactac tttcctgagc cagtgaccgt gtcctggaac     540
tctggcgctc tgacatctgg cgtgcacacc tttccagccg tgctgcaatc tagcggcctg     600
```

```
tactctctga gcagcgtggt cacagtgcct agctctagcc tgggcaccaa gacctacacc      660
tgtaatgtgg atcacaagcc cagcaacacc aaggtggaca agagagtgga atctaagtac      720
ggccctcctt gtcctagctg ccccgctcct gaatttctcg gcggaccttc cgtgttcctg      780
tttcctccaa agcctaagga caccctgatg atcagcagaa cccctgaagt gacctgcgtg      840
gtggtggacg tgtcccaaga ggatcctgag gtgcagttca attggtacgt ggacggcgtg      900
gaagtgcaca acgccaagac caagcctaga gaggaacagt tcaacagcac ctacagagtg      960
gtgtccgtgc tgacagtgct gcaccaggat tggctgaacg gcaaagagta caagtgcaag     1020
gtgtccaaca agggcctgcc tagcagcatc gagaaaacca tcagcaaggc caagggacag     1080
cccagggaac cccaggttta cacactgcct ccaagccaag aggaaatgac caagaatcag     1140
gtgtccctga cctgcctggt taagggcttc taccctccg atatcgccgt ggaatgggag     1200
agcaatggcc agcctgagaa caactacaag acaacccctc ctgtgctgga cagcgacggc     1260
tcattcttcc tgtacagcag actgaccgtg gacaagtcca gatggcaaga gggcaacgtg     1320
ttctcctgca gcgtgatgca cgaggccctg cacaaccact acacccagaa gtccctgtct     1380
ctgtccctgg gcaaatga                                                   1398

<210> SEQ ID NO 25
<211> LENGTH: 1398
<212> TYPE: DNA
<213> ORGANISM: Artificial Sequence
<220> FEATURE:
<223> OTHER INFORMATION: VH4 of the humamized 6G10F6 antibody

<400> SEQUENCE: 25
atgggctggt cctgcatcat tctgtttctg gtggccacag ccaccggcgt gcactctcag       60
gtgcagctgc aggagtctgg accaggactg gtgaagccat cccagaccct gtctctgacc      120
tgcacagtgt ctggctacag catcacatcc gattatgcat ggaactggtt caggcagcca      180
cctggcaaga agctggagtg gatgggctac acctcctatt ctggcagcac atcctacaac      240
ccctctctga agagcagagt gaccatcagc gtggacacat ccaagaatca gtttagcctg      300
aagctgagct ccgtgaccgc agcagataca gccgtgtact attgtgcccg ggaggtgacc      360
acattcggct actttgacta ttggggccag ggcacccctg tgacagtgtc tagcgcctct      420
acaaagggcc ccagcgtttt cccactggct ccctgtagca gaagcaccag cgaatctaca      480
gccgctctgg gctgcctcgt gaaggactac tttcctgagc cagtgaccgt gtcctggaac      540
tctggcgctc tgacatctgg cgtgcacacc tttccagccg tgctgcaatc tagcggcctg      600
tactctctga gcagcgtggt cacagtgcct agctctagcc tgggcaccaa gacctacacc      660
tgtaatgtgg atcacaagcc cagcaacacc aaggtggaca agagagtgga atctaagtac      720
ggccctcctt gtcctagctg ccccgctcct gaatttctcg gcggaccttc cgtgttcctg      780
tttcctccaa agcctaagga caccctgatg atcagcagaa cccctgaagt gacctgcgtg      840
gtggtggacg tgtcccaaga ggatcctgag gtgcagttca attggtacgt ggacggcgtg      900
gaagtgcaca acgccaagac caagcctaga gaggaacagt tcaacagcac ctacagagtg      960
gtgtccgtgc tgacagtgct gcaccaggat tggctgaacg gcaaagagta caagtgcaag     1020
gtgtccaaca agggcctgcc tagcagcatc gagaaaacca tcagcaaggc caagggacag     1080
cccagggaac cccaggttta cacactgcct ccaagccaag aggaaatgac caagaatcag     1140
gtgtccctga cctgcctggt taagggcttc taccctccg atatcgccgt ggaatgggag     1200
agcaatggcc agcctgagaa caactacaag acaacccctc ctgtgctgga cagcgacggc     1260
```

-continued

```
tcattcttcc tgtacagcag actgaccgtg gacaagtcca gatggcaaga gggcaacgtg      1320
ttctcctgca gcgtgatgca cgaggccctg cacaaccact acacccagaa gtccctgtct      1380
ctgtccctgg gcaaatga                                                     1398

<210> SEQ ID NO 26
<211> LENGTH: 1398
<212> TYPE: DNA
<213> ORGANISM: Artificial Sequence
<220> FEATURE:
<223> OTHER INFORMATION: VH5 of the humanied 6G10F6

<400> SEQUENCE: 26
atgggctggt cctgcatcat tctgtttctg gtggccacag ccaccggcgt gcactctcag        60
gtgcagctgc aggagtctgg accaggactg gtgaagccat cccagaccct gtctctgacc       120
tgcacagtgt ctggctacag catcacatcc gattatgcct ggaactggat caggcagcca       180
cctggcaagg gactggagtg gatcggctac acctcctatt ctggcagcac atcctacaac       240
ccctctctga gagccgggt gaccatcagc agagacacat ccaagaatca gatcagcctg        300
aagctgagct ccgtgaccgc agcagatacc gcaacatact attgtgcccg ggaggtgacc       360
acattcggct actttgacta ttggggccag ggcaccctgg tgacagtgtc tagcgcctct       420
acaaagggcc ccagcgtttt cccactggct ccctgtagca gaagcaccag cgaatctaca       480
gccgctctgg gctgcctcgt gaaggactac tttcctgagc cagtgaccgt gtcctggaac       540
tctggcgctc tgacatctgg cgtgcacacc tttccagccg tgctgcaatc tagcggcctg       600
tactctctga gcagcgtggt cacagtgcct agctctagcc tgggcaccaa gacctacacc       660
tgtaatgtgg atcacaagcc cagcaacacc aaggtggaca agagagtgga atctaagtac       720
ggccctcctt gtcctagctg ccccgctcct gaatttctcg gcggaccttc cgtgttcctg       780
tttcctccaa agcctaagga caccctgatg atcagcagaa cccctgaagt gacctgcgtg       840
gtggtggacg tgtcccaaga ggatcctgag gtgcagttca attggtacgt ggacggcgtg       900
gaagtgcaca cgccaagac caagcctaga gaggaacagt tcaacagcac ctacagagtg       960
gtgtccgtgc tgacagtgct gcaccaggat tggctgaacg gcaaagagta caagtgcaag      1020
gtgtccaaca agggcctgcc tagcagcatc gagaaaacca tcagcaaggc caagggacag      1080
cccagggaac cccaggttta cacactgcct ccaagccaag aggaaatgac caagaatcag      1140
gtgtccctga cctgcctggt taagggcttc taccctccg atatcgccgt ggaatgggag      1200
agcaatggcc agcctgagaa caactacaag acaacccctc ctgtgctgga cagcgacggc      1260
tcattcttcc tgtacagcag actgaccgtg gacaagtcca gatggcaaga gggcaacgtg      1320
ttctcctgca gcgtgatgca cgaggccctg cacaaccact acacccagaa gtccctgtct      1380
ctgtccctgg gcaaatga                                                     1398

<210> SEQ ID NO 27
<211> LENGTH: 705
<212> TYPE: DNA
<213> ORGANISM: Artificial Sequence
<220> FEATURE:
<223> OTHER INFORMATION: VL1 of the humanized 6G10F6 antibody

<400> SEQUENCE: 27
atgggctggt cctgcatcat tctgtttctg gtggccacag ccaccggcgt gcactctcag        60
acagtggtga cccaggagcc ttccctgaca gtgtctccag gcggcaccgt gacactgacc       120
```

```
tgcaggagct ccaccggagc agtgaccaca tctaactacg ccaattggtt ccagcagaag      180
ccaggacagg caccacgggc cctgatctat ggcacatcca acagggcacc atggacccct      240
gccagatttt ctggaagcct gctgggaggc aaggccgccc tgaccctgag cggcgtgcag      300
cccgaggacg aggccgagta ctattgtgcc ctgtggtact ccacacacta cgtgttcggc      360
acaggcacca aggtgaccgt gctgggacag cctaaggccg ctcctagcgt gacactgttt      420
cctccaagca gcgaggaact gcaggccaac aaagccacac tcgtgtgcct gatcagcgac      480
ttctatcccg gcgctgtgac agtggcctgg aaggctgata gctctcctgt gaaagccggc      540
gtggaaacca ccacacctag caagcagagc aacaacaaat acgccgccag cagctacctg      600
agcctgacac ctgagcagtg gaagtcccac agatcctaca gctgccaagt gacccacgag      660
ggcagcaccg tggaaaaaac agtggcccct accgagtgca gctga            705

<210> SEQ ID NO 28
<211> LENGTH: 705
<212> TYPE: DNA
<213> ORGANISM: Artificial Sequence
<220> FEATURE:
<223> OTHER INFORMATION: VL2 of the humanized 6G10F6 antibody

<400> SEQUENCE: 28
atgggctggt cctgcatcat tctgtttctg gtggccacag ccaccggcgt gcactctcag       60
acagtggtga cccaggagcc ttccctgaca gtgtctccag cggcaccgt gacactgacc      120 tgcaggagct ccaccggagc agtgaccaca tctaactacg ccaattggtt ccagcagaag      180
ccaggacagg caccaagggg actgatcgga ggcacatcca acagggcacc atggacccct      240
gccagatttt ctggaagcct gctgggaggc aaggccgccc tgaccctgag cggcgtgcag      300
cccgaggacg aggccgagta tttctgtgcc ctgtggtact ccacacacta cgtgttcggc      360
acaggcacca aggtgaccgt gctgggacag cctaaggccg ctcctagcgt gacactgttt      420
cctccaagca gcgaggaact gcaggccaac aaagccacac tcgtgtgcct gatcagcgac      480
ttctatcccg gcgctgtgac agtggcctgg aaggctgata gctctcctgt gaaagccggc      540
gtggaaacca ccacacctag caagcagagc aacaacaaat acgccgccag cagctacctg      600
agcctgacac ctgagcagtg gaagtcccac agatcctaca gctgccaagt gacccacgag      660
ggcagcaccg tggaaaaaac agtggcccct accgagtgca gctga            705

<210> SEQ ID NO 29
<211> LENGTH: 705
<212> TYPE: DNA
<213> ORGANISM: Artificial Sequence
<220> FEATURE:
<223> OTHER INFORMATION: VL3 of the humanized 6G10F6 antibody

<400> SEQUENCE: 29
atgggctggt cctgcatcat tctgtttctg gtggccacag ccaccggcgt gcactctcag       60
acagtggtga cccaggagcc ttccctgaca gtgtctccag gcggcaccgt gacactgacc      120
tgcaggagct ccaccggagc agtgaccaca tctaactacg ccaattggtt ccagcagaag      180
ccaggacagg caccaagggg actgatcgga ggcacatcca acagggcacc aggagtgcct      240
gcaagatttt ctggaagcct gctgggcgac aaggccgccc tgaccctgag cggagtgcag      300
ccagaggatg aggccgagta tttctgtgcc ctgtggtact ccacacacta cgtgttcggc      360
acaggcacca aggtgaccgt gctgggacag cctaaggccg ctcctagcgt gacactgttt      420
cctccaagca gcgaggaact gcaggccaac aaagccacac tcgtgtgcct gatcagcgac      480
```

-continued

```
ttctatcccg gcgctgtgac agtggcctgg aaggctgata gctctcctgt gaaagccggc      540
gtggaaacca ccacacctag caagcagagc aacaacaaat acgccgccag cagctacctg      600
agcctgacac ctgagcagtg gaagtcccac agatcctaca gctgccaagt gacccacgag      660
ggcagcaccg tggaaaaaac agtggcccct accgagtgca gctga                      705

<210> SEQ ID NO 30
<211> LENGTH: 705
<212> TYPE: DNA
<213> ORGANISM: Artificial Sequence
<220> FEATURE:
<223> OTHER INFORMATION: VL4 of the humanized 6G10F6 antibody

<400> SEQUENCE: 30
atgggctggt cctgcatcat tctgtttctg gtggccacag ccaccggcgt gcactctcag       60
acagtggtga cccaggagcc atccctgaca gtgtctccag gaggaaccgt gacactgacc      120
tgccggagct ccaccggagc agtgaccaca tctaactacg ccaattggtt ccagcagaag      180
cctggccacg cctttacagg cctgatcgga ggcacctcca acagggcacc atggacacct      240
gccagattct ctggaagcct gctgggaggc aaggccgccc tgaccctgag cggcgtgcag      300
cccgaggacg aggccgagta tttctgtgcc ctgtggtact ccacacacta cgtgttcggc      360
acaggcacca aggtgaccgt gctgggacag cctaaggccg ctcctagcgt gacactgttt      420
cctccaagca gcgaggaact gcaggccaac aaagccacac tcgtgtgcct gatcagcgac      480
ttctatcccg gcgctgtgac agtggcctgg aaggctgata gctctcctgt gaaagccggc      540
gtggaaacca ccacacctag caagcagagc aacaacaaat acgccgccag cagctacctg      600
agcctgacac ctgagcagtg gaagtcccac agatcctaca gctgccaagt gacccacgag      660
ggcagcaccg tggaaaaaac agtggcccct accgagtgca gctga                      705

<210> SEQ ID NO 31
<211> LENGTH: 705
<212> TYPE: DNA
<213> ORGANISM: Artificial Sequence
<220> FEATURE:
<223> OTHER INFORMATION: VL5 of the humanized 6G10F6 antibody

<400> SEQUENCE: 31
atgggctggt cctgcatcat tctgtttctg gtggccacag ccaccggcgt gcactctcag       60
acagtggtga cccaggagcc atccctgaca gtgtctccag gaggaaccgt gacactgacc      120
tgccggagct ccaccggagc agtgaccaca tctaactacg ccaattgggt gcaggagaag      180 cctggcacacg ccttcacagg actgatcgga ggcacctcca acagggcacc atggacacct      240
gccagatttt ctggaagcct gctgggaggc aaggccgccc tgaccctgag cggcgtgcag      300
cccgaggacg aggccgagta tttctgtgcc ctgtggtact ccacacacta cgtgttcggc      360
acaggcacca aggtgaccgt gctgggacag cctaaggccg ctcctagcgt gacactgttt      420
cctccaagca gcgaggaact gcaggccaac aaagccacac tcgtgtgcct gatcagcgac      480
ttctatcccg gcgctgtgac agtggcctgg aaggctgata gctctcctgt gaaagccggc      540
gtggaaacca ccacacctag caagcagagc aacaacaaat acgccgccag cagctacctg      600
agcctgacac ctgagcagtg gaagtcccac agatcctaca gctgccaagt gacccacgag      660
ggcagcaccg tggaaaaaac agtggcccct accgagtgca gctga                      705

<210> SEQ ID NO 32
```

<211> LENGTH: 705
<212> TYPE: DNA
<213> ORGANISM: Artificial Sequence
<220> FEATURE:
<223> OTHER INFORMATION: VL6 of the humanized 6G10F6 antibody

<400> SEQUENCE: 32
atgggctggt cctgcatcat tctgtttctg gtggccacag ccaccggcgt gcactctcag      60
acagtggtga cccaggagcc ttccctgaca gtgtctccag gcggcaccgt gacactgacc     120
tgcaggagct ccaccggagc agtgaccaca tctaactacg ccaattgggt gcaggagaag     180
ccaggacagg caccaagggg actgatcgga ggcacatcca accgggcccc cggcgtgcct     240
gccagattct ctggaagcct gctgggcgac aaggccgccc tgaccctgag cggagtgcag     300
ccagaggatg aggccgagta tttctgtgcc ctgtggtact ccacacacta cgtgttcggc     360
acaggcacca aggtgaccgt gctgggacag cctaaggccg ctcctagcgt gacactgttt     420
cctccaagca gcgaggaact gcaggccaac aaagccacac tcgtgtgcct gatcagcgac     480
ttctatcccg gcgctgtgac agtggcctgg aaggctgata gctctcctgt gaaagccggc     540
gtggaaacca ccacacctag caagcagagc aacaacaaat acgccgccag cagctacctg     600
agcctgacac ctgagcagtg gaagtcccac agatcctaca gctgccaagt gacccacgag     660
ggcagcaccg tggaaaaaac agtggcccct accgagtgca gctga                     705

<210> SEQ ID NO 33
<211> LENGTH: 705
<212> TYPE: DNA
<213> ORGANISM: Artificial Sequence
<220> FEATURE:
<223> OTHER INFORMATION: VL7 of the humanized 6G10F6 antibody

<400> SEQUENCE: 33
atgggctggt cctgcatcat tctgtttctg gtggccacag ccaccggcgt gcactctcag      60
acagtggtga cccaggagcc atccctgaca gtgtctccag gaggaaccgt gacactgacc     120
tgccggagct ccaccggagc agtgaccaca tctaactacg ccaattggtt ccagcagaag     180
cctggccacg cctttacagg cctgatcgga ggcacctcca acagggcacc aggagtgcct     240
gccagattct ctggaagcct gctgggcgac aaggccgccc tgaccctgag cggagtgcag     300
ccagaggatg aggccgagta tttctgtgcc ctgtggtact ccacacacta cgtgttcggc     360
acaggcacca aggtgaccgt gctgggacag cctaaggccg ctcctagcgt gacactgttt     420
cctccaagca gcgaggaact gcaggccaac aaagccacac tcgtgtgcct gatcagcgac     480
ttctatcccg gcgctgtgac agtggcctgg aaggctgata gctctcctgt gaaagccggc     540
gtggaaacca ccacacctag caagcagagc aacaacaaat acgccgccag cagctacctg     600
agcctgacac ctgagcagtg gaagtcccac agatcctaca gctgccaagt gacccacgag     660
ggcagcaccg tggaaaaaac agtggcccct accgagtgca gctga                     705

<210> SEQ ID NO 34
<211> LENGTH: 705
<212> TYPE: DNA
<213> ORGANISM: Artificial Sequence
<220> FEATURE:
<223> OTHER INFORMATION: VL8 of the humanized antibody

<400> SEQUENCE: 34
atgggctggt cctgcatcat tctgtttctg gtggccacag ccaccggcgt gcactctcag      60
acagtggtga cccaggagcc atccctgaca gtgtctccag gaggaaccgt gacactgacc     120

-continued

```
tgccggagct ccaccggagc agtgaccaca tctaactacg ccaattgggt gcaggagaag    180
cctggacacg ccttcacagg actgatcgga ggcacctcca acagggcacc aggagtgcct    240
gcaagatttt ctggaagcct gctgggcgac aaggccgccc tgaccctgag cggagtgcag    300
ccagaggatg aggccgagta tttctgtgcc ctgtggtact ccacacacta cgtgttcggc    360
acaggcacca aggtgaccgt gctgggacag cctaaggccg ctcctagcgt gacactgttt    420
cctccaagca gcgaggaact gcaggccaac aaagccacac tcgtgtgcct gatcagcgac    480
ttctatcccg gcgctgtgac agtggcctgg aaggctgata gctctcctgt gaaagccggc    540
gtggaaacca ccacacctag caagcagagc aacaacaaat acgccgccag cagctacctg    600
agcctgacac ctgagcagtg gaagtcccac agatcctaca gctgccaagt gacccacgag    660
ggcagcaccg tggaaaaaac agtggcccct accgagtgca gctga               705
```

USE OF SUCCINATE AS BIOMARKER IN DIAGNOSIS AND TREATMENT OF CANCERS

CROSS-REFERENCE TO RELATED APPLICATION

This patent application claims the benefit of provisional patent application U.S. Ser. No. 62/916,376 filed Oct. 17, 2019. The contents of U.S. Ser. No. 62/916,376 are expressly incorporated herein by reference thereto.

BACKGROUND OF THE INVENTION

Technical Field of the Invention

The present invention relates to using succinate as a new biomarker for diagnosing or treating cancer. In particular, the present invention relates to a method of treating cancer using an antagonist of succinate, such as an anti-succinate monoclonal antibody or an SUCNR1 inhibitor, and a method of diagnosing cancers by detecting serum succinate level.

Background

The immune system has evolved to discriminate between normal and malignant cells. The activated immune system launches immune response to eliminate damaged and malignant cells to protect the host. According to the classic concept of immunosurveillance, the immune system should prevent tumor initiation and development in health. Indeed, growing evidence suggests that existence of cancer immunosurveillance not only protects host against development of primary cancer but also shapes the immunogenicity of tumors (de Visser et al., 2006; Dunn et al., 2004). However, upon tumor initiation and formation, tumor cells can activate tolerogenic signaling pathways to impair homeostasis of immune system; leading to tumor immune tolerance and escape from classical immune attack. In addition, immune cells, endothelial cells, and fibroblasts are recruited to the tumor microenvironment and activated to become tumor-associated cells, contributing to cancer growth and metastasis.

Within the tumor microenvironment, cancer cells release soluble molecules to not only initiate oncogenic signaling for benefiting growth, survival, and metastasis but also impact the surrounding cells, including the immune cells, for enhancing tumor development. However, the host cells recognize tumor cells as foreign and subjects them for immunological surveillance. Therefore, the dynamic interaction between tumors and the immune system is critical in regulation of tumor initiation and progression. Macrophages, the major population of cells in the tumor microenvironment, play an essential role in the immune homeostasis and defense. Furthermore, they are activated and polarized by the signals in the microenvironment to functionally different phenotypes, i.e., the classically activated (M1) and alternatively activated (M2) macrophages. A large body of evidence suggests that macrophages within the tumor microenvironment are activated by tumor-derived cytokines into M2-polarized tumor-associated macrophages (TAM), promoting tumor progression and suppressing anti-tumor immune response. Cancer cells generate signals that control the functional phenotype of a variety of non-cancerous cells surrounding them to aid tumor development. Understanding the mechanism whereby tumor cells recruit cells into their microenvironment and alter phenotype of surrounding cells might provide more effective treatment strategies.

Cellular metabolite profiles are regarded as important indicators of the physiological or pathological states, e.g., healthy or cancerous. Additionally, endogenous metabolites are implicated in modulating cellular biological processes, such as immune homeostasis and tumor development. In other words, specific metabolites are required to maintain normal physiological processes; conversely, some metabolites induce harmful responses under stress. For example, the tryptophan metabolite kynurenine released by tumor cells promotes cancer cell progression. However, the host cells can release defensive metabolites to suppress tumor progression. For instance, fibroblasts produce and release 5-methoxytryptophan, a novel tryptophan metabolite, into the extracellular milieu to suppress the overexpression of COX-2 and tumorigenesis in a paracrine manner, in vitro and in vivo. Notably, production of this metabolite is suppressed in cancer-associated fibroblasts, suggesting that tumor cells may negate the anti-tumor response by affecting host cell phenotype. It is very likely that cancer cells produce and release endogenous factors to promote tumor progression by suppressing the anti-tumor immune responses.

Therefore, the present invention provides a method of diagnosing cancer by detecting the level of serum succinate as a new cancer biomarker. Also, the present invention further provides a method of treating cancer using an antagonist of succinate, such as an anti-succinate monoclonal antibody or an SUCNR1 inhibitor.

SUMMARY OF INVENTION

Based on the above objects, the present invention discloses that the secreted tumor-derived succinate activate succinate receptor (SUCNR1) signaling to polarize macrophage into tumor-associated macrophages (TAM) and promote tumor metastasis, causing that the level of serum succinate is elevated in cancer patient.

Accordingly, one aspect of the present invention provides an monoclonal anti-succinate antibody, comprising a heavy chain having an amino acid sequence of SEQ ID NO: 2 or 6; and a light chain having an amino acid sequence of SEQ ID NO: 4 or 8.

In some embodiments, the monoclonal anti-succinate antibody is a humanized anti-succinate antibody. In a preferable embodiment, the humanized anti-succinate antibody comprises heavy-chain variable domains VH1-VH5, comprising the amino acid sequence of SEQ ID NOs: 9-13, respectively; and light-chain variable domains VL1-VL8, comprising the amino acid sequence of SEQ ID NOs: 14-21, respectively.

In some embodiments of the present invention, the monoclonal antibody can neutralize serum succinate.

In other embodiment, the monoclonal antibody can inhibit cancer metastasis and the transformation of macrophage into tumor-associated macrophage.

In another embodiment, the monoclonal antibody can inhibit SUCNR1 signaling pathway and suppresses the expression of ARG1.

In some embodiments, the monoclonal antibody has a heavy chain comprising the amino acid sequence of SEQ ID NO: 2 and a light chain comprising the amino acid sequence of SEQ ID NO: 4.

In other embodiments, the monoclonal antibody has a heavy chain comprising the amino acid sequence of SEQ ID NO: 6 and a light chain comprising the amino acid sequence of SEQ ID NO: 8.

In some embodiments, the humanized anti-succinate antibody comprises heavy-chain variable domains VH1-VH5, comprising the amino acid sequences of SEQ ID NOs: 9, 10, 11, 12, and 13, respectively; and light-chain variable domains VL1-VL8, comprising the amino acid sequences of SEQ ID Nos: 14, 15, 16, 17, 18, 19, 20, and 21, respectively.

In other embodiments, the humanized anti-succinate antibody comprises heavy-chain variable domains VH1-VH5, comprising the amino acid sequences encoded by the DNA sequences of SEQ ID NOs: 22, 23, 24, 25, and 26, respectively; and light-chain variable domains VL1-VL8, comprising the amino acid sequences encoded by the DNA sequences of SEQ ID NOs: 27, 28, 29, 30, 31, 32, 33, and 34, respectively.

In other aspect, the present invention relates to a method of treating cancer, comprising administrating an antagonist of succinate to a subject in need of.

In some embodiments, the cancer is a non-small lung cancer, a lung cancer, a prostate cancer, a breast cancer or a colon cancer.

In some embodiments, the antagonist of succinate is an anti-succinate monoclonal antibody.

In other embodiments, the antagonist of succinate is an SUCNR1 inhibitor. In some embodiments, the SUCNR1 inhibitor is a SUCNR1 siRNA.

In another aspect of the present invention, it relates to a method of diagnosing a cancer, comprising detecting serum succinate level in a subject.

In some embodiments, the cancer is a non-small lung cancer, a lung cancer, a prostate cancer, a breast cancer or a colon cancer.

BRIEF DESCRIPTION OF THE DRAWINGS

FIG. 1A-1F show that there is a soluble factor in cancer-conditioned medium inducing TAM marker expression in macrophages. FIG. 1A shows ARG1 protein expression of peritoneal macrophages incubated in control medium, LCC-CM, or A459-CM. FIG. 1B shows Arg1 mRNA expression of peritoneal macrophages incubated in control medium, LCC-CM, or A459-CM. FIG. 1C shows the ARG1 expression level in macrophages treated with control medium or PC3-CM. FIG. 1D shows Arg1 mRNA expression of macrophages incubated in control medium or conditioned medium collected from MCF-7 (MCF7-CM) or HT-29 (HT29-CM) for 24 h. FIG. 1E shows the Arg1, Fizz1, and Mgl1 mRNA expression in peritoneal macrophages cultured with SCM or PCM for 24 h. FIG. 1F shows VCAM1$^+$ CD11c$^+$CD11b$^{low}$-macrophage population in macrophages cultured in control medium, LLC-CM, LLC-SCM or LLC-PCM for 3 days.

FIG. 2A-2E exhibit that the identification of succinate from the small molecular fraction of lung cancer-conditioned medium. FIG. 2A shows the score plot of PCA based on LC-MS spectra of control medium and LLC-SCM. FIG. 2B shows the S-plot generated from OPLS-DA. FIGS. 2C and 2D show the representative mass spectra (Retention time 1.8 min, m/z 50-400) of LLC-CM, A549-SCM, control medium DMEM or pure succinate. FIG. 2E shows the analysis of daughter profiles of m/z 117.0 of LLC-SCM MS1 spectra versus that of pure succinate by LC-MSMS (MS2).

FIG. 3A shows the succinate concentrations in control medium, LLC-CM, A549-CM, PC3-CM, MCF-7-CM, HT-29-CM or peritoneal macrophage-CM. FIG. 3B shows the succinate concentration in the primary subcutaneous tumors excised from C57BL/6J mice subcutaneously injected with LLC cells.

FIG. 4A shows ARG1 expression in macrophages treated with different concentrations of succinate for 24 h. FIG. 4B shows mRNA expression of Arg1, Fizz1, Mgl1, and Mgl2 in macrophages cultured with succinate (1 mM) for 24 h. FIG. 4C shows the VCAM1$^+$CD11c$^+$CD11b$^{low}$-TAM population in macrophages stimulated with succinate (1 mM) for 3 days. FIG. 4D indicates the percentage of TAMs population in primary subcutaneous tumors obtained from LLC injected mice subsequently received intraperitoneal injection of succinate (20 and 100 mg/kg).

FIG. 5A-5D show the clinical relevance of serum succinate and tumor SUCNR1 in non-small cell lung cancer (NSCLC). FIG. 5A shows SUCNR1 mRNA expression level in tumor-free lung tissues and lung cancer tissues. FIG. 5B shows serum succinate concentrations in mice before and 16 days after LLC inoculation. FIG. 5C shows serum succinate concentrations in healthy subjects and patients with NSCLC. FIG. 5D shows the analysis of the discriminative power of serum succinate in NSCLC patients by AUROC curve.

FIG. 6A-6C show that the ability of anti-succinate antibody to neutralizing succinate and its specificity. FIG. 6A shows the specificity of anti-succinate antibody. FIG. 6B shows the succinate levels in LLC-CM or A549-CM incubated with different concentrations of anti-succinate antibodies. FIG. 6C shows migration assay results of LLC cells treated with control IgG or anti-succinate antibody (Succ Ab) for 24 h.

FIG. 7A shows ARG1 expression level in LLC-CM-treated PMφs incubated with control IgG or anti-succinate antibody for 24 h. FIG. 7B shows VCAM1$^+$CD11c$^+$CD11b$^{low}$-TAM population of anti-succinate antibody or control IgG pretreated PMφs stimulated with succinate (1 mM) for 3 days. FIG. 7C shows migration assay results of macrophages treated with succinate (1 mM) with or without control IgG, anti-succinate antibodies for 24 h. FIG. 7D-7F show TAM polarization level, nodule numbers, and the survival time of LLC tumor-bearing C57BL/6J mice treated with 6G10F6 monoclonal antibodies (1 and 5 mg/kg) or IgG control antibodies (5 mg/kg).

FIG. 8 shows the DNA and amino acid sequence of antibody 6G10F6.

FIG. 9 exhibits the DNA and amino acid sequence of antibody 6G10G5.

FIG. 10 shows the cloning strategy of humanizing 6G10F6 monoclonal antibody.

FIG. 11 shows the homology modeling of mouse monoclonal antibody Fv fragments.

FIG. 12A-12C exhibit binding confirmation of 6G10F6 chimeric antibody. FIG. 12A shows the SDS-PAGE analysis of 6G10F6 chimeric antibody, wherein lane M1 is protein marker, TaKaRa, Cat. No. 3452, lane 1 is reducing condition, and lane 2 is non-reducing condition, and western blot analysis of 6G10F6 chimeric antibody, wherein lane M2 is protein marker, GenScript, Cat. No. M00521, lane P is human IgG1, Kappa (Sigma, Cat. No. I5154) as a positive control, lane 1 is reducing condition, and lane 2 is non-reducing condition. FIG. 12B-12C show the affinity measurement of chimeric antibody.

FIG. 13 shows the affinity ranking of humanized antibodies by using Biacore.

FIG. 14A exhibits the result of selected antibody under non-reducing conditions and reducing conditions. FIG. 14B shows the purity and yields of purified IgGs.

FIG. 15A shows the results of 1:1 interaction model by using Biacore. FIG. 15B shows the antigen-binding affinities to the parent chimeric antibody.

FIG. 16A-16B shows the thermo-stability assessment of selected antibodies against antigen. All antibodies are treated for one month up to two months at −80° C., 4° C., 25° C., and 40° C. FIG. 16A shows the results of 4 purified antibodies. FIG. 16B shows the results of 9 crude IgG samples.

FIG. 17A-17E indicate that SUCNR1 is required for succinate-induced macrophage polarization. FIG. 17A shows the fold change of VCAM1$^+$CD11c$^+$CD11b$^{low}$-TAMs in succinate-induced macrophage treated with control IgG and anti-SUCNR1 antibody for 1 h. FIGS. 17B and 17C show Sucnr1 mRNA expression and SUCNR1 protein level in macrophages transfected with scrambled control siRNA, mouse SUCNR1 siRNA-278, -559, or -758 for 48 h. FIG. 17D shows Arg1, Fizz1, Mgl1, and Mgl2 mRNA expression in macrophages in macrophages scrambled control siRNA, mouse SUCNR1 siRNA-278, -559, or -758 for 16 h. FIG. 17E shows the VCAM1$^+$CD11c$^+$CD11b$^{low}$-TAM population in succinate-induced macrophages treated with different siRNA.

FIG. 18A shows the migration assay results of macrophages cultured with control medium (DMEM) or CM from A549 (A549-CM). FIG. 18B shows the migration assay results of macrophages cultured with control medium (DMEM) or A549-CM in the presence or absence of control IgG or anti-SUCNR1 antibody. FIG. 18C shows migration assay results of macrophage treated with different concentrations of succinate. FIG. 18D shows migration assay results of macrophages treated with succinate (1 mM) with or without control IgG or anti-SUCNR1 antibody. FIG. 18E shows the migration assay results of PDGF and different concentrations of succinate at the bottom chamber.

FIG. 19A shows migration and invasion assay results of LLC cells treated with different concentrations of succinate. FIGS. 19B and 19C show migration and invasion assay results of A549, HT-29, MCF-7, and PC3 cells treated with different concentrations of succinate. FIG. 19D shows the E-cadherin, N-cadherin, and vimentin expression level in A549 cells treated with vehicle or succinate (0.5, 1 and 2.5 mM) for 24 h. FIG. 19E shows the E-cadherin, N-cadherin, and vimentin expression level in A549 cells treated with vehicle or succinate (1 mM) for the indicated time periods. FIG. 19F shows the migration assay results of A549 cells treated with succinate with or without metformin (2 mM) for 24 h.

FIG. 20A shows the lung excised from tumor-bearing C57BL/6J mice and metastatic nodules are counted.

FIGS. 20B and 20C show the metastatic nodules in liver, spleen and adrenal gland excised from tumor-bearing C57BL/6J mice.

FIGS. 21A and 21B show the migration assay results and IL-6 level in monocultured LLC and LLC co-cultured with succinate-polarized macrophages. FIGS. 21C and 21D show the migration assay results and IL-6 level in monocultured LLC and LLC co-cultured with succinate-polarized macrophages added with anti-IL-6 neutralizing antibody or control IgG (2.5 μg/ml). FIG. 21E shows IL-6 level in LLC cells co-cultured with macrophages transfected with scrambled control siRNA (sc) or SUCNR1 siRNA-758.

FIG. 22A shows ERK1/2, and phospho-ERK1/2 expression level in A549/shNC and A549/shSUCNR1 cells treated with succinate (1 mM) for the indicated time periods. FIGS. 22B and 22C show the intracellular calcium level and conditioned medium PGE2 level in LC/shNC, LLC/shSUCNR1, A549/shNC, and A549/shSUCNR1 cells treated with succinate (1 mM) for 2 h.

FIG. 23A shows the migration assay results of LLC, A549, PC3, and HT-29 cells treated with succinate (1 mM) with or without control IgG or anti-SUCNR1 antibody. FIG. 23B shows the invasion assay results of LLC and HT-29 cells treated with succinate (1 mM) with or without control IgG or anti-SUCNR1 antibody.

FIG. 24A shows the SUCNR1 expression levels in different A549 stable clones with expressing shSUCNR1 (A549/shSUCNR1) or shNC (A549/shNC). FIG. 24B shows migration and invasion assay results of succinate-stimulated (1 mM for 24 h) A549 cells stably transfected with control shRNA (A549/shNC) or SUCNR1 shRNA (A549/shSUCNR1). FIG. 24C shows Sucnr1 mRNA level in LLC cells stable clones with expressing shSUCNR1 (LLC/shSUCNR1). FIG. 24D shows the migration assay results of LLC and LLC/shSUCNR1 cells stimulated with succinate (1 mM) for 24 h. FIG. 24E shows the evaluation of lung metastatic nodules in A549/shNC or A549/shSUCNR1 injected mice received an intraperitoneal injection of succinate (100 mg/kg) twice weekly for 8 weeks. FIG. 24F shows the evaluation of lung metastatic nodules in LLC or LLC/shSUCNR1 cell injected mice received an intraperitoneal injection of succinate (100 mg/kg) twice weekly for 8 weeks.

FIG. 25A-25E show that effect of succinate on HIF-1α and kinase phosphorylation in A549 and LLC cells. FIG. 25A shows the HIF-1α, Akt, phospho-Akt, AMPK, phospho-AMPK, p38 MAPK, and phospho-p38 MAPK expression level in A549 and LLC cells treated with succinate (1 mM) for the indicated time periods. FIG. 25B shows the Hif-1α mRNA level in LLC cells treated with succinate (1 mM) for the indicated time periods. FIG. 25C shows the Hif-1α mRNA level in LLC cells treated with different concentrations of LY294002 or SB202190 for 12 h. FIG. 25D shows the Hif-1α mRNA level in LY294002 or SB202190-pretreated LLC cells treated with succinate (1 mM) for 12 h. FIG. 25E shows the Hif-1α mRNA level in A549/shNC and A549/shSUCNR1 cells treated with succinate (1 mM) or dimethyl-ester succinate (DMS, 20 mM) for 12 h.

7 8

Figures 26A, 26B, 26C, 26D:
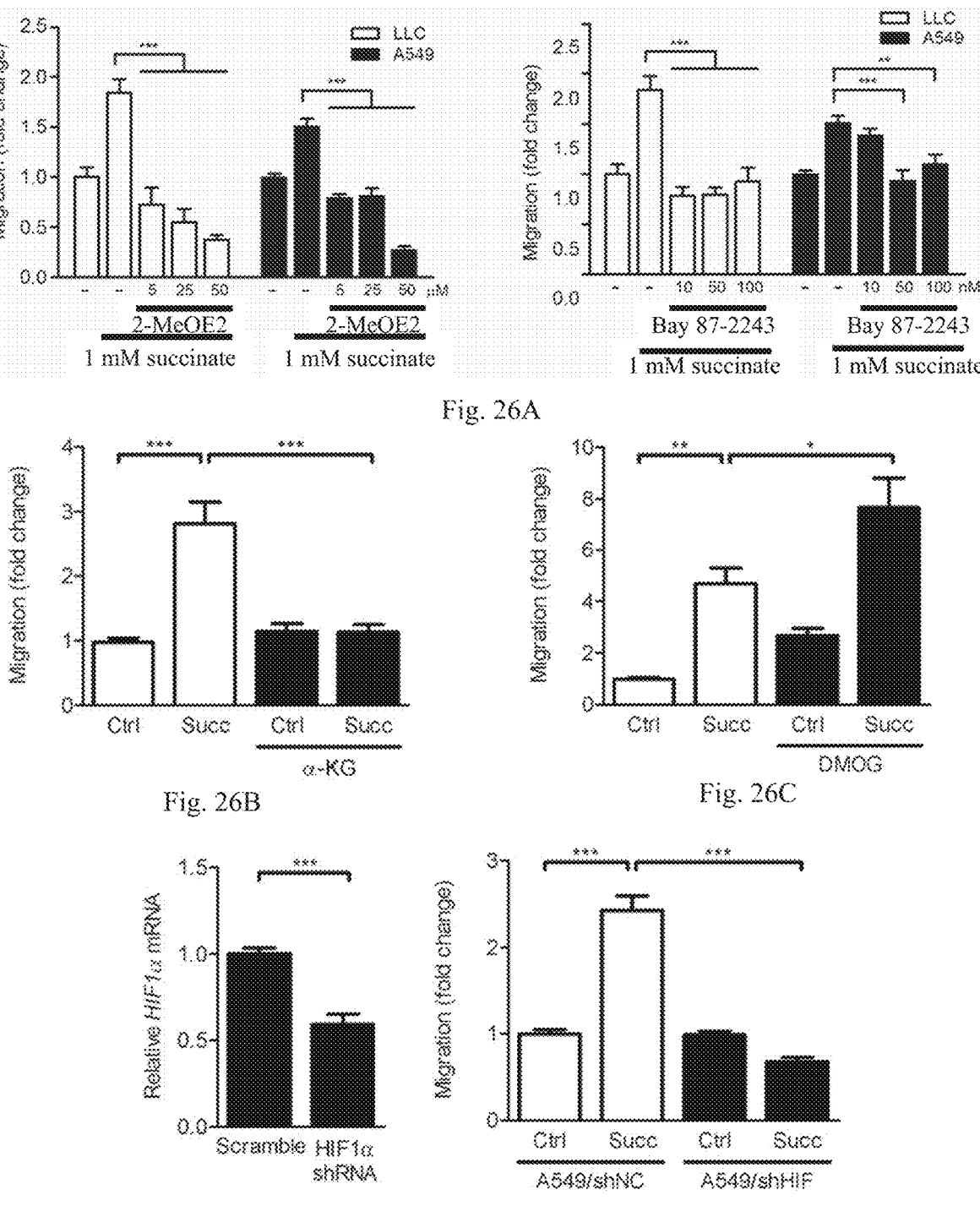
Figure 26E:
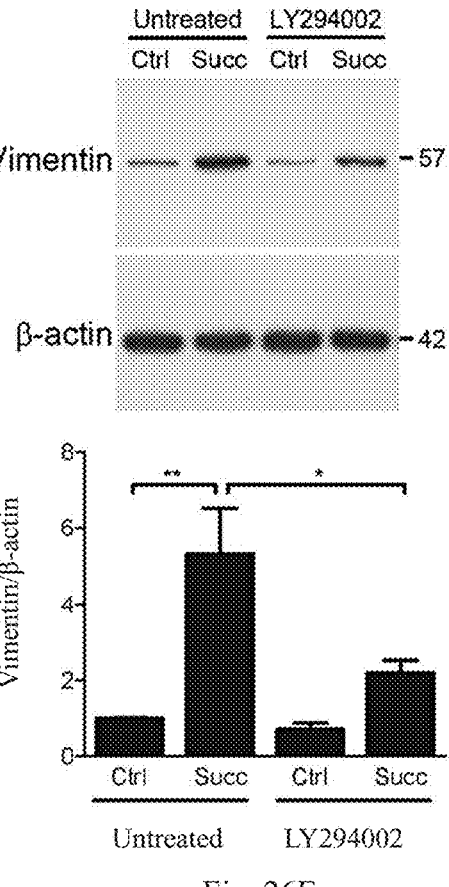
Figure 26F:
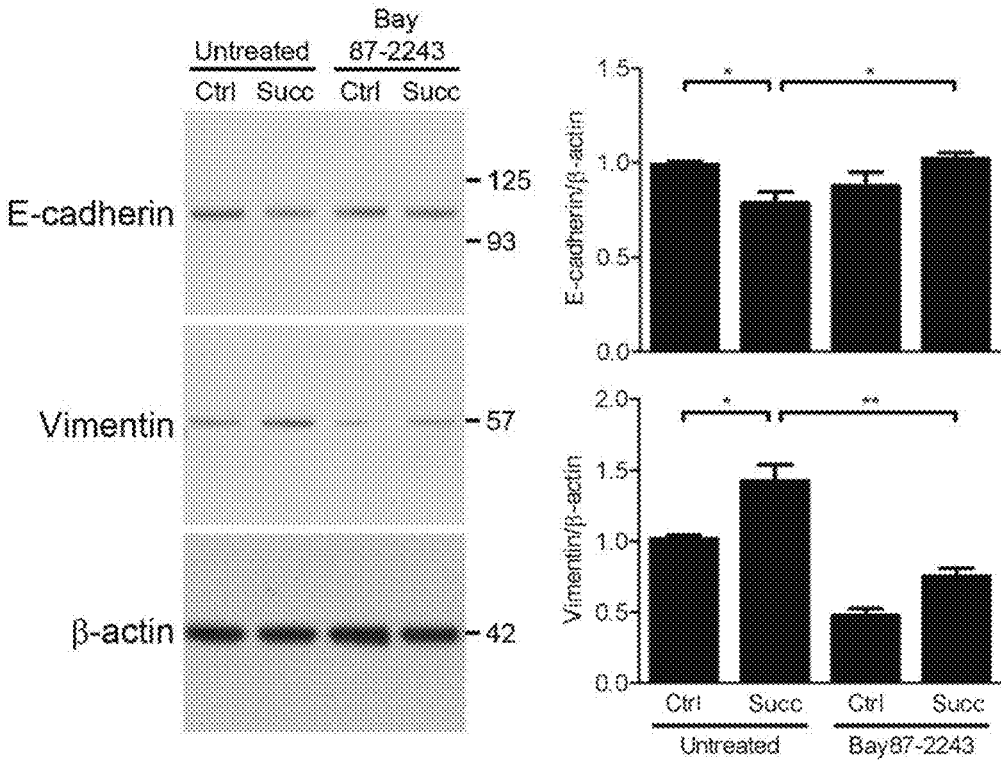

FIG. 26A-26F exhibit PI3K-mediated HIF-1α upregulation is crucial for succinate-induced cancer migration and EMT. FIG. 26A shows migration assay results of LLC and A549 cells treated with succinate with or without various concentrations of HIF-1α inhibitors, 2-MeOE2 and Bay 87-2243, for 24 h. FIGS. 26B and 26C show migration assay results of A549 cells treated with succinate (1 mM) with or without α-KG (1 mM) or DMOG (200 μM) for 24 h. FIG. 26D shows the HIF-1α mRNA level in A549/shNC or A549/HIF-1α cell and the migration assay results of A549/shNC or A549/HIF-1α cells treated with or without succinate (1 mM). FIGS. 26E and 26F shows the E-cadherin and Vimentin expression level in LY294002 or Bay 87-2243-pretreated A549 cell treated with vehicle or succinate (1 mM) for 24 h.

Figures 27A, 27B:
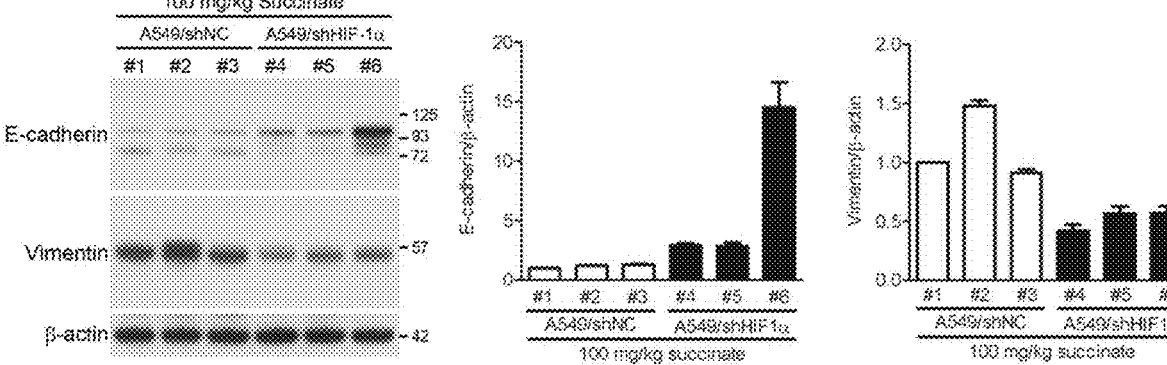

FIG. 27A-27B show the role of HIF-1α in succinate-induced metastasis in vivo. FIG. 27A shows the lung metastatic nodules evaluation in A549/shNC or A549/HIF-1α injected mice received an intraperitoneal injection of succinate (100 mg/kg) twice weekly for 8 weeks. FIG. 27B shows the levels of E-cadherin and Vimentin in total protein extracted from primary subcutaneous tumor of A549/shNC or A549/shHIF1-α.

DETAILED DESCRIPTION OF THE INVENTION

Other features and advantages of the present invention will be further exemplified and described in the following examples, which are intended to be illustrative only and not to limit the scope of the invention.

Example 1. Cancer Cell-Derived Succinate Induces Macrophage Polarization

Soluble Factor in Cancer-Conditioned Medium Induces TAM Markers in Macrophage

Figure 1E:
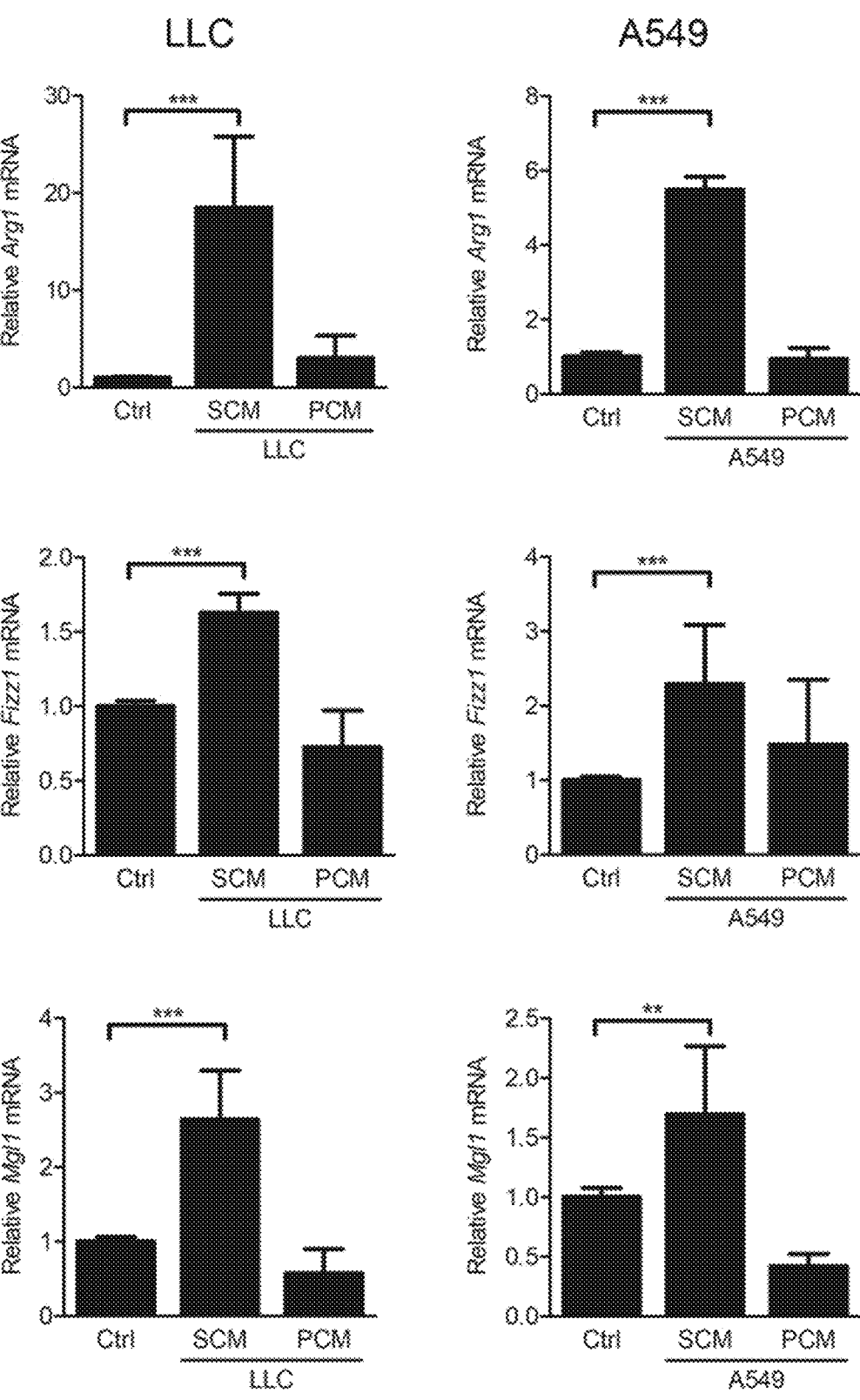

Peritoneal macrophages are incubated in control medium or conditioned medium (CM) collected from LLC (LLC-CM) or A549 (A549-CM) for 24 h. ARG1 protein and Arg1 mRNA in macrophages are measured by immunoblot analyses and qPCR, respectively. CM collected from human prostate cancer PC3 cells is cultured in RPMI1640 medium supplemented with 10% FBS for 24, 48 and 72 hours and incubated with peritoneal macrophages. Cell lysates from macrophages treated with control medium or PC3-CM for 24 hours are immunoblotted with antibodies for ARG1 or β-actin. Experiments are repeated 3 times with similar results. Compared with control medium, the macrophage ARG1 protein and mRNA levels are increased in the CM of lung cancer cell lines (murine LLC and human A549) (FIGS. 1A and 1B) while CM of human prostate cells (PC3) also induces macrophage ARG1 protein to a similar extent (FIG. 1C). On the other hand, peritoneal macrophages are incubated in control medium or conditioned medium collected from MCF-7 (MCF7-CM) or HT-29 (HT29-CM) for 24 hours. Arg1 mRNA in macrophages is measured by qPCR. And CM of human breast cancer cells (MCF-7) and colon cancer cells (HT-29) also raises the expression of Arg1 and other TAM markers, such as Fizz1 and Mgl1 mRNA (FIG. 1D). These results suggest that the presence of endogenous molecules mediates the conversion of macrophages into TAM.

Figure 1F:
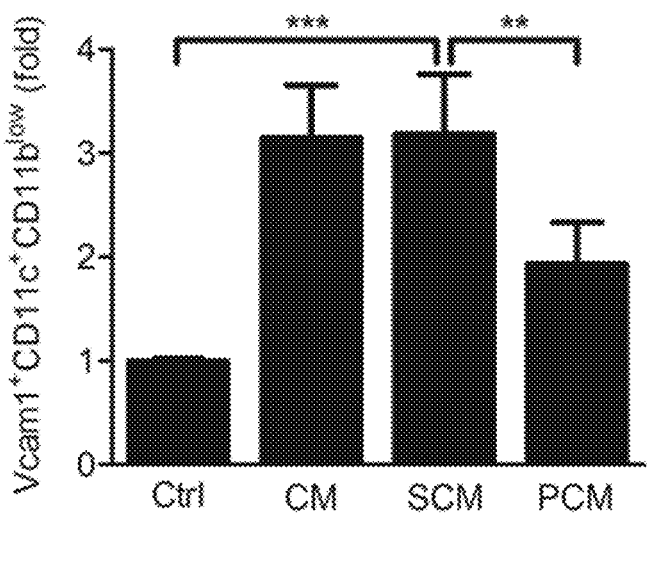

To identify the active molecules, LLC-CM and A549-CM are fractionated into SCM with small molecular (<3 kDa) and PCM with protein-peptide fraction (>3 kDa). Arg1, Fizz1, and Mgl1 mRNA in peritoneal macrophages cultured with SCM or PCM for 24 hours are analyzed by qPCR. And peritoneal macrophages are cultured in control medium, LLC-CM, LLC-SCM or LLC-PCM for 3 days. CM of LLC (LLC-CM) and A549 (A549-CM) are fractionated according to size (<3 kDa and >3 kDa), and its effect on macrophage Arg1 expression is also evaluated. The small molecular fraction (<3 kDa, SCM) not only up-regulates the expression of Arg1, Fizz1, and Mgl1, but also increases the population of VCAM1$^+$CD11c$^+$CD11b$^{low}$-TAMs, but the protein-peptide fraction (>3 kDa, PCM) does not show the same effects (FIGS. 1E and 1F) (VCAM1$^+$CD11c$^+$CD11b$^{low}$-macrophage population was measured by flow cytometry and normalized to the cell number of control medium treatment. Data represent mean±SEM of 3 independent experiments. P<0.005; *P<0.0005).

Figure 2A:
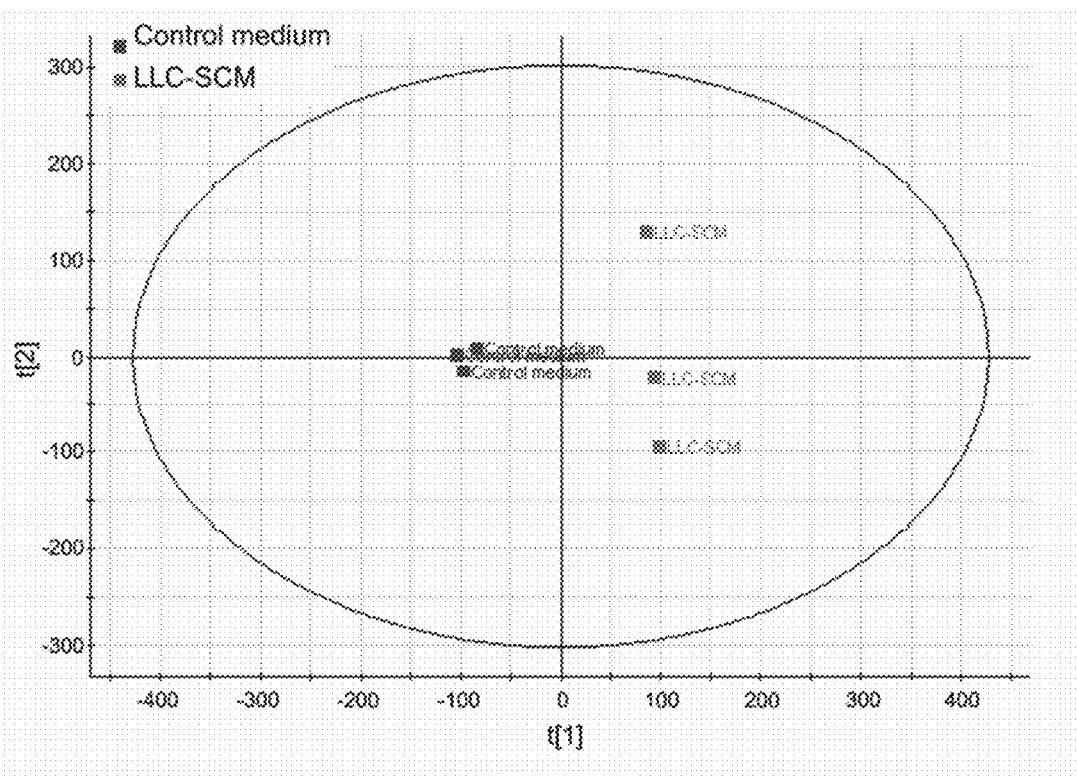
Figure 2B:
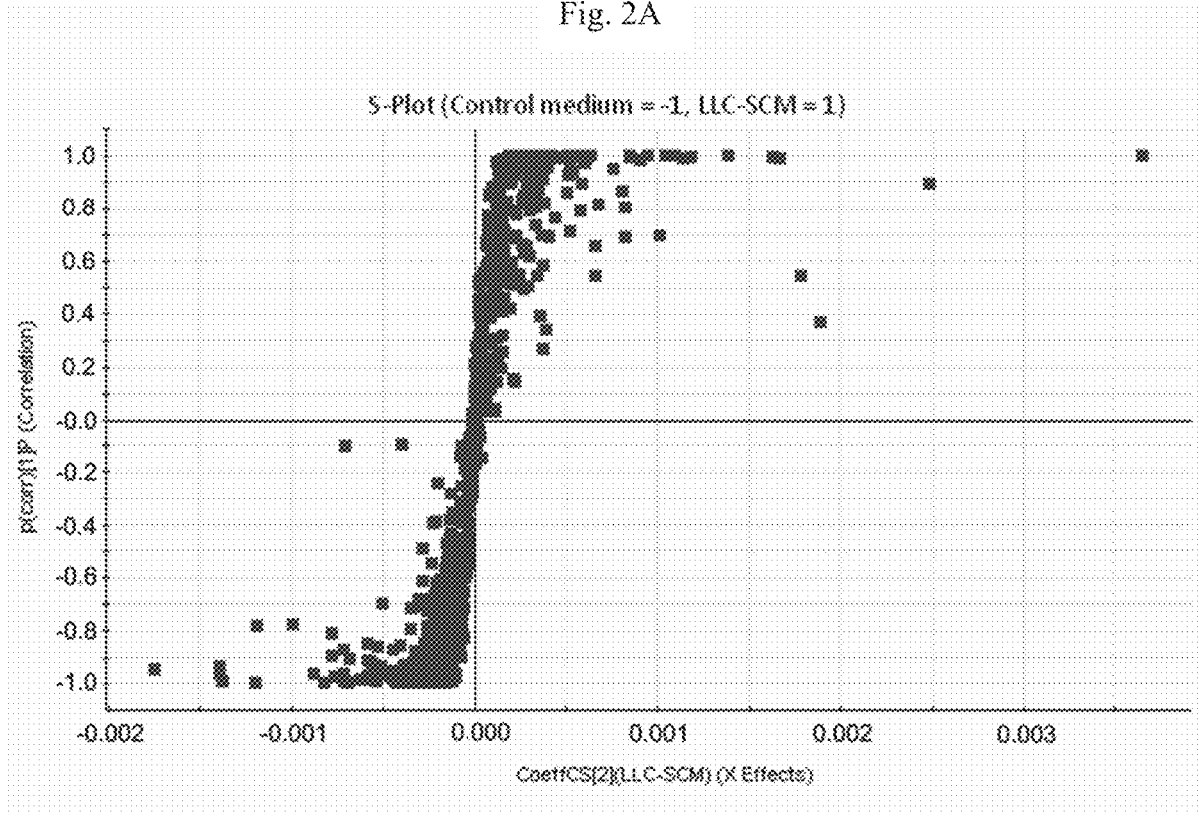
Figure 2E:
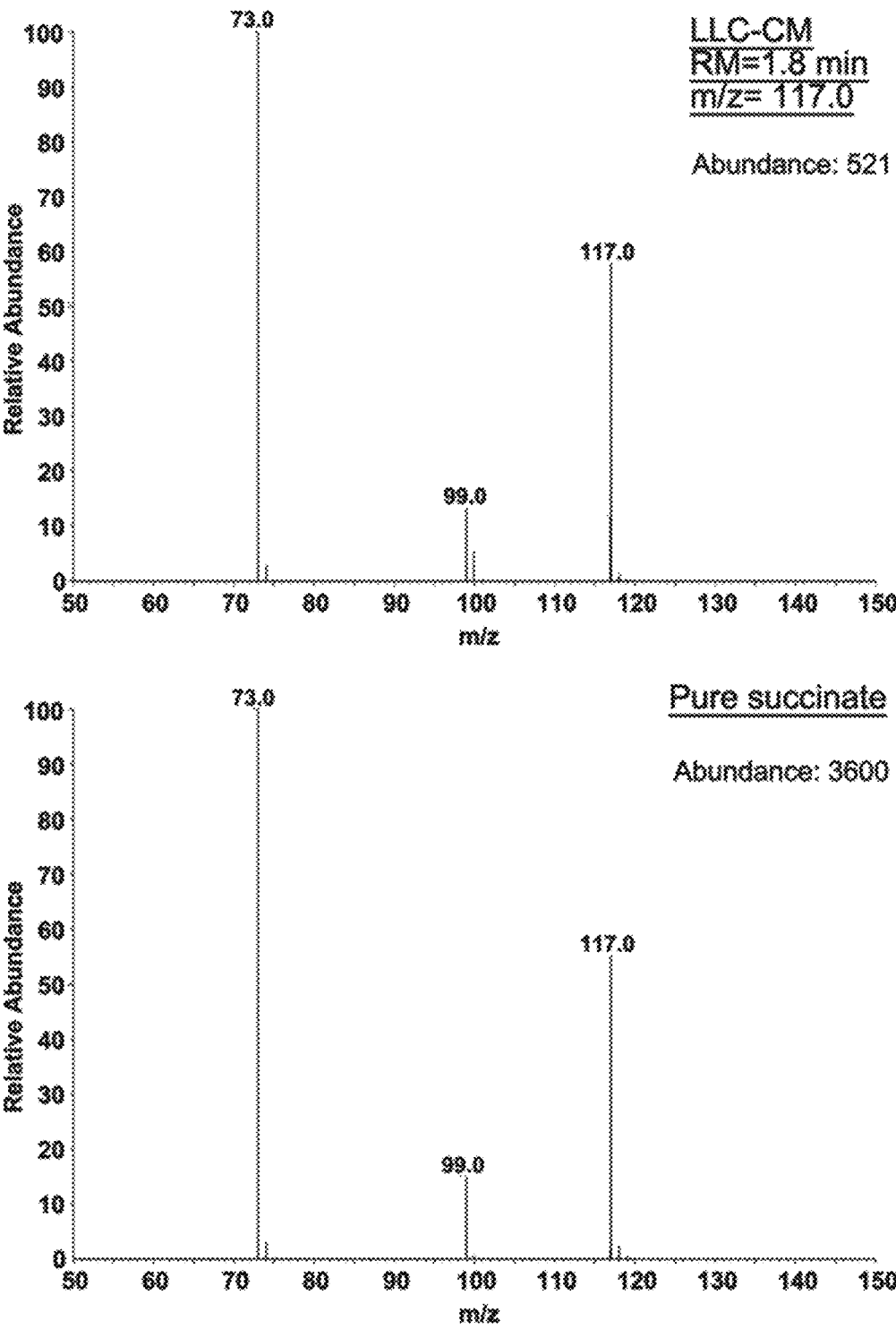

Next, LC-MS is used to identify the soluble molecules in LLC-SCM and A549-SCM. Principal component analysis (PCA) shows a clear separation of component distribution between LLC-SCM and control medium (FIG. 2A), indicating differences in metabolite composition between these two groups. To identify metabolites derived from cancer, S-plot is constructed from an orthogonal partial least-squares discriminant analysis (OPLS-DA) model. Base on the S-plot, 11 LLC-derived metabolites are identified that they show significant fold change and large value of both p(corr)[1] and CoeffCS (greater than 0.001) (FIG. 2B and Table 1). By in-house metabolite database search and pure compounds validation, three LLC-derived metabolites are identified as succinate, lactate, and citrate. The chemical identity of the remaining 8 metabolites remained unknown at the present time. Furthermore, analysis of the mass spectra reveals striking differences between cancer cell-SCM and the control medium. A major m/z 117.0 peak is observed in LLC-SCM (FIG. 2C) and A549-SCM (FIG. 2D) but not in control medium (retention time 1.8 min, m/z 50-400). The daughter ion profile of m/z 117.0 matches that of pure succinate (FIG. 2E).

TABLE 1

Metabolites in LLC-SCM identified by S-plot from an OPLS-DA have higher intensities than control medium.

| ID | Retention Time (min) | Mass | p[1]P | p(corr)[1]P | CM ion intensity | LLC-CM ion intensity | Fold change | Metabolite name |
|---|---|---|---|---|---|---|---|---|
| 1 | 1.41 | 128.0 | 0.20 | 0.54 | 1949.95 | 3338.91 | 1.70 | |
| 2 | 1.80 | 117.0 | 0.35 | 1.00 | 357.20 | 2717.98 | 7.60 | Succinate |
| 3 | 1.26 | 89.0 | 0.15 | 0.37 | 589.59 | 1726.79 | 2.90 | Lactate |
| 4 | 2.66 | 129.0 | 0.23 | 0.89 | 10.86 | 1160.43 | 106.90 | |
| 5 | 1.26 | 191.0 | 0.16 | 0.99 | 21.96 | 517.07 | 23.60 | |
| 6 | 2.78 | 129.0 | 0.16 | 0.99 | 42.33 | 516.42 | 12.20 | |

TABLE 1-continued

Metabolites in LLC-SCM identified by S-plot from an OPLS-DA have higher intensities than control medium.

| ID | Retention Time (min) | Mass | p[1]P | p(corr)[1]P | CM ion intensity | LLC-CM ion intensity | Fold change | Metabolite name |
|---|---|---|---|---|---|---|---|---|
| 7 | 1.82 | 257.0 | 0.13 | 1.00 | 2.67 | 341.19 | 127.60 | |
| 8 | 1.47 | 191.0 | 0.11 | 0.69 | 0.00 | 312.12 | 10000 | Citric acid |
| 9 | 1.80 | 73.0 | 0.11 | 1.00 | 29.73 | 279.26 | 9.40 | |
| 10 | 2.61 | 573.1 | 0.11 | 1.00 | 58.39 | 270.38 | 4.60 | |
| 11 | 1.24 | 231.9 | 0.10 | 1.00 | 17.12 | 211.08 | 12.30 | |

Figure 3A:
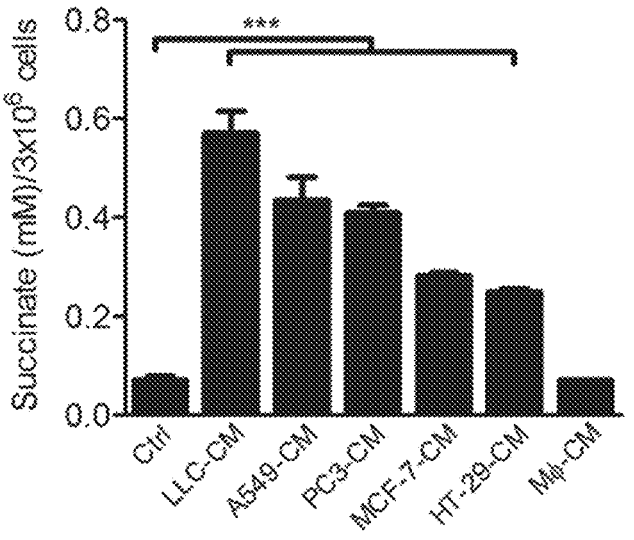
FIG. 3A-3B indicate that the concentrations of succinate in different cancer cell conditioned mediums and primary subcutaneous tumors.
Figure 3B:
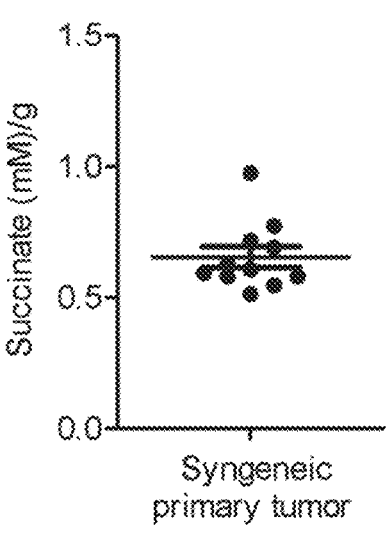

To confirm the presence of succinate in cancer cell-CM, Succinate Colorimetric Assay Kit is conducted to analyze succinate in the CM. The results show that there are comparable amounts of succinate detected in LLC-CM (0.57 mM), A549-CM (0.43 mM), PC3-CM (0.41 mM), MCF-7-CM (0.28 mM), and HT-29-CM (0.25 mM) (FIG. 3A). A low quantity of succinate is detected in macrophage-CM (0.07 mM) and fresh control medium (0.07 mM). These results suggest that succinate is the major metabolite in cancer-CM that drives macrophage polarization. And C57BL/6J mice are also subcutaneously injected with LLC cells for 21 days for inducing tumors. The tumors are excised and conducted with further analysis showing that succinate concentration in subcutaneous tumors is 0.65±0.039 mM (n=11, and the data represents mean±SEM, ***P<0.0005) (FIG. 3B). It shows that cancer cells release succinate into the extracellular milieu, which may account for TAM markers up-regulation and TAM polarization.

Cancer Cell-Derived Succinate Induces Macrophage Polarization

Figures 4A, 4B:
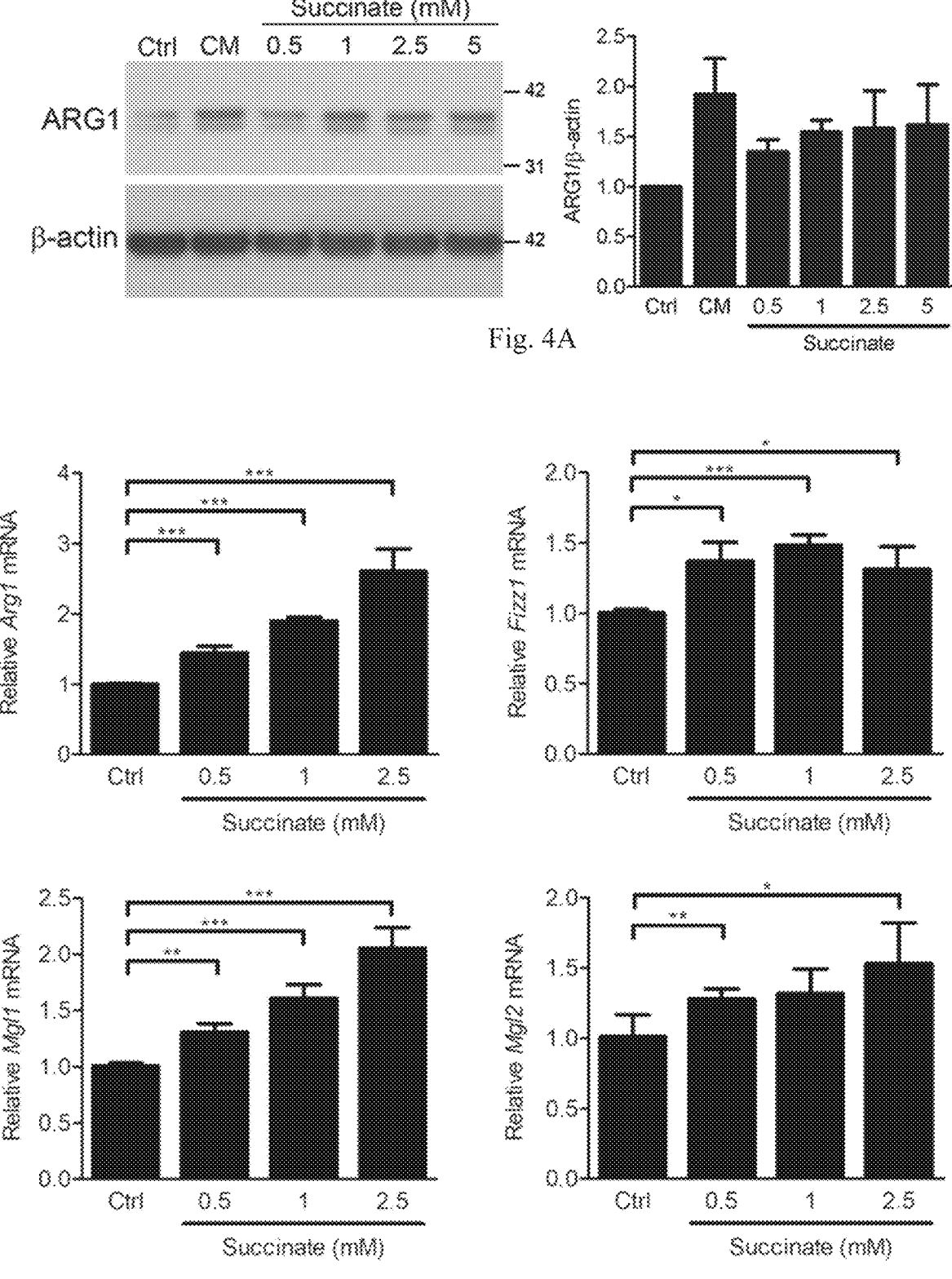
FIG. 4A-4D show that succinate promotes macrophage polarization into TAM.
Figure 4C:
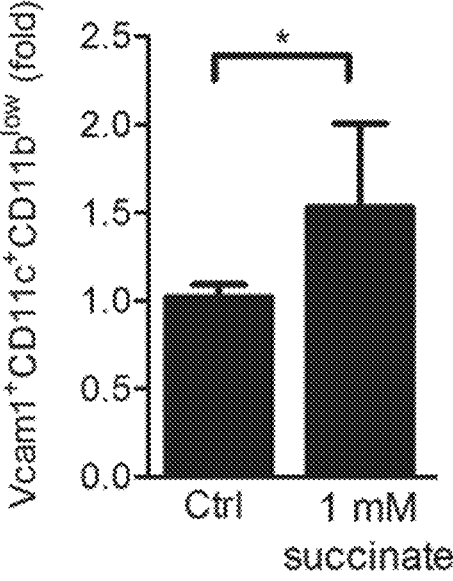
Figure 4D:
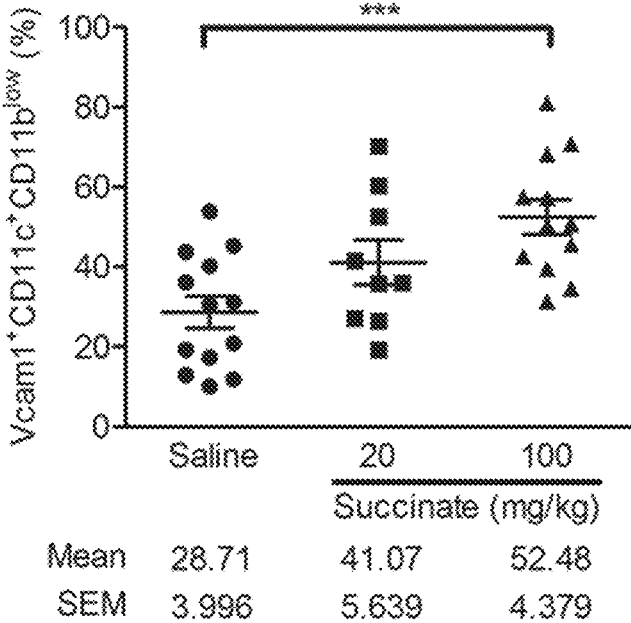

Mouse peritoneal macrophages are treated with succinate and the expression level of TAM markers is detected. The results reveal that succinate increases the expression of ARG1 protein in mouse peritoneal macrophages in a concentration-dependent manner (FIG. 4A). Furthermore, analysis of transcripts of TAM-specific genes in peritoneal macrophages shows that succinate raises the expression of TAM marker gene, including Arg1, Fizz1, Mgl1, and Mgl2, in a dose-dependent manner (FIG. 4B). In addition, succinate also up-regulates TAM surface markers including CD11c and VCAM1 (VCAM1$^+$CD11c$^+$CD11b$^{low}$) (FIG. 4C). It suggests that succinate polarizes the macrophage population to VCAM1$^+$CD11c$^+$CD11b$^{low}$-TAMs. A syngeneic murine tumor model of LLC is used to evaluate the effect of succinate on TAM polarization in vivo. LLC cells are subcutaneously injected into C57BL/6J mice, which subsequently receive an intraperitoneal injection of succinate (20 and 100 mg/kg) or a vehicle, twice a week for 3 weeks. On day 21, primary subcutaneous tumors are harvested, and percentage of TAMs is analyzed. The percentage of TAMs population in primary subcutaneous tumors obtained from a different mouse in each group (saline n=11; 20 mg/kg succinate n=8; 100 mg/kg succinate n=10) are analyzed by flow cytometry (data represent mean±SEM of 3 experiments, *P<0.05; P<0.005; *P<0.0005). The primary subcutaneous tumors in succinate-treated mice contain a significantly higher number of VCAM1$^+$CD11c$^+$ CD11b$^{low}$-TAMs than saline-treated mice (FIG. 4D). Collectively, it indicates that succinate promotes functional polarization of TAMs.

Example 2. Serum Succinate is Used as a Diagnostic Biomarker of Cancers

Succinate Receptor Expression is Elevated in Human Lung Cancer

To provide clinical relevance regarding SUCNR1, the receptor mRNA level in 213 human lung cancer tissues and 78 tumor-free lung tissues are analyzed by qPCR (Table 2). Mean receptor mRNA level in lung cancer tissues was significantly higher than that in tumor-free lung tissues (FIG. 5A). The receptor mRNA level in lung cancer tissues had wide distribution and a considerable number (37.56%) was higher than normal values (FIG. 5A). We wondered if tumor SUCNR1 level correlates with survival of lung cancer patients. These results suggest that tumor SUCNR1 level contributes to the tumor promoting activity of succinate.

TABLE 2

Patient demographics for the analysis of SUCNR1

| | Tumor-free (n = 78) | Lung tumor tissues (n = 213) |
|---|---|---|
| Age (years) | | |
| Median | 65 | 66 |
| IQR | 60-71 | 60-74 |
| Gender | | |
| Male | 44 | 131 |
| Female | 34 | 81 |
| Not specified | 0 | 1 |

Results are presented as number of patients.
IQR, interquartile range.

Serum Succinate is a Potential Biomarker of Lung Cancer

C57BL/6J mice are injected with LLC cells and analyzed for evaluating the succinate level in mice serum before and after inoculation of LLC cells. Succinate is detected in mice before LLC injection (mean 0.19±0.037 mM, n=7), which is increased 16 days after LLC inoculation (mean 0.36±0.059 mM, mice with 177.6 mm³ tumor, n=7) (FIG. 5B). These results indicate that serum succinate level is elevated in tumor-bearing mice. To determine the clinical relevance of serum succinate, the succinate levels in the serum of 21 healthy subjects and 97 NSCLC patients are measured (Table 3). Mean serum concentration of succinate in lung cancer patients (0.53±0.038 mM) is significantly higher than that of health subjects (FIG. 5C), suggesting that elevated serum succinate levels in patients with NSCLC may reflect cancer development and may be a marker of cancer pro-

Figure 5D:
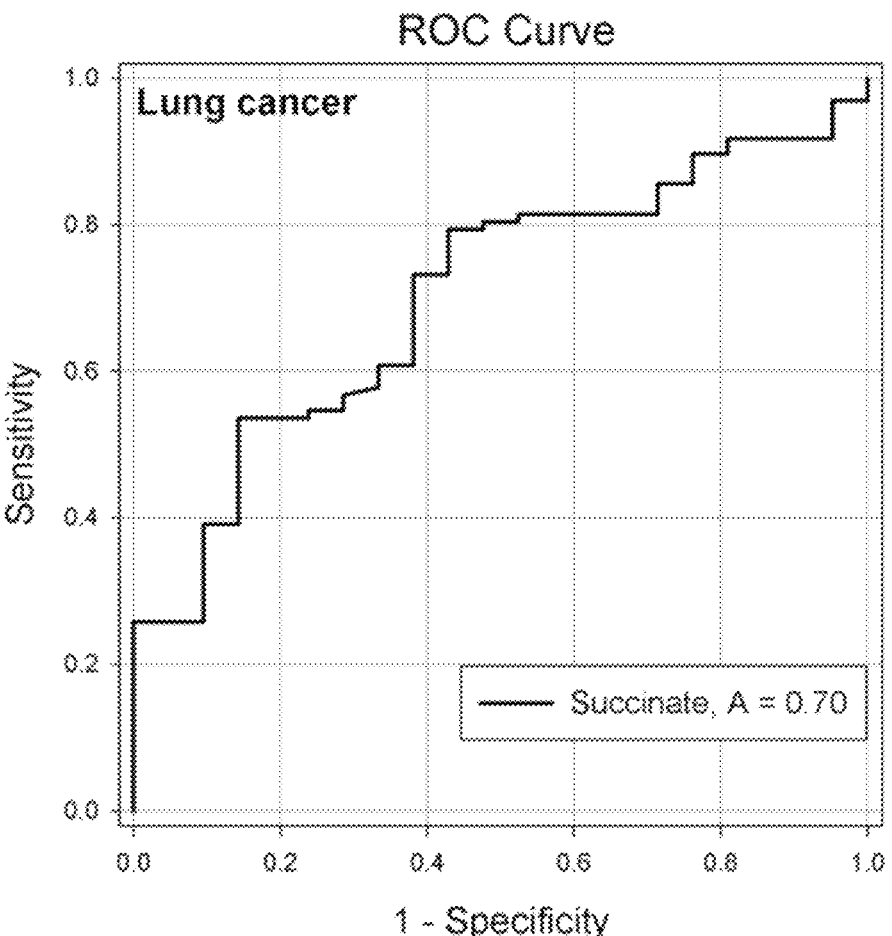

11 gression. Furthermore, area under the receiver operating characteristic (AUROC) curve is used to determine the discriminative power in this group of patients (FIG. 5D). The AUC for succinate is 0.70 (95% CI: 0.594-0.813, p=0.0036). The cutoff level of succinate with the optimum diagnostic efficiency derived from the AUROC curves is 0.34 mM (53.61% sensitivity, 85.71% specificity). The AUROC analysis reveals that serum succinate has a higher predictive value for NSCLC patients. Taken together, these results indicate that serum succinate could serve as a predictive biomarker of patients with NSCLC.

TABLE 3

Patient demographics for the analysis of serum succinate

|  | Healthy donor (n = 21) | Lung cancer patients (n = 97) |
|---|---|---|
| Age (years) | | |
| Median | 58 | 63 |
| IQR | 51-62 | 58-69 |
| Gender | | |
| Male | 7 | 41 |
| Female | 14 | 56 |

Results are presented as number of patients.
IQR, interquartile range.

Example 3. Development and Therapeutic Effect of the Monoclonal Anti-Succinate Antibody Developing Monoclonal Succinate Antibody as Anti-Cancer Therapeutic Antibody Given that cancer cells secret succinate into the tumor microenvironment to promote TAM polarization and cancer metastasis, and that serum succinate level in patients with lung cancer is significantly increased, the possibility of neutralizing serum succinate by anti-succinate antibodies to suppress tumorigenesis is examined. To address this, succinate conjugated carrier peptide is generated as antigen to generate polyclonal succinate antibody and evaluate its effect on LLC migration. Succinic acid-BSA conjugate is used to immunize New Zealand Rabbit. At 3rd immunization, antiserum is preabsorbed on protein carriers and purified by protein A column (GenScript). Using a succinate-KLH (Lysine-Leucine-Histidine) conjugate, the antibody specificity is analyzed with an indirect ELISA (GenScript) (FIG. 6A). In addition, to confirm that anti-succinate antibodies neutralize succinate in cancer-CM, succinate level in cancer-CM treated with anti-succinate antibody or control antibody is measured. LLC-CM or A549-CM is incubated with different concentrations of anti-succinate antibodies at 37° C. overnight, and then succinate levels in LLC-CM or A549-CM is measured by Succinate Colorimetric Assay Kit. The anti-succinate but not control antibody significantly decreases succinate level in cancer-CM (FIG. 6B). Furthermore, LLC cells seeded on the upper chamber of the transwell plates are treated with control IgG or anti-succinate antibodies (Succ Ab) for 24 h and migration assays are performed with PDGF-BB as a chemoattractant. It shows that anti-succinate antibody but not the control antibody suppresses LLC cell migration (FIG. 6C).

Accordingly, potential therapeutic monoclonal succinate antibody is further generated. Twenty mouse monoclonal antibodies are generated and selected for ELISA test. Among them, top five clones with higher binding affinity are

Figures 7A, 7B, 7C, 7D, 7E, 7F:
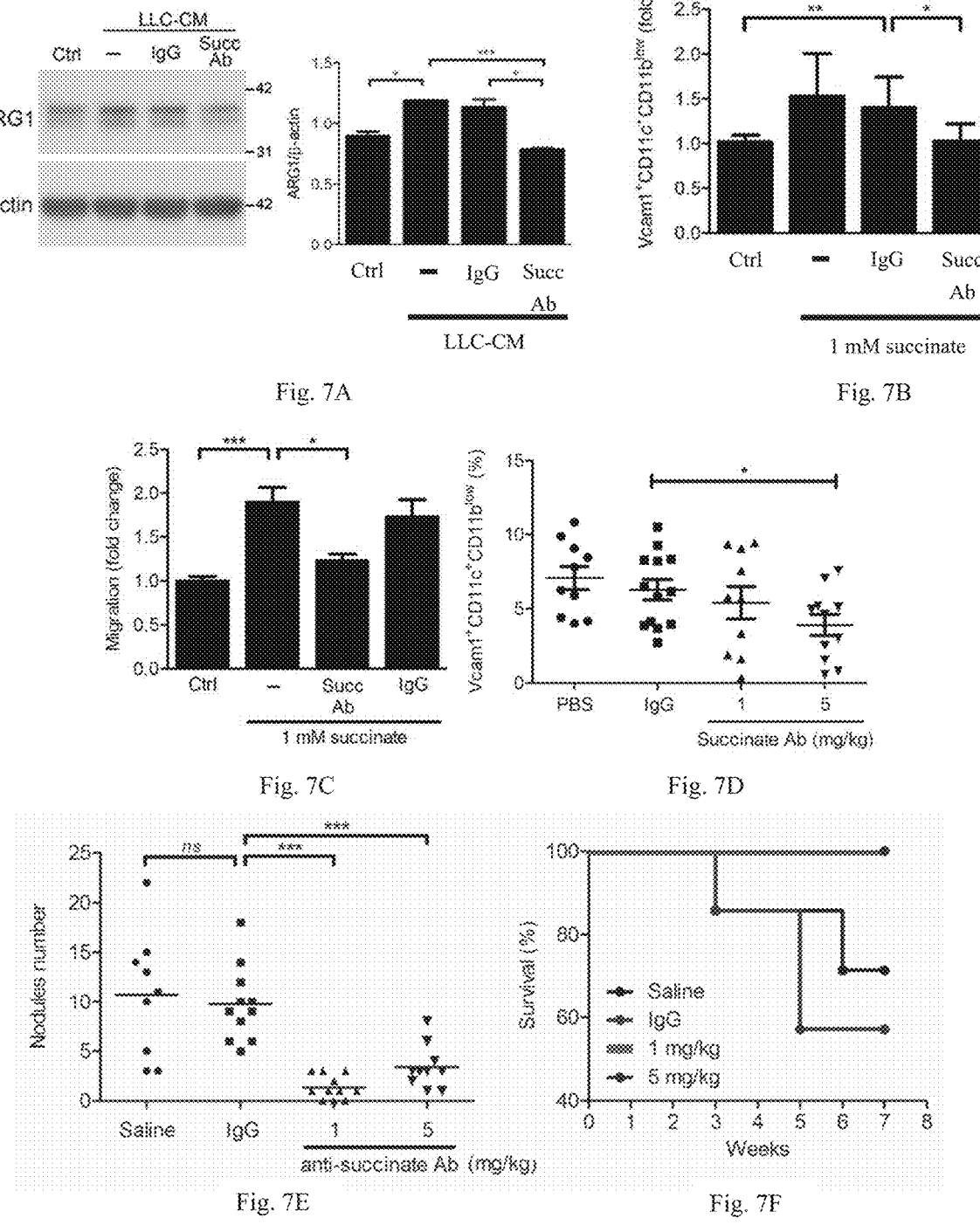
FIG. 7A-7F indicate that monoclonal antibody significantly suppresses TAM polarization and cancer metastasis and improves survival in tumor-bearing mice.

12 selected for evaluation of anti-cancer capacity. The results reveals that these five monoclonal antibodies derived by five cell lines significantly suppresses cell migration of A549 and the 6G10 cell line-derived monoclonal antibody has best anti-migratory activity. To ascertain that tumor-derived succinate is responsible for cancer-CM-induced macrophage ARG1 expression, the effect of 6G10 monoclonal antibody on ARG1 expression is evaluated. LLC-CM treated PMφs is incubated with control IgG or anti-succinate antibodies for 24 h. Cell lysates are immunoblotted with antibodies for ARG1 or β-actin. ARG1 up-regulation by LLC-CM is suppressed by F5 monoclonal antibodies but not by control IgG (FIG. 7A). In addition, PMφs are pre-treated with anti-succinate antibodies or control IgG for 1 h and then stimulated with succinate (1 mM) for 3 days. VCAM1$^+$CD11c$^+$CD11b$^{low}$-TAM population is quantified by flow cytometry and normalized to the cell number of control medium treatment. And peritoneal macrophages are treated with succinate (1 mM) with or without control IgG, anti-succinate antibodies for 24 h and cell migration are then performed by transwell assay. The data shows that F6 monoclonal antibody but not control IgG suppresses not only succinate up-regulated TAM surface markers including CD11c and VCAM1 (VCAM1$^+$CD11c$^+$CD11b$^{low}$) (FIG. 7B) but also succinate-induced macrophage migration (FIG. 7C). Thus, 6G10 monoclonal antibody is chosen as the first candidate to evaluate its therapeutic effect on syngeneic murine tumor model of LLC. The LLC cells are subcutaneously injected into C57BL/6J mice. The mice with an average 50 mm$^3$ subcutaneous tumors (8 day after LLC tumor inoculation) receive intraperitoneal injections of 6G10F6 monoclonal antibody (1 and 5 mg/kg) or IgG control antibody (5 mg/kg), twice a week for 5 weeks. The subcutaneous tumors are surgically removed 3 weeks after LLC injection for the assessment of TAM polarization; the lung, liver, spleen, and adrenal gland are excised from mice 2 weeks after removal of the primary tumor for the determination of tumor metastasis. The results show that the 6G10F6 monoclonal antibody but not IgG antibody significantly suppresses not only TAM population in subcutaneous tumors (FIG. 7D) but also lung tumor multiplicities (FIG. 7E) as compared with saline. Notably, the 6G10F6 monoclonal antibody significantly prolongs the survival of LLC tumor-bearing mice (FIG. 7F). These results suggest that 6G10F6 monoclonal antibodies may be as a therapeutic ant-cancer monoclonal antibody.

Monoclonal Antibody Sequencing of Hybridoma 6G10F6 and 6G10G5

The anti-succinate antibody sequences derived by 6G10 cell line are determined. The two hybridoma 6G10F6 and 6G10G5 are selective for antibody sequences determination. Total RNA is isolated from the hybridoma cells following the technical manual of TRIzolR Reagent. Total RNA is then reverse transcribed into cDNA using isotype-specific antisense primers or universal primers following the technical manual of PrimeScript™ 1$^{st}$ Strand cDNA Synthesis Kit. The antibody fragments of VH and VL are amplified according to the standard operating procedure (SOP) of rapid amplification of cDNA ends (RACE) of GenScript. Amplified antibody fragments are cloned into a standard cloning vector separately. Colony PCR is performed to screen for clones with inserts of correct sizes. No less than five colonies with inserts of correct sizes are sequenced for each fragment. The sequences of different clones are aligned, and the consensus sequence of these clones is shown in FIGS. 8 and 9. The DNA sequence of 6G10F6 antibody heavy chain has the sequence of SEQ ID NO: 1, and the amino acid sequence has the sequence of SEQ ID NO: 2; the DNA sequence of 6G10F6 antibody light chain has the sequence of SEQ ID NO: 3, and the amino acid sequence has the sequence of SEQ ID NO: 4. On the other hand, the DNA sequence of 6G10G5 antibody heavy chain has the sequence of SEQ ID NO: 5, and the amino acid sequence has the sequence of SEQ ID NO: 6; the DNA sequence of 6G10 G5 antibody light chain has the sequence of SEQ ID NO: 7, and the amino acid sequence has the sequence of SEQ ID NO: 8.

Antibody Humanization and Back Mutation Design for Mouse 6G10F6 Monoclonal Antibody Function of assessment of the 6G10F6 monoclonal antibody reveals that it possesses the ability of neutralizing succinate and suppressing TAM polarization and cancer metastasis. Therefore, antibody humanization is further performed to humanize the mouse 6G10F6 monoclonal antibody by using complementarity-determining regions (CDR) grafting and back mutation method without sacrificing the binding affinity of the parental (chimeric) antibody. To reduce immunogenicity, the constant regions of mouse 6G10F6 monoclonal antibody are replaced by the constant regions of human IgG4 (heavy chain) and lambda chain (light chain) for the generation of chimeric mouse-human 6G10F6 antibody used for the development of humanized antibody (FIG. 10). To proceed humanization, humanized antibody is designed by using CDR grafting and subsequent replaced putative back mutation sites of grafted antibody. Briefly, the CDRs of chimeric 6G10F6 antibody are grafted into the human acceptors (Immunoglobulin mu heavy chain VH and immunoglobulin lambda chain variable region VL; FIG. 10) to obtain humanized light chains and humanized heavy chains for each chimeric antibody. Canonical residues in CDR, framework region and residues on VH-VL interface in the grafted antibody that are believed to be important for the binding activity are selected for replacement with parental antibody counterparts.

The structure of chimeric mouse-human 6G10F6 antibody is modelled by computer-aided homology modelling program to identify the positions of back mutations. Briefly, mouse 6G10F6 antibody sequence is BLAST searched against PDB_Antibody database for identifying the best templates for Fv fragments and especially for building the domain interface. Structural template 2BJM (Crystal structure of the SPE7: Anthrone Complex) is selected, identity=66%. Amino acid sequence alignment between mouse mono and 2BJM template is shown in FIG. 11. Based on the homology model of 2BJM, all framework residues in inner core are selected. To mutate such residues back to mouse monoclonal antibody, the counterparts retain inner hydrophobic interaction and reduce potential immunogenicity resulted from back mutation. The humanized variable domains of heavy chains are named as VH1, VH2, VH3, VH4 and VH5, comprising the amino acid sequences of SEQ ID NOs: 9, 10, 11, 12, and 13, respectively; while the humanized variable domains of light chains are named as VL1, VL2, VL3, VL4, VL5, VL6, VL7 and VL8, comprising the amino acid sequences of SEQ ID Nos: 14, 15, 16, 17, 18, 19, 20, and 21, respectively. On the other hand, the humanized variable domains of heavy chains VH1, VH2, VH3, VH4 and VH5 comprises DNA sequences of SEQ ID NOs: 22, 23, 24, 25, and 26, respectively; and the humanized variable domains of light chains VL1, VL2, VL3, VL4, VL5, VL6, VL7 and VL8 comprises DNA sequences of SEQ ID NOs: 27, 28, 29, 30, 31, 32, 33, and 34, respectively.

Determination of Binding Affinity of Chimeric 6G10F6 Antibody and Humanized Antibody To construct and produce the chimeric 6G10F6 antibody and humanized antibody, the DNA sequences encoding humanized IgG heavy and light chains are synthesized and inserted into pCDNA3.4 vector to construct the expression plasmids of full-length IgGs (as shown in FIG. 11). Forty humanized antibodies are expressed in HEK293 cell culture, and then the cells are spun down. The supernatants are conducted for expression evaluation by ELISA. Binding confirmation and affinity ranking are tested by Surface Plasmon Resonance (SPR) using Biacore 8K. The chimeric 6G10F6 antibody is purified (FIG. 12A) and the affinity of succinate antibody to Ag is determined using a Surface Plasmon Resonance (SPR) biosensor. And the primary antibodies are goat anti-human IgG-HRP (GenScript, Cat. No. A00166) and goat anti-human Lambda-HRP (SouthernBiotech, Cat. No. 2070-05) respectively. The affinity and kinetics of chimeric antibody to BSA-Succinic acid is summarized in FIG. 12B, and the sensor-grams are shown in FIG. 12C. Express antibodies plus the parental antibody are performed for affinity ranking. The affinity of BSA-Succinate to 24 supernatant form HEK293 cells expressing each humanized antibody is summarized in FIG. 13. The clones without binding with the target are highlight in grey color.

Figures 14A, 14B:
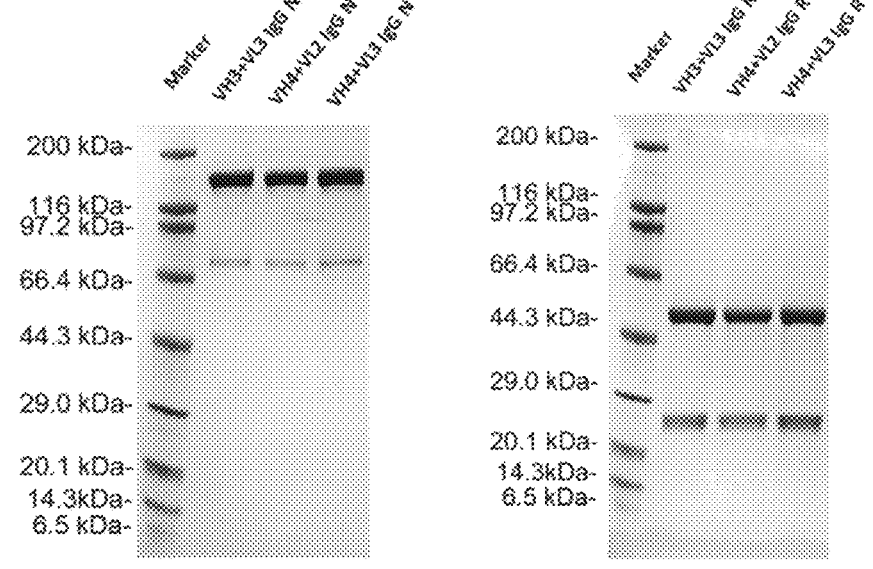
FIG. 14A-14B show the production of selected back mutation antibodies.
Figures 15A, 15B:
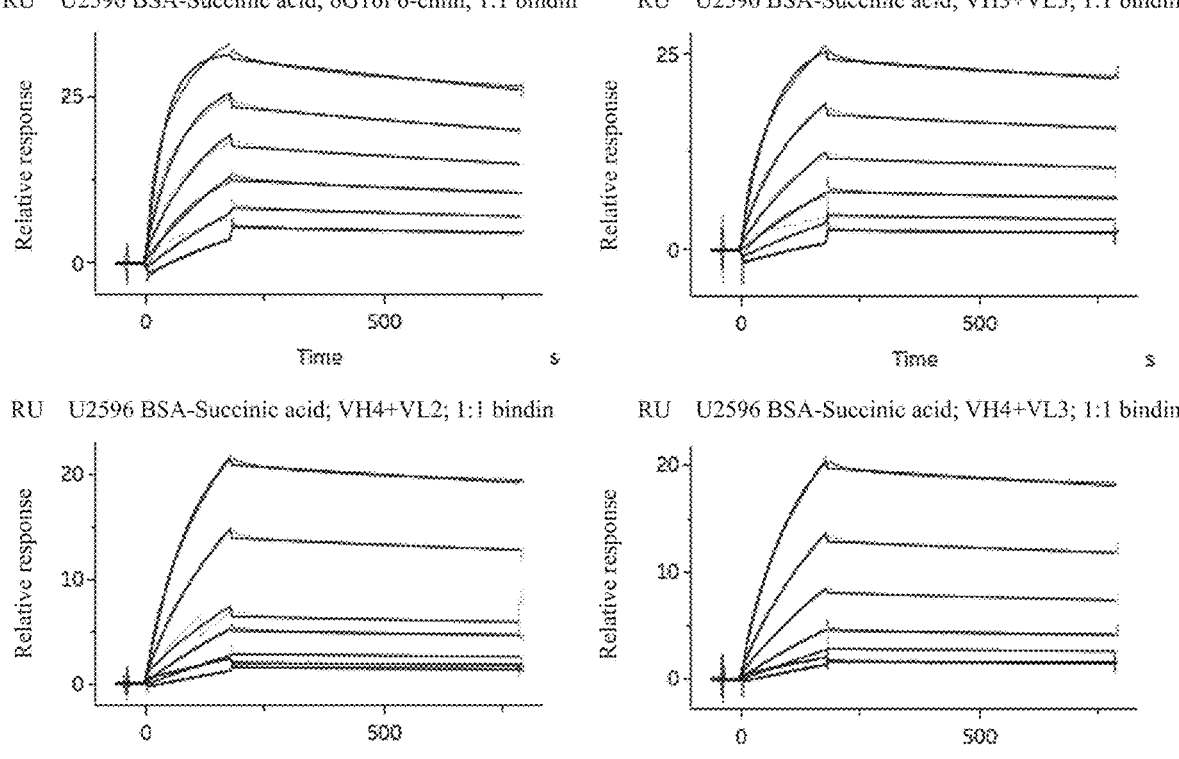
FIG. 15A-15B show the affinity measurement of chimeric and three humanized antibodies.
Figure 16A:
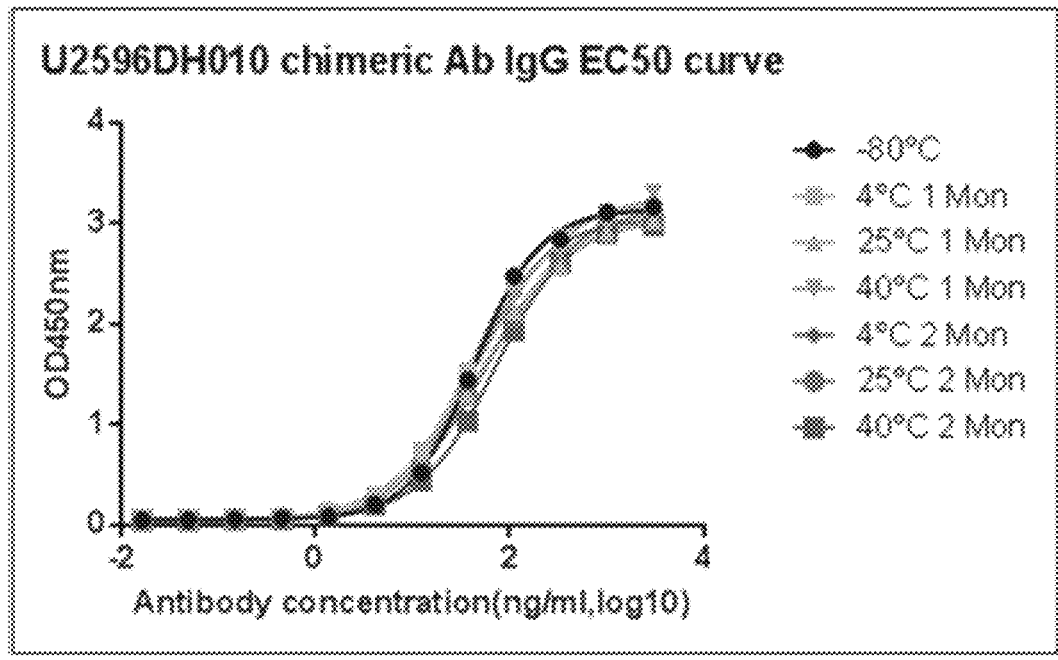
Figure 16A:
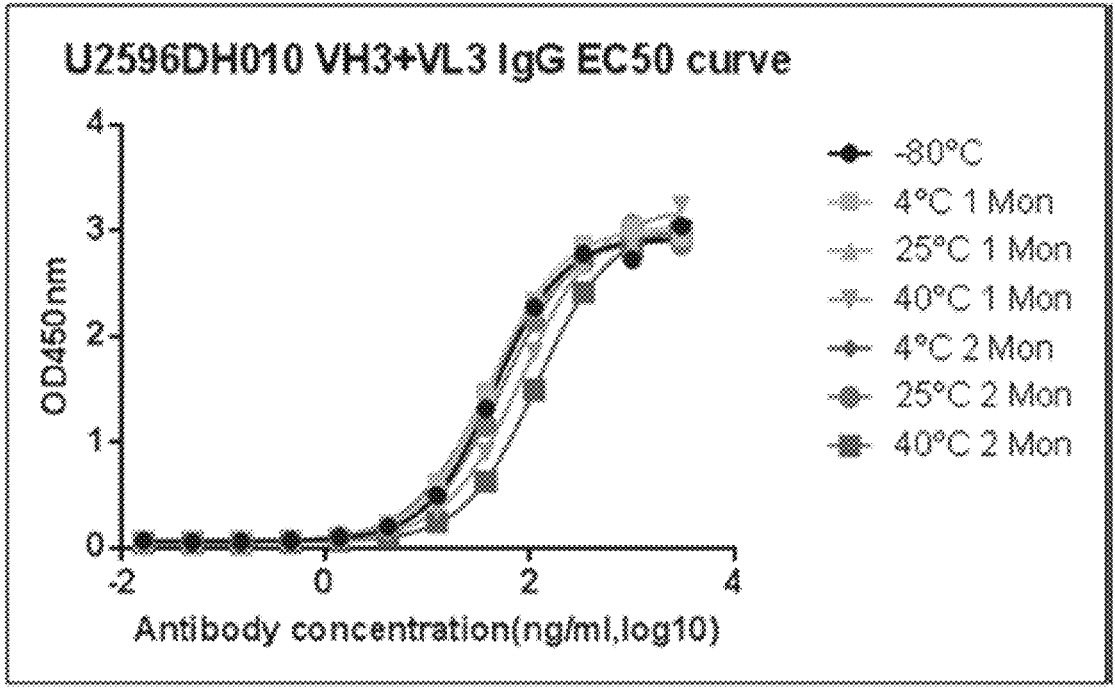
Figure 16A:
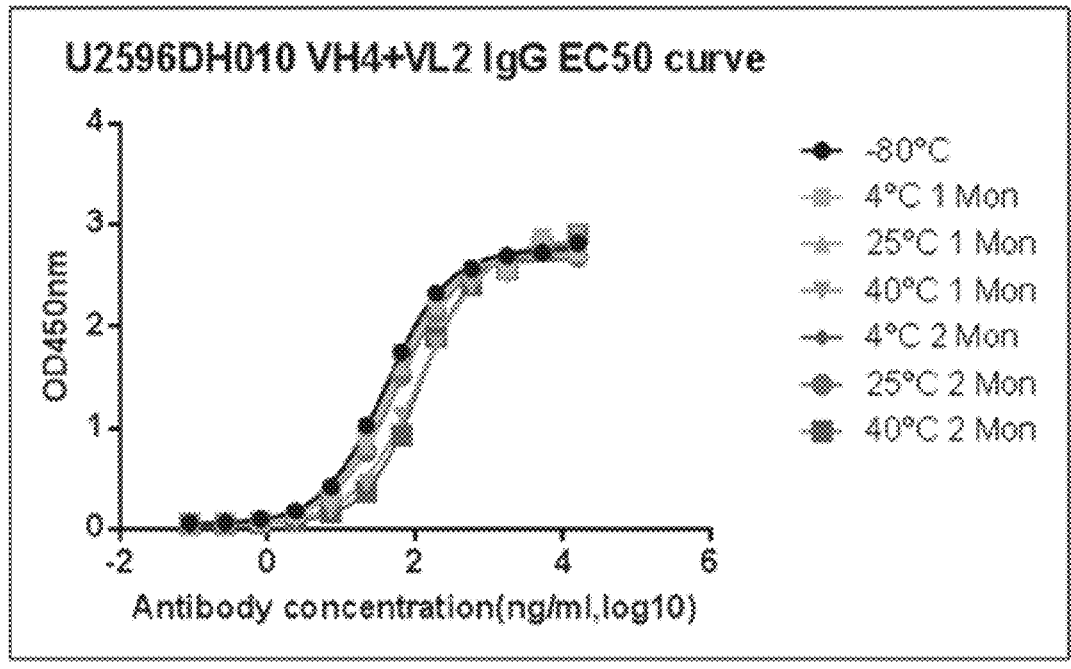
Figure 16A:
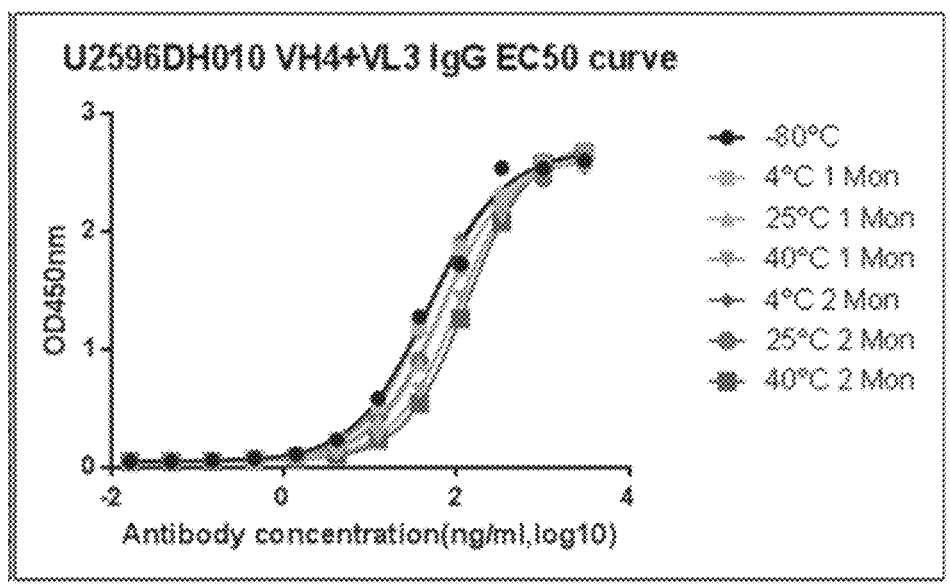

Based on the affinity ranking results, top 3 humanized antibodies (VH3+VL3, VH4+VL2, VH4+VL3) are expressed and purified according to GenScript's SOP. Evaluating from the SDS-PAGE, the purity of humanized IgGs are about 85% (FIG. 14A). The yields of purified IgGs are listed in FIG. 14B. The top 3 purified antibodies are further selected for affinity measurement under different concentrations. Binding data of each antibody is processed and fitted to 1:1 interaction model using Biacore 8K evaluation software. All experimental data could be well fitted to the model (FIG. 15A). As listed in FIG. 15B, three humanized antibodies retain comparable antigen-binding affinities to the parent chimeric antibody.

Thermo-Stability Measurement of Purified Humanized IgGs

In addition, four purified antibodies (including chimeric antibody, VH3+VL3, VH4+VL2, VH4+VL3 humanilized antibodies) and nine supernatants form HEK293 cells expressing each humanized were selected for stability evaluation by ELISA. The ELISA results show that three humanized antibodies bound to antigen strongly after different temperature treatments for 2 months (FIG. 16).

Collectively, mouse monoclonal antibody (mAb) is successfully humanized. Five heavy chains and eight humanized light chains are designed, synthesized and inserted into pCDNA3.4 expression vector.

Example 4. Succinate Induces Cancer Cell Migration and Enhances Cancer Metastasis Via a Specific Membrane Receptor, SUCNR1

SUCNR1 Signaling Participates in Succinate-Mediated TAM Polarization

Figure 17D:
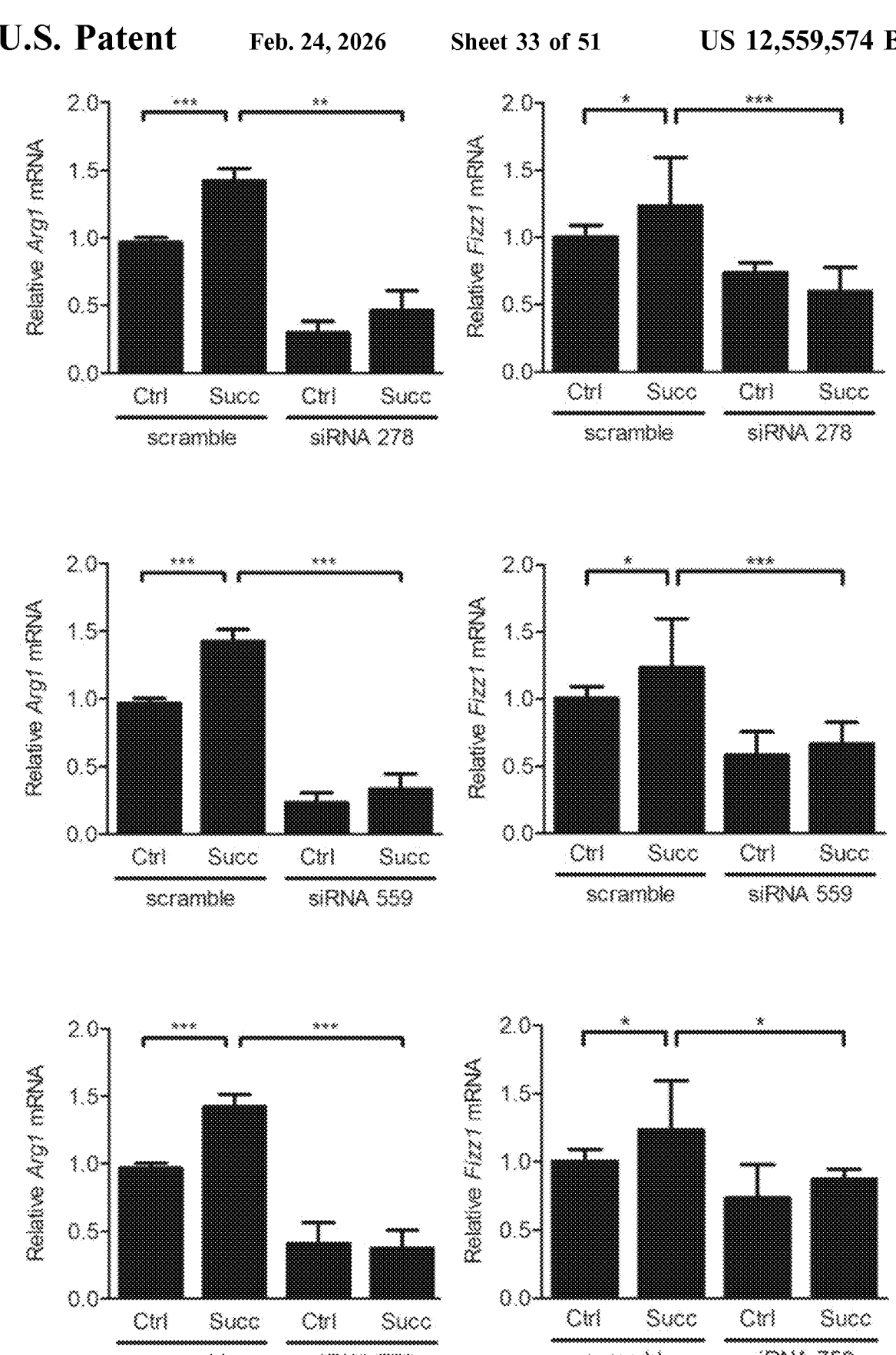
Figure 17D:
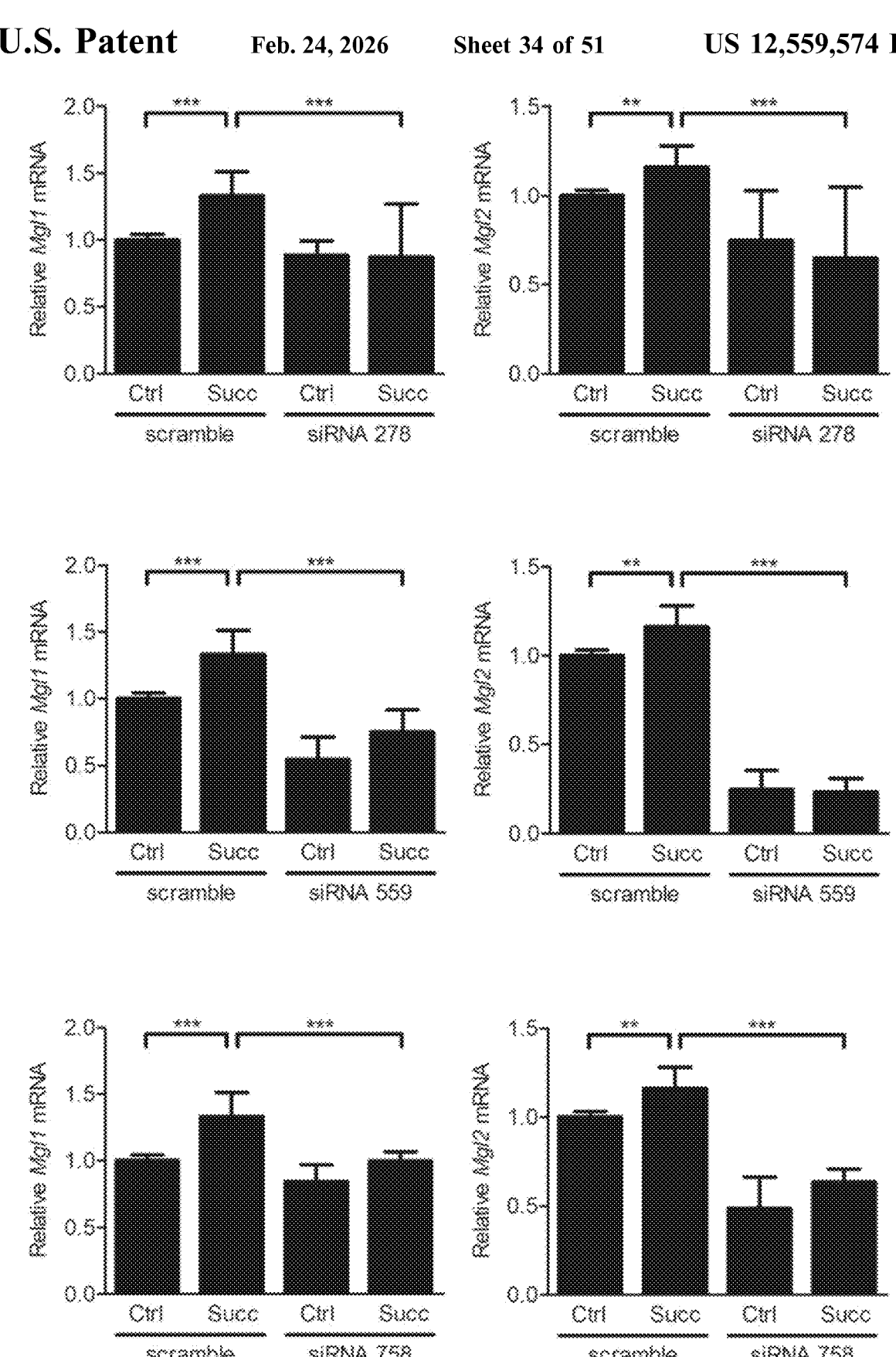
Figure 17E:
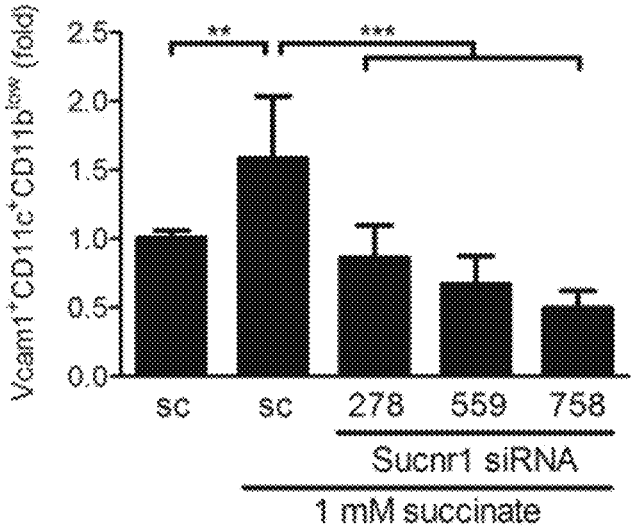

Succinate is known as a SUCNR1 ligand. Therefore, it is investigated that if succinate promotes TAM polarization through SUCNR1. First, after pretreating peritoneal macrophages with control IgG and anti-SUCNR1 antibodies for 1 h, cells are stimulated with succinate (1 mM) for 3 days. VCAM1$^+$CD11c$^+$CD11b$^{low}$-TAMs are quantified by flow cytometry and expressed as fold of control medium treatment. Treatment of macrophages with anti-SUCNR1 antibodies but not with control IgG abolishes succinate-mediated up-regulation of VCAM1$^+$CD11c$^+$CD11b$^{low}$-TAMs (FIG. 17A). In addition, peritoneal macrophages are transfected with scrambled control siRNA, mouse SUCNR1 siRNA-278, -559, or -758 for 48 h, and cells are stimulated without or with 1 mM succinate (Succ) for 16 h or 3 days. Sucnr1 mRNA expression and SUCNR1 protein level in macrophages are measured by qPCR and western blot with antibody for ARG1 or β-actin, respectively (data represent the mean±SEM of 3 experiments. *P<0.05; P<0.005; *P<0.0005). The results show that suppression of SUCNR1 levels (FIGS. 17B and 17C) with specific siRNAs (si-278, si-559 and si-758) but not a control siRNA inhibits succinate-induced expression of Arg1, Fizz1, Mgl1, and Mgl2 mRNAs (FIG. 17D). Succinate-mediated up-regulation of VCAM1$^+$CD11c$^+$CD11b$^{low}$-TAMs is abrogated by three different SUCNR1 siRNAs but not by scrambled siRNA (FIG. 17E). These results suggest that succinate promotes TAM polarization through the SUCNR1 signaling pathway.

Succinate-Activated SUCNR1 Promotes Macrophage Migration

Figure 18A:
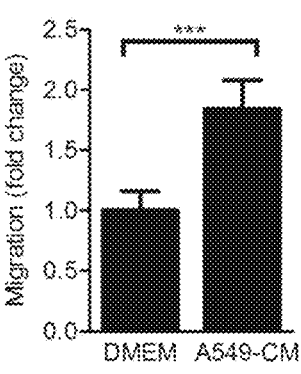
FIG. 18A-18E exhibit that tumor-derived succinate activates SUCNR1 to promote peritoneal macrophage migration.
Figure 18B:
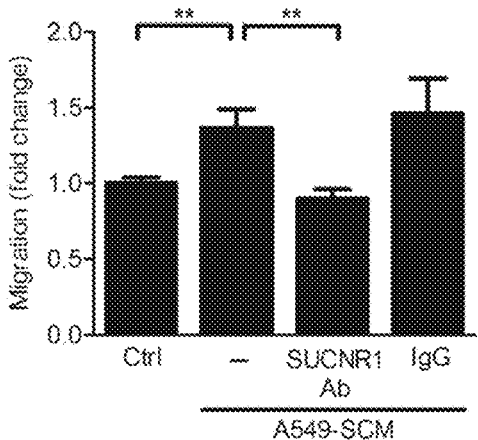
Figure 18C:
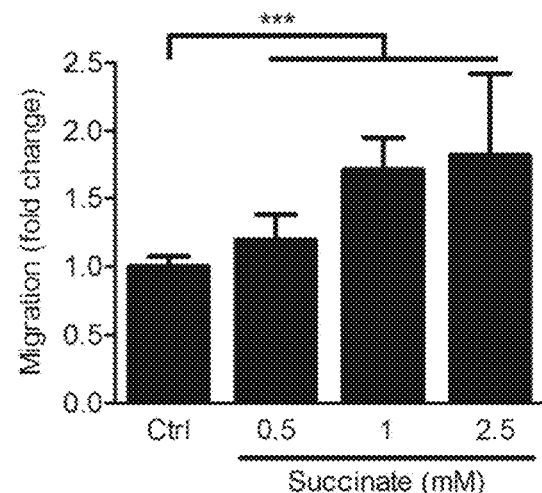

It is further examined that if cancer-CM and succinate induce macrophage migration. The peritoneal macrophages are seeded on the upper chamber of transwell plates and cultured with control medium (DMEM) or CM from A549 (A549-CM) for 24 h. On the other hand, the peritoneal macrophages are seeded on the upper chamber of the transwell plates and cultured with control medium (DMEM) or A549-SCM in the presence or absence of control IgG or anti-SUCNR1 antibodies for 24 h. Migration assays are then performed with PDGF-BB as a chemoattractant and migrated cell counts expressed as fold of basal controls. As shown in FIGS. 18A and 18B, A549-CM and A549-SCM increase macrophage migration compared with the control medium, which is abrogated by anti-SUCNR1 antibody but not control IgG. Furthermore, the peritonea macrophages are treated with different concentrations of succinate for 24 h. It shows that the anti-SUCNR1 antibody but not control IgG abrogates the succinate-induced macrophage migration (FIG. 18C). It indicates that succinate/SUCNR1 signaling is essential for macrophage migration.

Figure 18D:
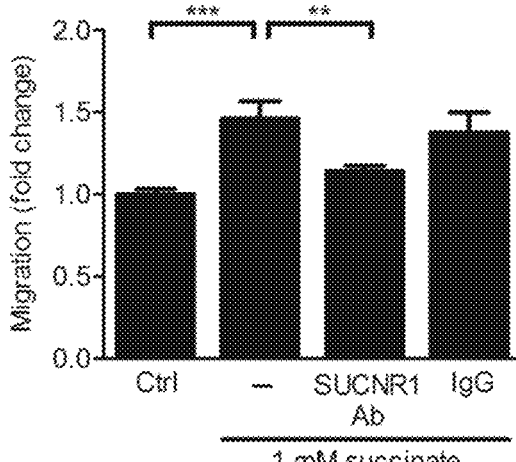
Figure 18E:
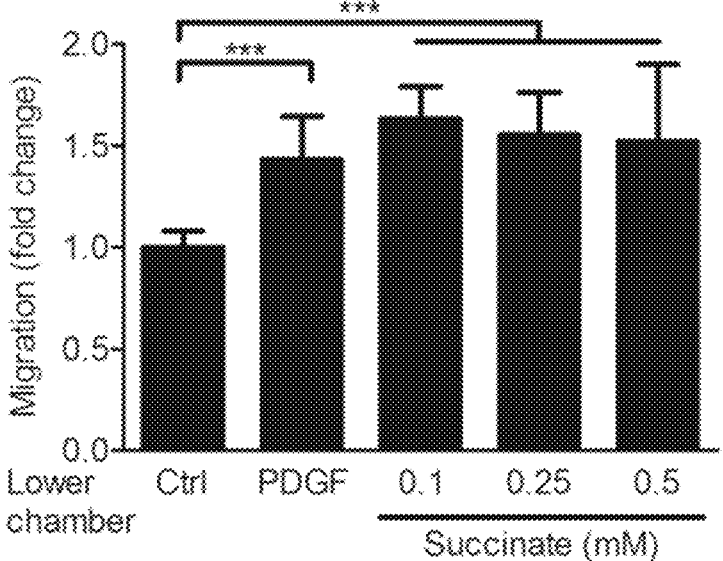

To determine whether tumor-derived succinate acts as a soluble chemotactic factor for macrophages, the peritoneal macrophages are treated with succinate (1 mM) with or without control IgG or anti-SUCNR1 antibodies for 24 h and cell migration are then analyzed by transwell assay. And PDGF and different concentrations of succinate were placed in the bottom chambers of the transwell plates for macrophage migration assays. Compared with the control, succinate dramatically increase macrophage migration (FIG. 18D). The extent of migration induced by succinate is close to that induced by PDGF. The results suggest that tumor cells secrete succinate to promote macrophage recruitment and migration and consequent TAM polarization.

Figures 19A, 19B:
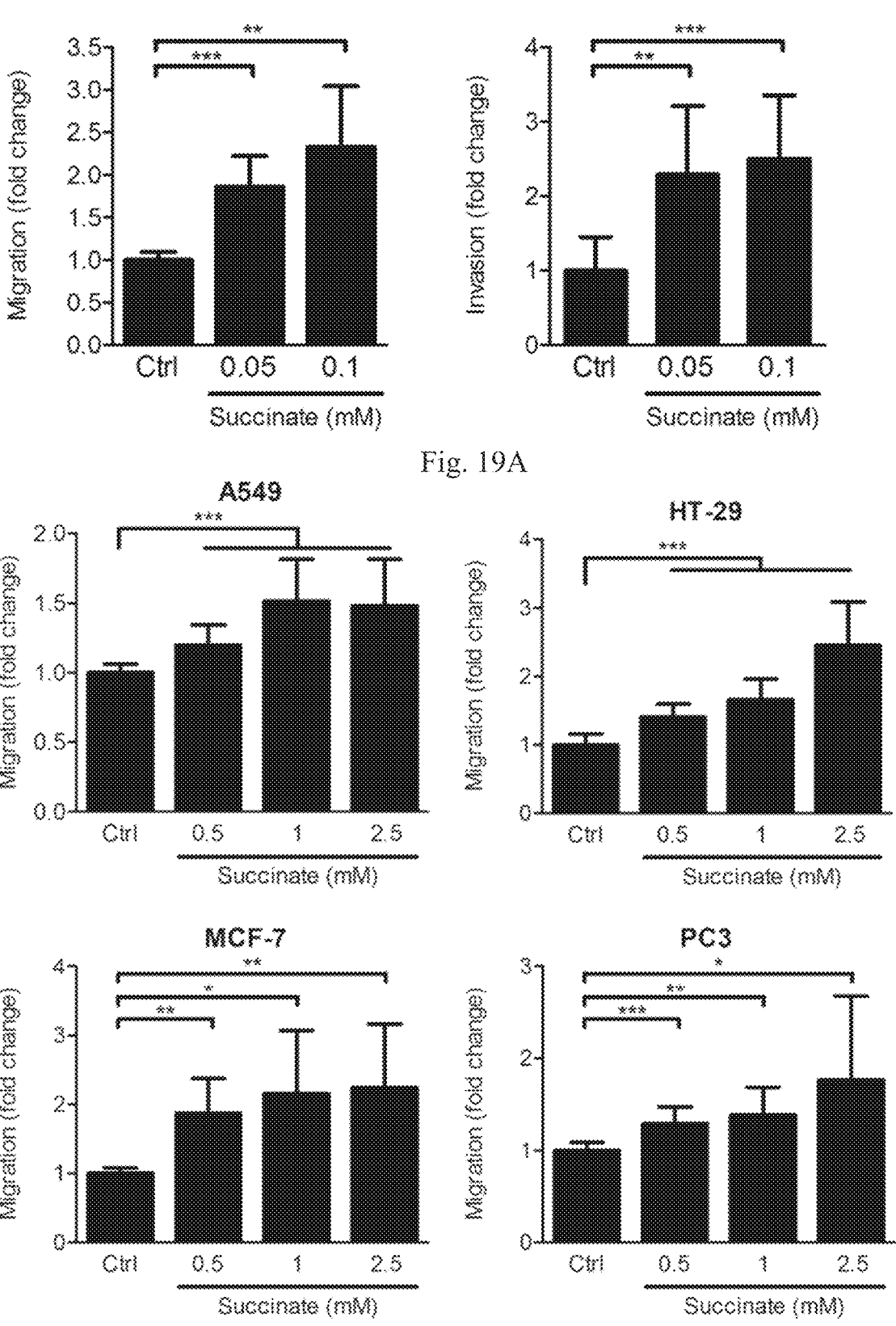
FIG. 19A-19F show that succinate promotes tumor cell migration and invasion.
Figure 19C:
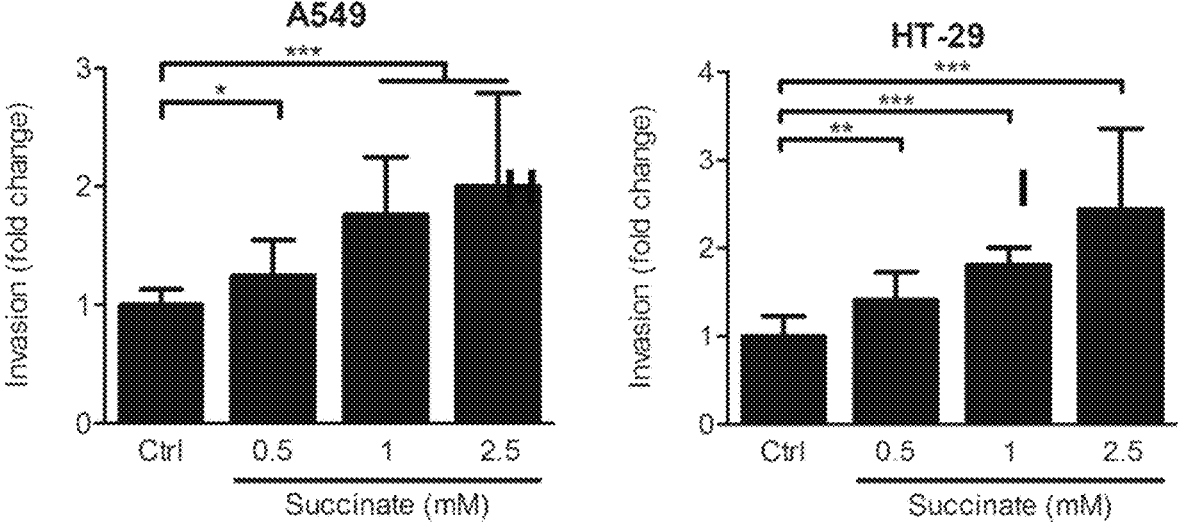

Succinate Induces Cancer Cell Migration and Epithelial-Mesenchymal Transition (EMT) and Enhances Cancer Metastasis As succinate promotes macrophage migration, it is wondered that if succinate regulates cancer cell migration. LLC cells are seeded on regular or Matrigel-coated membrane and treated with different concentrations of succinate for 24 h. Transwell migration and invasion assays are performed. Relative ability of migration or invasion is calculated from 3 fields under a light microscope. Also, cells including A549, HT-29, MCF-7, and PC3 cells are seeded on the upper chamber of the transwell plates and treated with different concentrations of succinate for 24 h. Migration assays and Matrigel invasion assay are then performed with PDGF-BB as a chemoattractant and migrated cell counts expressed as fold of basal controls. The results reveal that succinate promotes cell migration and invasion of LLC lung cancer cells (FIG. 19A) and A549, colon (HT-29), breast (MCF-7), and prostate cancer cells (PC3), in a dose-dependent manner (FIGS. 19B and 19C).

Figure 19D:
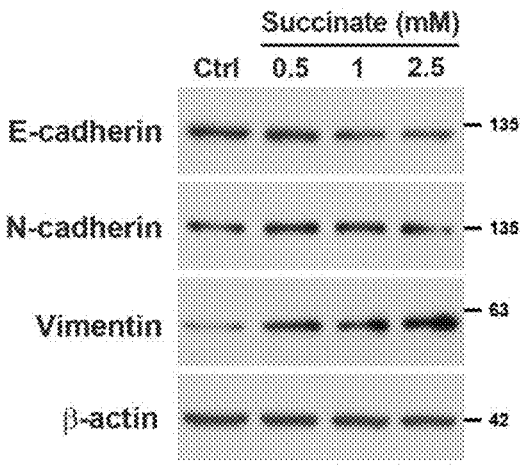
Figure 19E:
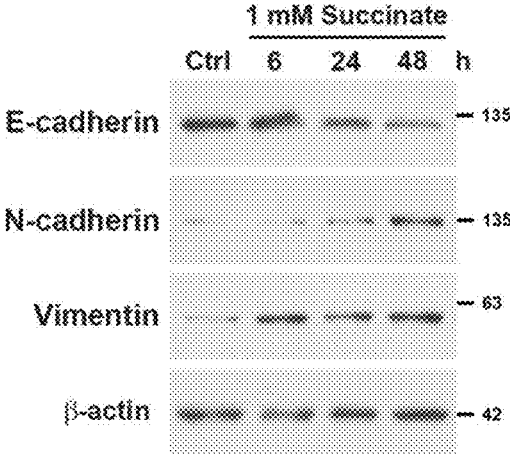
Figure 19F:
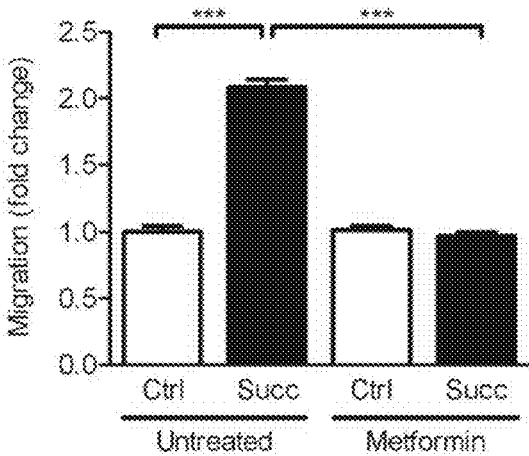

And succinate also influences cancer cell EMT. In summary, A549 cells are treated with vehicle or succinate (0.5, 1 and 2.5 mM) for 24 h. And A549 cells are also treated with vehicle or succinate (1 mM) for the indicated time periods. The cells are lysed, and the cell lysates are immunoblotted with antibodies specific for E-cadherin, N-cadherin, vimentin, or β-actin. On the other hand, A549 cells are treated with succinate with or without metformin (2 mM) for 24 h to evaluate the EMT inhibition, and cell migration is determined using transwell assay. Succinate suppresses E-cadherin and increased N-cadherin and vimentin in a concentration and time-dependent manner (FIGS. 19D and 19E). Importantly, metformin, an EMT inhibitor, abolish succinate-induced A549 migration (FIG. 19F). These results suggest that cancer cell-secreted succinate acts in an autocrine and paracrine manner to promote cancer cell migration and invasion through an EMT-dependent mechanism.

Figure 20A:
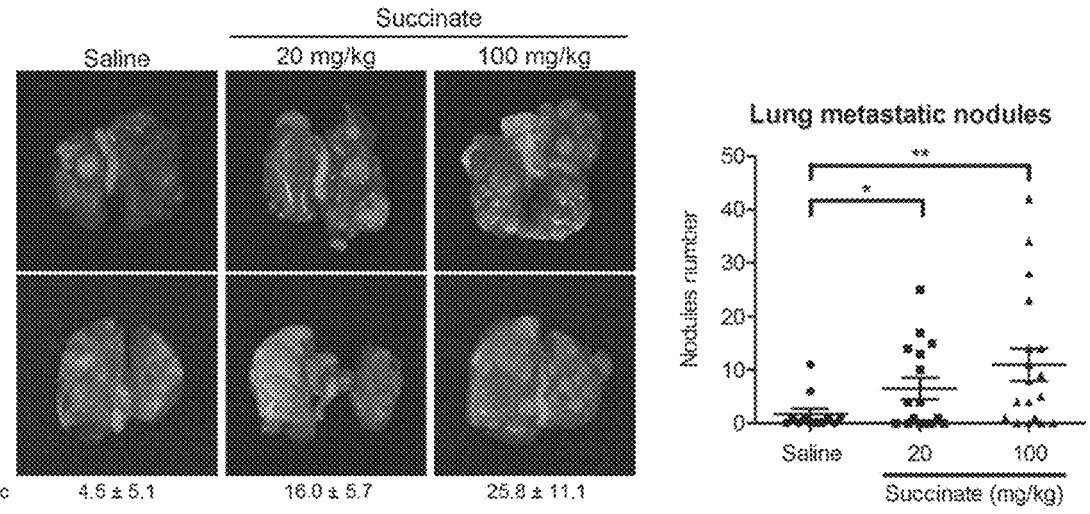
FIG. 20A-20C show that succinate promotes cancer metastasis.
Figure 20B:
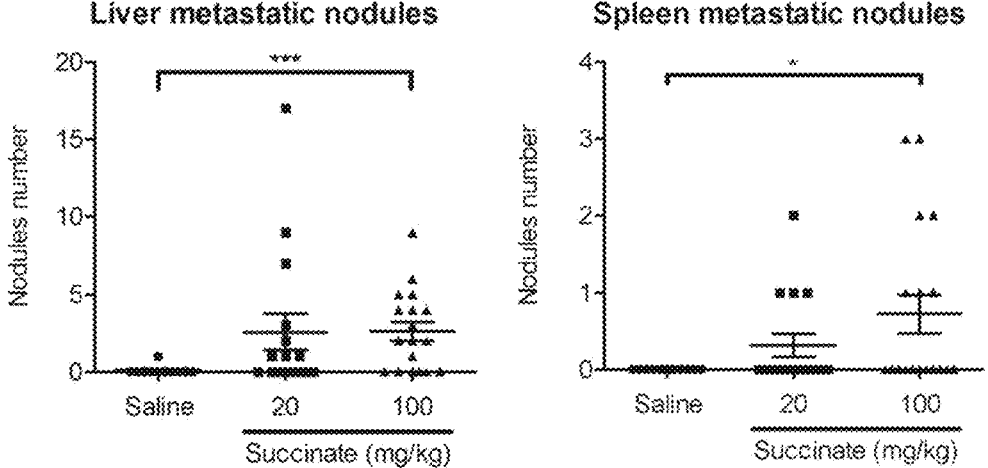
Figure 20C:
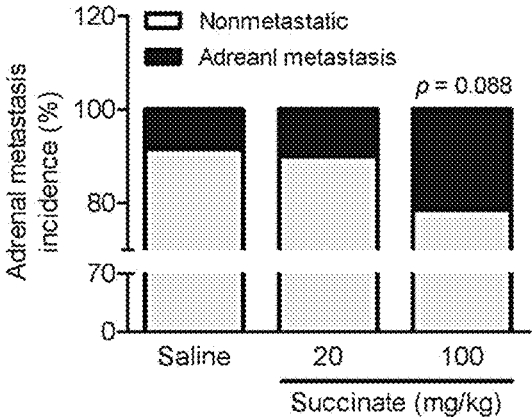

Physiological relevance of tumor-derived succinate in tumor metastasis is determined in a syngeneic murine LLC tumor model. LLC cells are subcutaneously injected into C57BL/6J mice followed by intraperitoneal injections of vehicle or succinate (20 and 100 mg/kg) twice a week. The subcutaneous primary tumors are surgically removed after 3 weeks and mice are kept for another 2 weeks at which time animals are sacrificed. Lung, liver, spleen, and adrenal gland are excised for determination of metastasis. Metastatic cancer nodules in lungs are higher in mice receiving succinate (in a dose-dependent manner) than in mice receiving saline (FIG. 20A). Metastatic cancer nodules in liver and spleen are similarly higher in succinate-treated animals (FIG. 20B). Incidence of adrenal metastasis is higher in succinate-treated animal, but the difference does not reach statistical significance (p=0.088) (FIG. 20C).

Succinate-Induced Polarized Macrophages Enhance Cancer Cell Migration

Figures 21A, 21B, 21C, 21D, 21E:
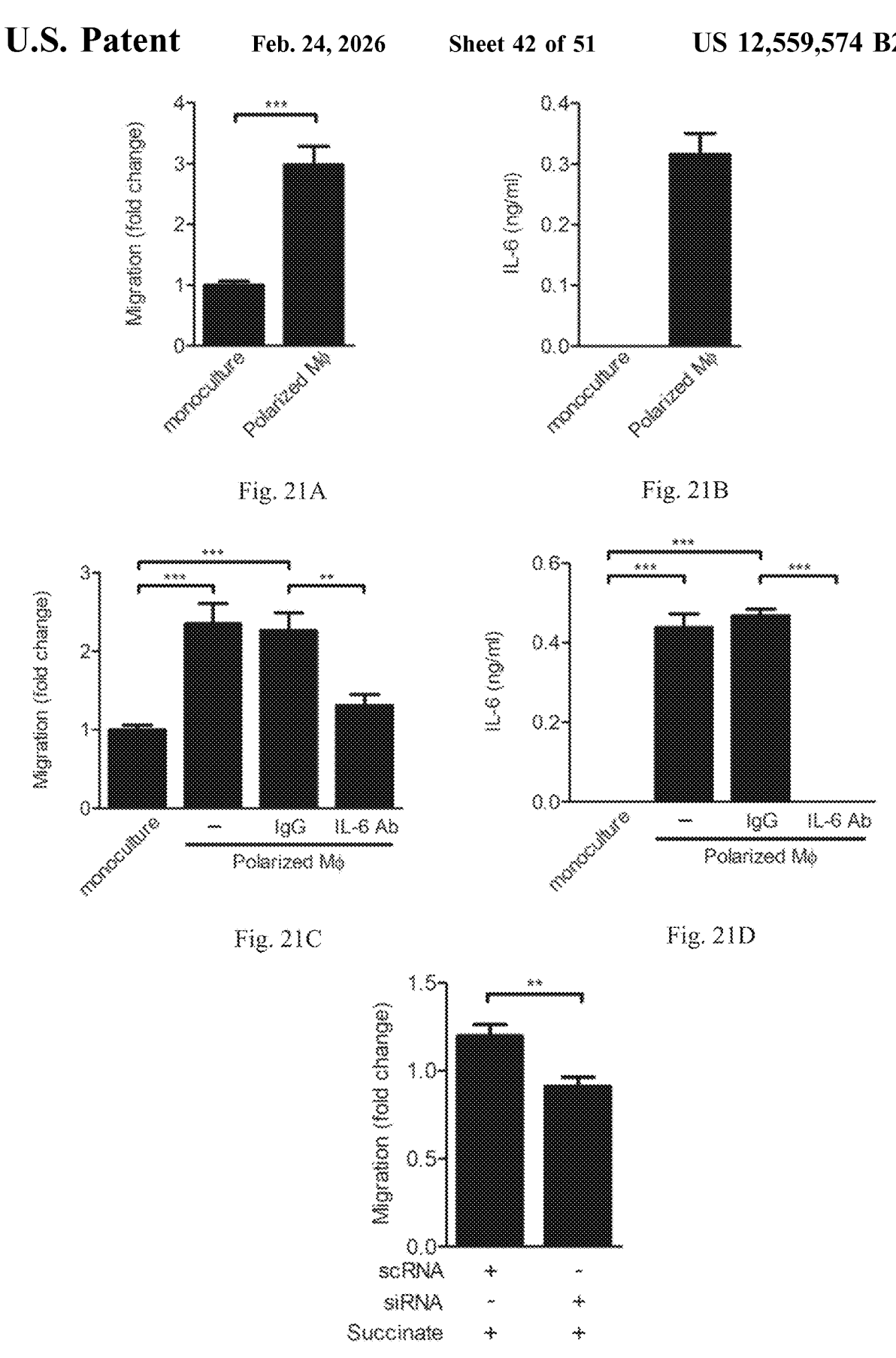
FIG. 21A-21E indicate that succinate-induced polarized macrophages enhance cancer cell migration.

As succinate indirectly increasing cancer cell migration via macrophage phenotypic change, it is evaluated that the effect of succinate-induced polarized macrophages on cancer cell migration. Polarized macrophages induced by treating macrophages with succinate for 3 days are co-cultured with LLC cancer cells in transwell culture dishes, and cancer cell migration is analyzed by transwell assay. The results show that polarized macrophages enhance LLC cell migration when it is compared with LLC cell monoculture (FIG. 21A). On the other hand, IL-6 concentration is increased in co-culture medium but not in monoculture medium (FIG. 21B). Notably, enhanced migratory ability of LLC cells co-cultured with polarized macrophages is abrogated by addition of anti-IL-6 neutralizing antibody (FIG. 21C) for eliminating IL6 in co-culture medium (FIG. 21D). These results indicate that polarized macrophages-mediated IL-6 secretion is pivotal in LLC migration.

Macrophages transiently transfected with SUCNR1 siRNA758 are treated with succinate for 3 days which are co-cultured with LLC cells. Compared with macrophages transfected with a control siRNA, cell migration of macrophages transfected with SUCNR1 siRNA758 is significantly reduced (FIG. 21E). The results suggest that succinate-induced macrophage polarization contributes to promotion of cancer cell migration.

Succinate Promotes Cancer Metastasis Via SUCNR1 Signaling

Figure 22A:
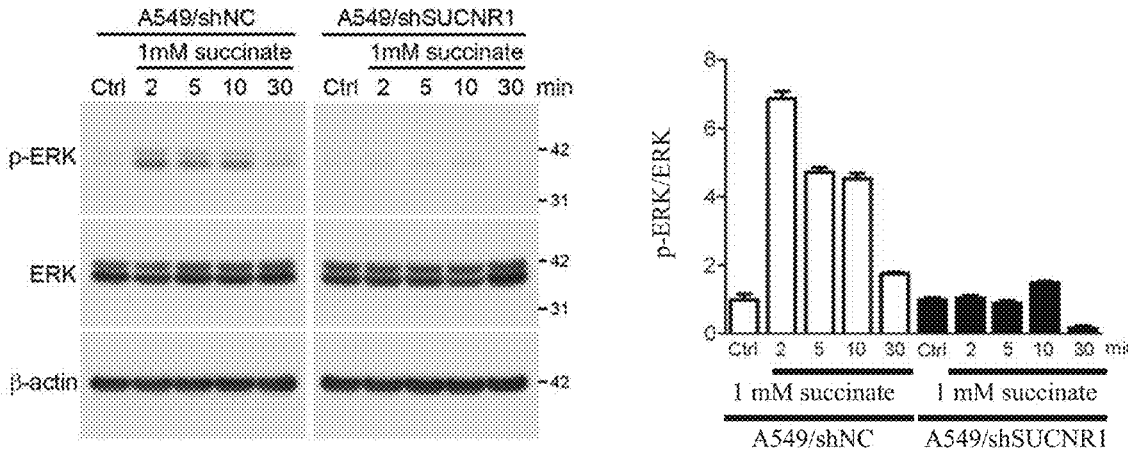
FIG. 22A-22C exhibit that effect of succinate on intracellular calcium mobilization, ERK1/2 activation and prostaglandin E2 production.
Figure 22B:
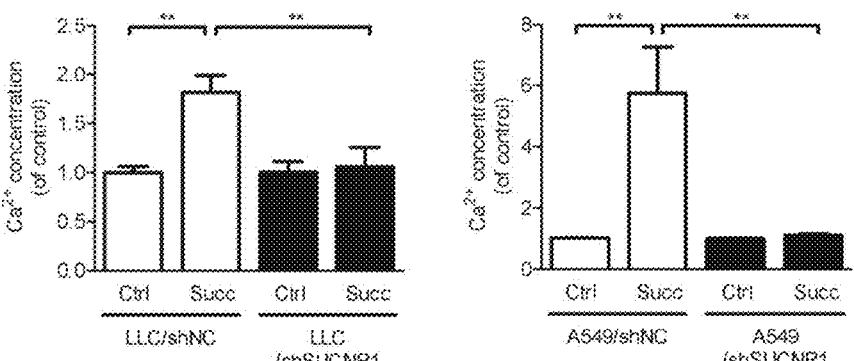
Figure 22C:
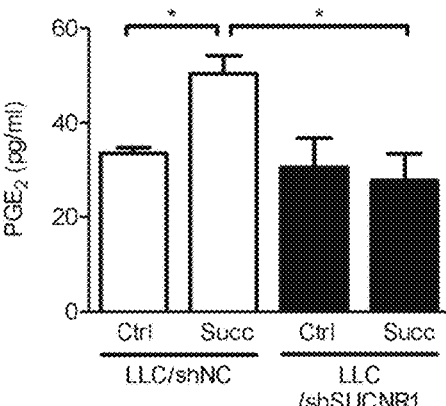

Succinate binding to SUCNR1 activates several signaling targets notably mitogen-activated protein kinases (MAPK) as well as increases intracellular calcium and prostaglandin E2 (PGE$_2$). To ascertain that succinate activates cancer cell SUCNR1, the canonic targets in A549 cells stimulated by succinate are analyzed. A549/shNC, and A549/shSUCNR1 cells are treated with succinate (1 mM) for the indicated time periods, and then cell lysates are immunoblotted with antibodies specific for ERK1/2, phospho-ERK1/2. Following succinate treatment, there is a rapid rise of phosphorylated ERK1/2 at 2 min which is abrogated in A549 stably transfected with SUCNR1 shRNA but not A549 stably transfected with control RNA (FIG. 22A). LLC/shNC, LLC/shSUCNR1, A549/shNC, and A549/shSUCNR1 cells are further treated with succinate (1 mM) for 2 h, and then intracellular calcium level and conditioned medium PGE2 level are measured by Calcium Colorimetric Assay Kit and PGE2 ELISA kit, respectively. Intracellular Ca$^{2+}$ is increased after A549 or LLC cells are treated with succinate for 2 h (FIG. 22B). However, Ca$^{2+}$ level is not elevated in either cell type stably transfected with SUCNR1 shRNA (FIG. 22B). PGE$_2$ released into the medium is increased in LLC cells stably transfected with control shRNA but not in LLC cells stably transfected with SUCNR1 shRNA (FIG. 22C). These results are consistent with the interpretation that succinate activates SUCNR1 signaling targets.

Figure 23A:
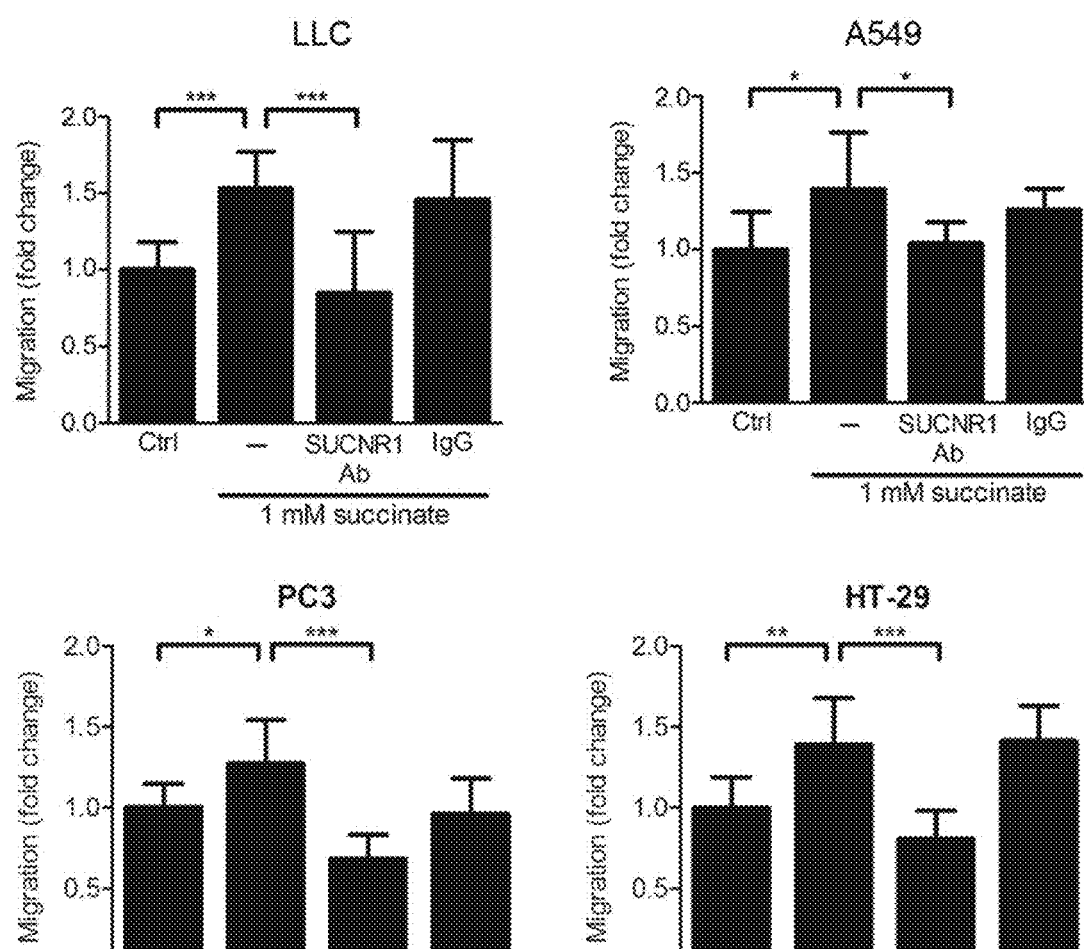
FIG. 23A-23B show that succinate promotes tumor cell migration and invasion through SUCNR1 signaling.
Figure 23B:
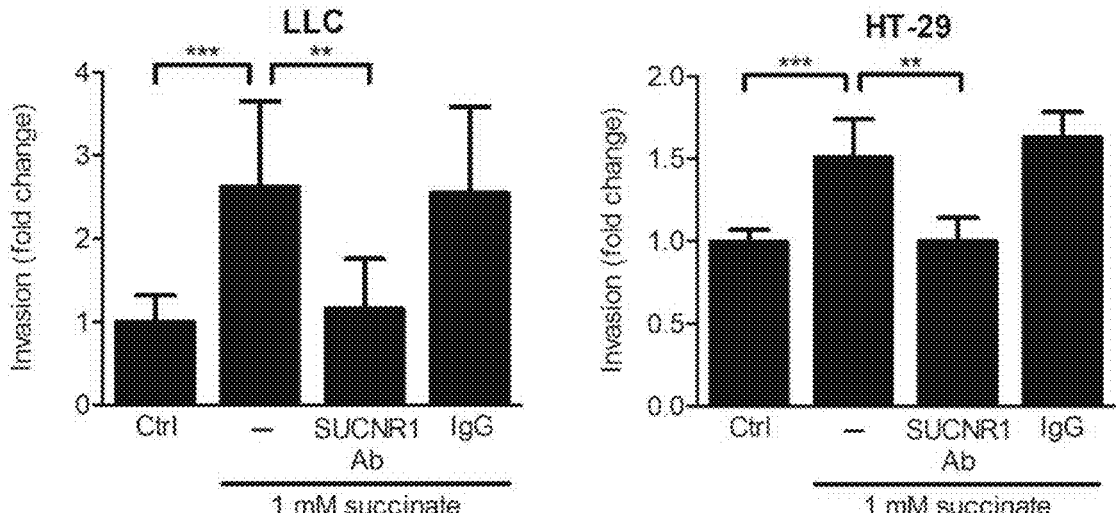

The ability of succinate for inducing cancer cell migration via SUCNR1 is further evaluated. LLC, A549, PC3, and HT-29 cells are treated with succinate (1 mM) with or without control IgG or anti-SUCNR1 antibodies for 24 h and migration is determined by transwell assay. Succinate-induced migration of LLC, A549, PC3 and HT-29 cells is blocked by anti-SUCNR1 antibody but not control IgG antibody (FIG. 23A). Furthermore, invasion of LLC and HT-29 cells treated with succinate (1 mM) with or without control IgG or anti-SUCNR1 antibodies for 24 h is determined using Matrigel invasion assay. The results show that succinate-induced invasion of LLC and HT-29 is similarly inhibited by SUCNR1 antibody and not by IgG antibody (FIG. 23B).

Figure 24A:
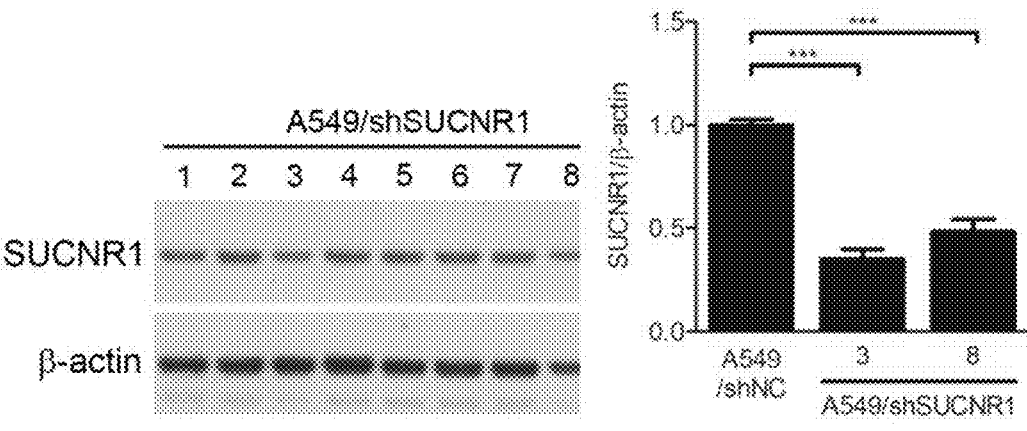
FIG. 24A-24F indicate that tumor-secreted succinate promotes tumor metastasis through SUCNR1 signaling.
Figure 24B:
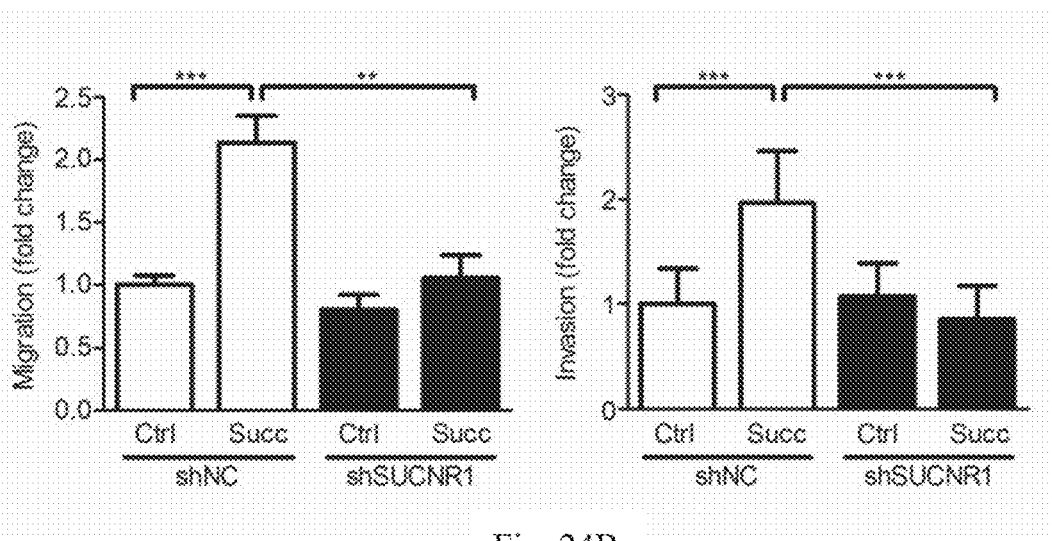
Figure 24C:
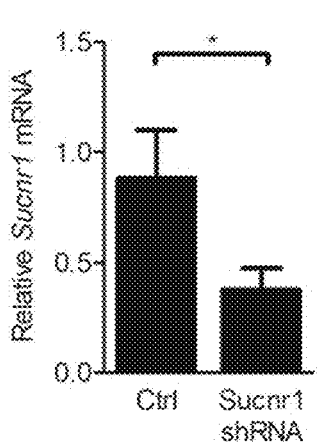
Figure 24D:
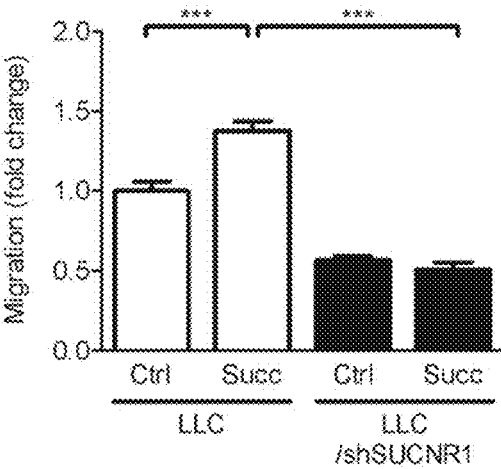

It is next analyzed that succinate-induced cell migration and invasion in A549 stably transfected with SUCNR1 shRNA which exhibited reduced SUCNR1 expression (stable #3 and #8, FIG. 24A). A549 cells stably transfected with control shRNA (A549/shNC) or SUCNR1 shRNA (A549/shSUCNR1) are stimulated with succinate (1 mM) for 24 h. Cell migration and invasion are measured by transwell assay and Matrigel invasion assay. The results show that succinate-induced A549 migration and invasion are suppressed by SUCNR1 knockdown (FIG. 24B). In addition, LLC stably transfected with shSUCNR1 (LLC/shSUCNR1) which expresses decreased Sucnr1 have reduced succinate-induced cell migration compared to control (FIGS. 24C and 24D).

Figures 24E, 24F:
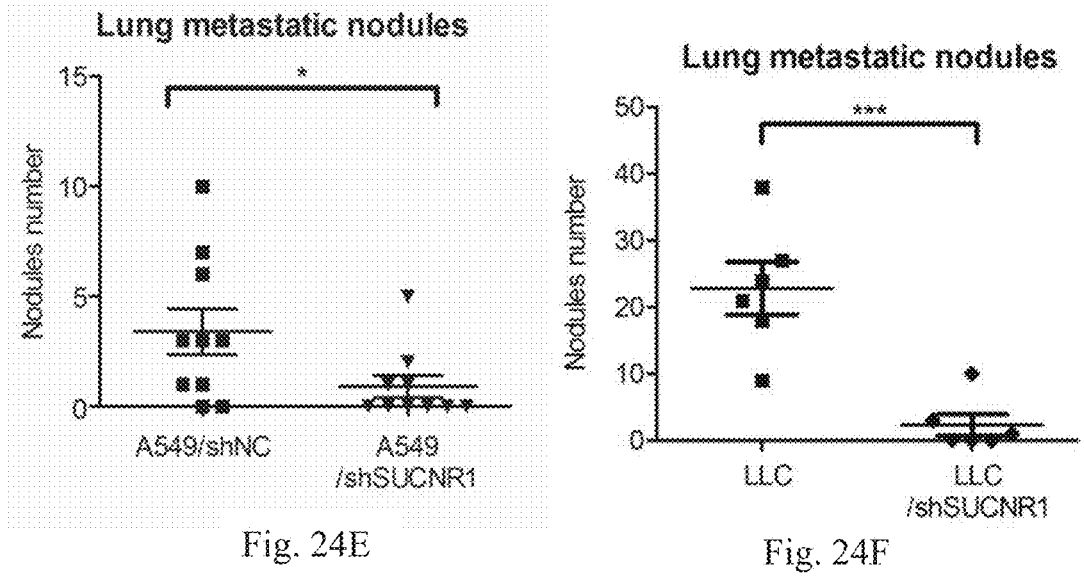

To investigate the role of SUCNR1 in succinate-enhanced metastasis in vivo, A549/shNC or A549/shSUCNR1 cells are implanted subcutaneously into nude mice. Mice subsequently receive an intraperitoneal injection of succinate (100 mg/kg) twice weekly for 8 weeks. Mice are euthanized on day 56, and lung tissues are excised for metastatic nodules examination. Lung metastatic nodules are significantly lower in mice inoculated with A549/shSUCNR1 than in animals inoculated with A549/shNC (FIG. 24E). Similarly, metastatic nodules in lungs are significantly reduced in mice inoculated with LLC/shSUCNR1 (FIG. 24F). These results suggest that succinate promotes cancer metastasis via SUCNR1.

Succinate Induces Cancer Metastasis Through PI3K/AKT and HIF-1α Signaling

Figure 25A:
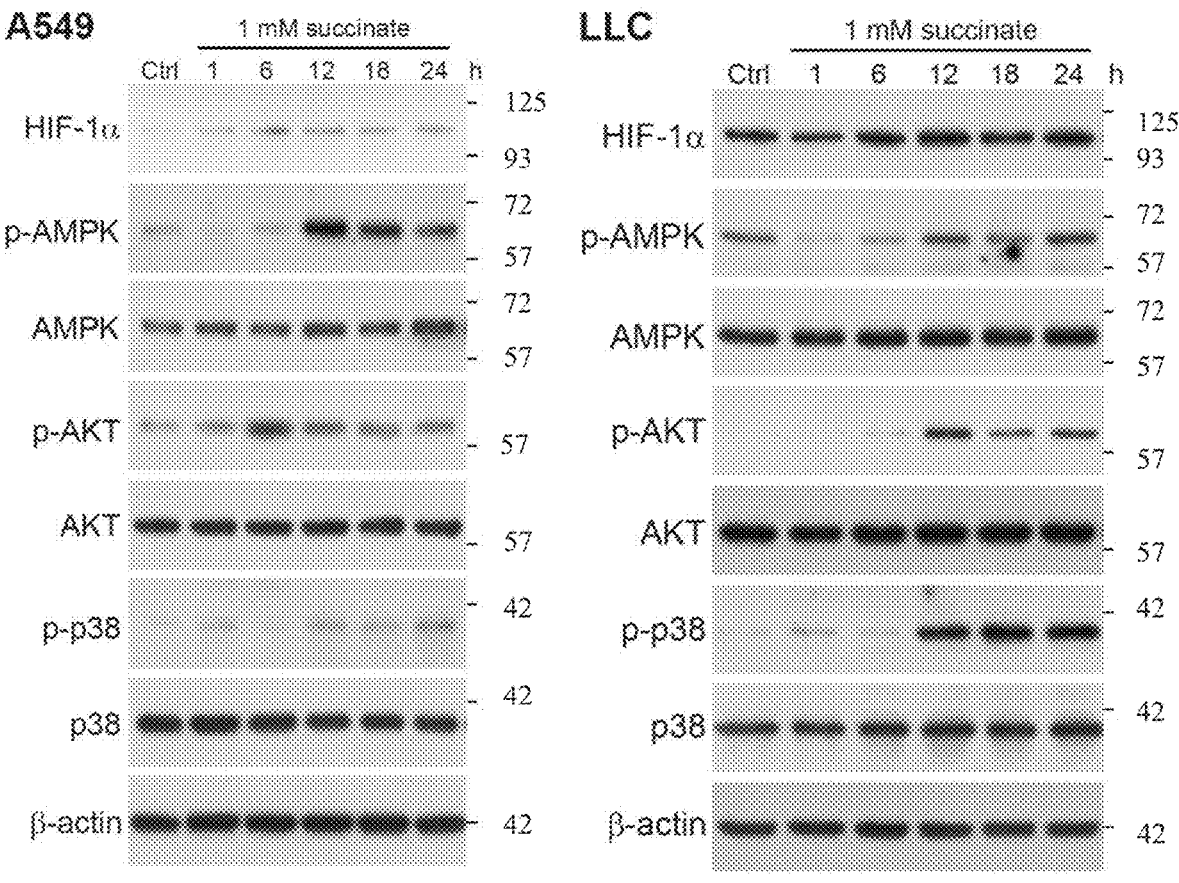
Figure 25B:
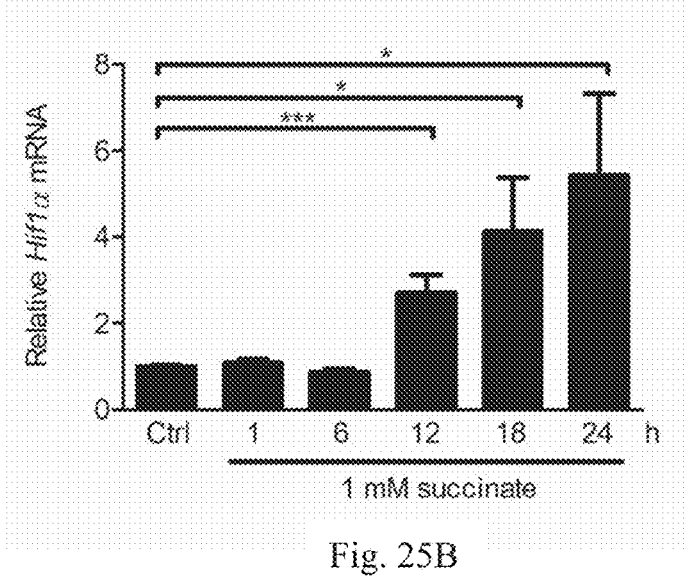

MAPK-, phosphatidylinositol 3-kinase (PI3K)-AKT-mTOR-, and AMP-activated protein kinase (AMPK)-mediated hypoxia-inducible factor-1α (HIF-1α) upregulation plays critical roles in macrophage activation and cancer progression. Therefore, it is investigated that whether these signaling molecules mediate the succinate actions. A549 and LLC cells are treated with succinate (1 mM) for the indicated time periods, and then cell lysates are immunoblotted with antibodies specific for HIF-1α, Akt, phospho-Akt, AMPK, phospho-AMPK, p38 MAPK, phospho-p38 MAPK, or β-actin. And Hif-1α mRNA in LLC cells treated with succinate (1 mM) for the indicated time periods are determined by qPCR. In LLC and A549 cells, succinate induces phosphorylation of p38 MAPK, AKT, and AMPK in a time-dependent manner and increases HIF-1α protein (FIG. 25A) and mRNA expression (FIG. 25B). Using selective kinase inhibitors, LLC cells are treated with different concentrations of LY294002 or SB202190 for 12 h, and Hif-1α mRNA is measured. After pretreating LLC cells with LY294002 or SB202190 for 1 h, LLC cells are stimulated with succinate (1 mM) for 12 h, and Hif-1α mRNA is measured. It is found that inhibitor of PI3K/AKT but not p38 MAPK abrogates constitutive and succinate-induced expression of Hif-1α (FIGS. 25C and 25D). To understand the role of SUCNR1 in driving HIF-1α expression, the expression level of HIF-1α in A549/shSUCNR1 is determined. HIF-1α expression in A549/shNC and A549/shSUCNR1 cells treated with succinate (1 mM) or dimethyl-ester succinate (DMS, 20 mM) for 12 h is measured by qPCR. Upregulation of HIF-1α is observed in succinate-treated A549/shNC cells (FIG. 25E). A549/shNC cells treated with membrane-permeable dimethyl-ester succinate (DMS) results in elevation of HIF-1α. However, HIF-1α expression induced by succinate but not DMS is abolished in A549/shSUCNR1 cells (FIG. 25F), suggesting that succinate induces HIF-1α expression in a SUCNR1-dependent manner while DMS-induced HIF-1α expression is SUCNR1-independent.

Since HIF-1α pathway is reported to mediate cancer metastasis through induction of EMT, it is evaluated that whether succinate promotes lung cancer cell migration and EMT via HIF-1α-dependent signaling. LLC and A549 lung cancer cells are treated with different concentrations of HIF-1α specific inhibitors, and cell migration is assessed in a transwell assay. Pharmacological inhibitors of HIF-1α, 2-MeOE2 and Bay 87-2243, inhibit succinate-mediated migration of LLC and A549 in a dose-dependent manner (FIG. 26A). Prolyl hydroxylase (PHD) controls HIF-1α protein stability by hydroxylation of two conserved proline residues in HIF-1α thereby accelerating its degradation. To provide additional evidence to support the crucial role of HIF-1α in succinate-induced cancer cell migration, cells are treated with PHD activator α-ketoglutarate (α-KG) or inhibitor dimethyloxalyl glycine (DMOG) for cell migration analyzation. α-KG reduces while DMOG increases succinate-mediated cell migration (FIGS. 26B and 26C). Furthermore, HIF-1α mRNA in A549/shNC or A549/HIF-1α cells is measured by qPCR, and cell migration of A549/shNC or A549/HIF-1α cells treated with or without succinate (1 mM) is determined by transwell assay. The results show that succinate-induced migration of A549s is suppressed by HIF-1α knockdown (A549/shHIF-1α) but not control (A549/shNC) (FIG. 26D). Additionally, A549 cells are pretreated with LY294002 or Bay 87-2243 for 1 h and treated with vehicle or succinate (1 mM) for 24 h. Cell lysates are immunoblotted with antibodies specific for E-cadherin, Vimentin, or □-actin. It shows that blockade of the PI3K by LY294002 or HIF-1α signaling by Bay 87-2243 suppresses succinate-mediated vimentin augmentation and E-cadherin reduction (FIGS. 26E and 26F).

The xenograft A549/shHIF-1α tumor model is used to confirm the role of HIF-1α in succinate-induced metastasis in vivo. A549/shNC or A549/HIF-1α cells are implanted subcutaneously into nude mice. Mice subsequently receive an intraperitoneal injection of succinate (100 mg/kg) twice weekly for 8 weeks. Lung metastatic nodules are significantly lower in mice inoculated with A549/shHIF-1α than in animals inoculated with A549/shNC (FIG. 27A). Furthermore, levels of E-cadherin and Vimentin in total protein extracted from primary subcutaneous tumor of A549/shNC or A549/shHIF1-α are determined by immunoblotted with antibodies specific for E-cadherin, Vimentin, or □-actin. The results show that succinate-induced E-cadherin reduction and vimentin elevation in primary subcutaneous A549/shHIF-1α tumor is reversed compared with A549/shNC tumor (FIG. 27B). Taken together, these results suggest that succinate-activated SUCNR1 promotes cancer metastasis by inducing HIF-1α-mediated EMT via PI3K/AKT signaling.

---

The invention claimed is:

1. An anti-succinate monoclonal antibody, comprising a heavy chain comprising the amino acid sequence of SEQ ID NO: 2; and a light chain comprising the an amino acid sequence of SEQ ID NO: 4.

2. The antibody of claim 1, wherein the antibody neutralizes serum succinate.

3. The antibody of claim 1, wherein the antibody inhibits cancer metastasis and the transformation of macrophage into tumor-associated macrophage.

4. The antibody of claim 1, wherein the antibody inhibits SUCNR1 signaling pathway.

5. The antibody of claim 1, wherein the antibody suppresses the expression of ARG1.

6. A humanized anti-succinate antibody, comprising a heavy chain sequence selected from the group consisting of the amino acid sequence of SEQ ID NOs: 9-13 and light chain sequence selected from the group consisting of the amino acid sequence of SEQ ID NOs: 14-21.

7. The antibody of claim 6, wherein the antibody neutralizes serum succinate.

8. The antibody of claim 6, wherein the antibody inhibits cancer metastasis and the transformation of macrophage into tumor-associated macrophage.

9. The antibody of claim 6, wherein the antibody inhibits SUCNR1 signaling pathway.

10. The antibody of claim 6, wherein the antibody suppresses the expression of ARG1.

* * * * *